US008491526B2

(12) United States Patent
Cronin et al.

(10) Patent No.: US 8,491,526 B2
(45) Date of Patent: Jul. 23, 2013

(54) THERAPEUTIC CELL APPLICATOR INSTRUMENT WITH MODULAR TIPS

(75) Inventors: Michael D. Cronin, Cincinnati, OH (US); Jerome R. Morgan, Cincinnati, OH (US); Patrick D. Dugan, Madeira, OH (US); Rebecca J. Mollere, Loveland, OH (US); John B. Schulte, West Chester, OH (US); David A. Witt, Maineville, OH (US); Joseph P. Schowalter, South Lebanon, OH (US); Eugene L. Timperman, Cincinnati, OH (US); Prasanna Malaviya, Mason, OH (US); Shailendra K. Parihar, Mason, OH (US); Shelby L. Cook Kornbluth, Foxborough, MA (US); Richard W. Timm, Cincinnati, OH (US); Donna L. Korvick, Maineville, OH (US); James A. Woodard, Jr., Mason, OH (US); Peter K. Shires, Hamilton, OH (US); Barbara L. Mattson, Cincinnati, OH (US); Matthew C. Miller, Cincinnati, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 395 days.

(21) Appl. No.: 12/779,477

(22) Filed: May 13, 2010

(65) Prior Publication Data

US 2011/0282381 A1    Nov. 17, 2011

(51) Int. Cl.
*A61M 37/00* (2006.01)
*A61M 1/00* (2006.01)
*A61M 5/00* (2006.01)

(52) U.S. Cl.
USPC .............. 604/82; 604/191; 604/128; 604/187

(58) Field of Classification Search
USPC ................ 604/82, 128, 151–153, 173, 181, 604/183, 187, 189, 191, 218
See application file for complete search history.

(56) References Cited

U.S. PATENT DOCUMENTS 5,192,269 A * 3/1993 Poli et al. ........................ 604/82
5,526,822 A  6/1996 Burbank et al.
(Continued)

FOREIGN PATENT DOCUMENTS
AT    410397 B   4/2003
EP    0 238 378   9/1987
(Continued)

OTHER PUBLICATIONS

U.S. Appl. No. 12/483,305, filed Jun. 12, 2009, Hibner et al.

(Continued)

*Primary Examiner* — Victoria P Shumate
(74) *Attorney, Agent, or Firm* — Frost Brown Todd LLC

(57) ABSTRACT

A surgical device comprises a housing, a bioprocessing module, an end effector, and a pumping device. The bioprocessing module comprises media reservoirs, fluid conduits in communication with the reservoirs, and a port through which media is expelled. The end effector is configured for insertion into a lumen and delivering a tissue repair composition into that lumen. The end effector has at least one fluid conduit extending therethrough and at least one orifice in communication with the fluid conduit. The fluid conduit in the first end effector is in fluid communication with the port on the bioprocessing module. The pumping device is operable to urge a tissue repair composition comprising at least a portion of the contents of the media reservoirs through the fluid conduit of the first end effector such that the tissue repair composition is expelled from the at least one orifice.

10 Claims, 53 Drawing Sheets

U.S. PATENT DOCUMENTS

| | | | |
|---|---|---|---|
| 5,694,951 A | 12/1997 | Bonutti | |
| 6,086,544 A | 7/2000 | Hibner et al. | |
| 6,656,162 B2* | 12/2003 | Santini et al. | 604/191 |
| 6,990,982 B1 | 1/2006 | Bonutti | |
| 7,115,100 B2 | 10/2006 | McRury et al. | |
| 7,442,171 B2 | 10/2008 | Stephens et al. | |
| 7,566,321 B2* | 7/2009 | Gumb et al. | 604/191 |
| 7,611,473 B2 | 11/2009 | Boock et al. | |
| 7,833,192 B2* | 11/2010 | Blumenthal et al. | 604/96.01 |
| 8,034,003 B2 | 10/2011 | Pesce et al. | |
| 2002/0161335 A1* | 10/2002 | Metzner et al. | 604/191 |
| 2002/0173745 A1* | 11/2002 | Santini et al. | 604/67 |
| 2003/0171670 A1* | 9/2003 | Gumb et al. | 600/411 |
| 2004/0078090 A1 | 4/2004 | Binette et al. | |
| 2004/0193071 A1 | 9/2004 | Binette et al. | |
| 2005/0038520 A1 | 2/2005 | Binette et al. | |
| 2005/0113736 A1 | 5/2005 | Orr et al. | |
| 2005/0125077 A1 | 6/2005 | Harmon et al. | |
| 2005/0197622 A1* | 9/2005 | Blumenthal et al. | 604/82 |
| 2005/0209563 A1* | 9/2005 | Hopping et al. | 604/151 |
| 2006/0031099 A1* | 2/2006 | Vitello et al. | 705/2 |
| 2007/0088268 A1 | 4/2007 | Edwards et al. | |
| 2008/0071385 A1 | 3/2008 | Binette et al. | |
| 2008/0161757 A1 | 7/2008 | Nayak et al. | |
| 2008/0214955 A1 | 9/2008 | Speeg et al. | |
| 2008/0234715 A1 | 9/2008 | Pesce et al. | |
| 2008/0311219 A1 | 12/2008 | Gosiewska et al. | |
| 2009/0112164 A1* | 4/2009 | Reilly et al. | 604/151 |
| 2009/0299328 A1 | 12/2009 | Mudd et al. | |
| 2010/0160819 A1 | 6/2010 | Parihar et al. | |
| 2011/0282270 A1* | 11/2011 | Hall et al. | 604/22 |
| 2011/0282337 A1* | 11/2011 | Hall et al. | 606/33 |
| 2011/0282373 A1* | 11/2011 | Chekan et al. | 606/170 |

FOREIGN PATENT DOCUMENTS

| | | |
|---|---|---|
| EP | 1410811 | 4/2004 |
| EP | 1985283 | 10/2008 |
| WO | WO 2006/124634 | 11/2006 |

OTHER PUBLICATIONS

U.S. Appl. No. 12/779,155, filed May 13, 2010, Houser et al.
International Search Report and Written Opinion dated Aug. 18, 2011 for Application No. PCT/US2011/036461.
International Search Report dated Aug. 11, 2011 for Application No. PCT/US2011/036456.
International Search Report date Aug. 24, 2011 for Application No. PCT/US2011/036468.
Restriction Requirement dated Jul. 26, 2012 for U.S. Appl. No. 12/779,400.
Office Action dated Oct. 12, 2012 for U.S. Appl. No. 12/779,400.
Office Action dated Oct. 5, 2012 for U.S. Appl. No. 12/779,536.
English Machine Translation of Austrian Patent No. AT 410397B. Apr. 25, 2003.

* cited by examiner

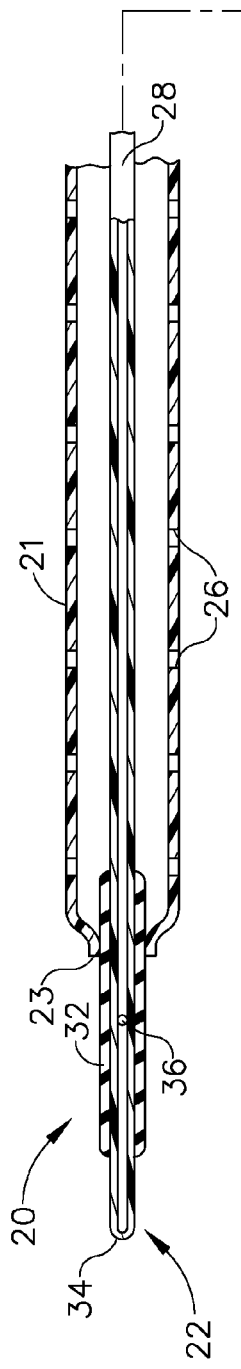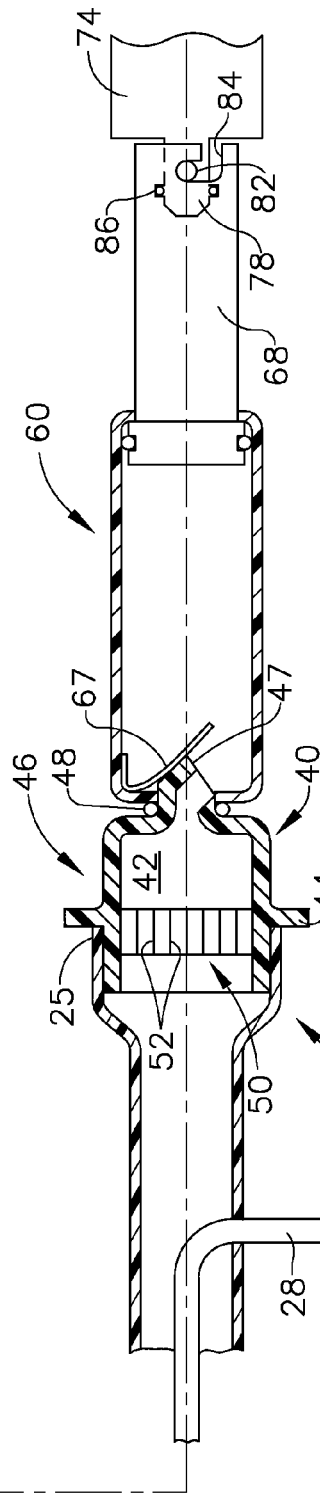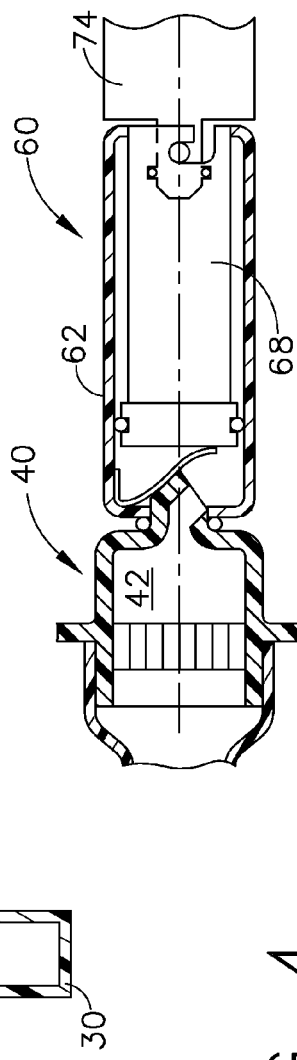
FIG. 2
FIG. 4

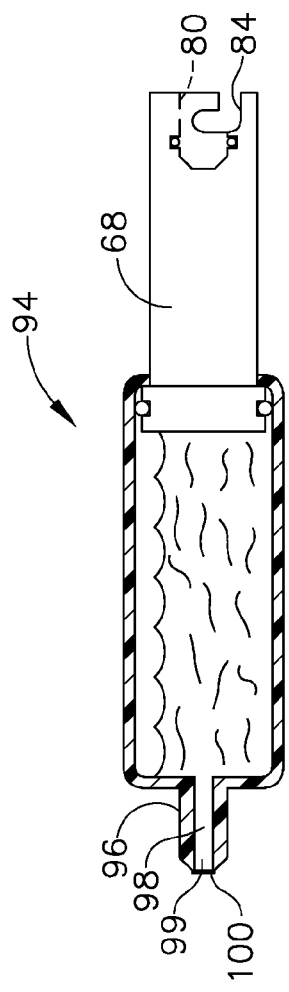
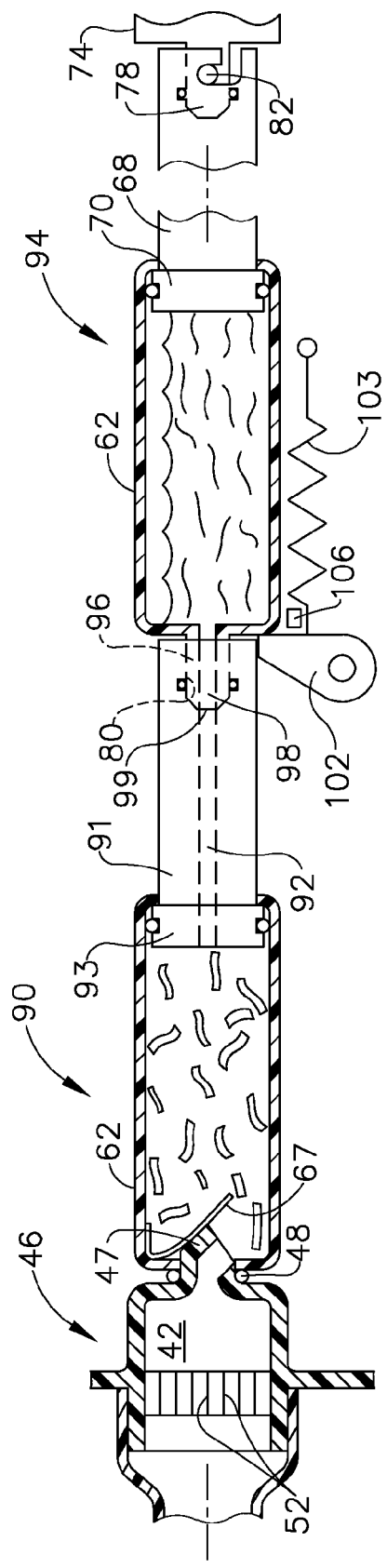
FIG. 6
FIG. 5

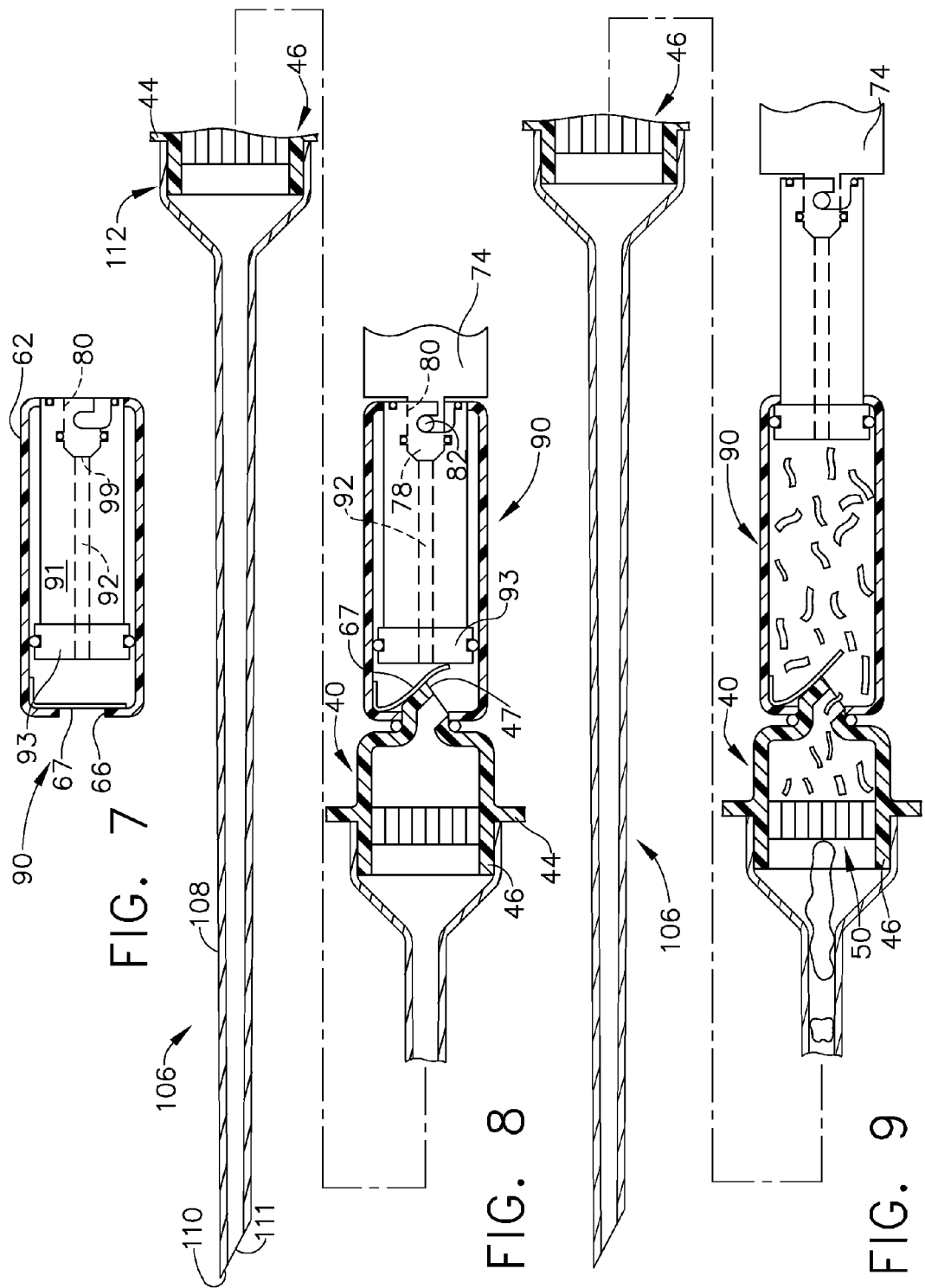

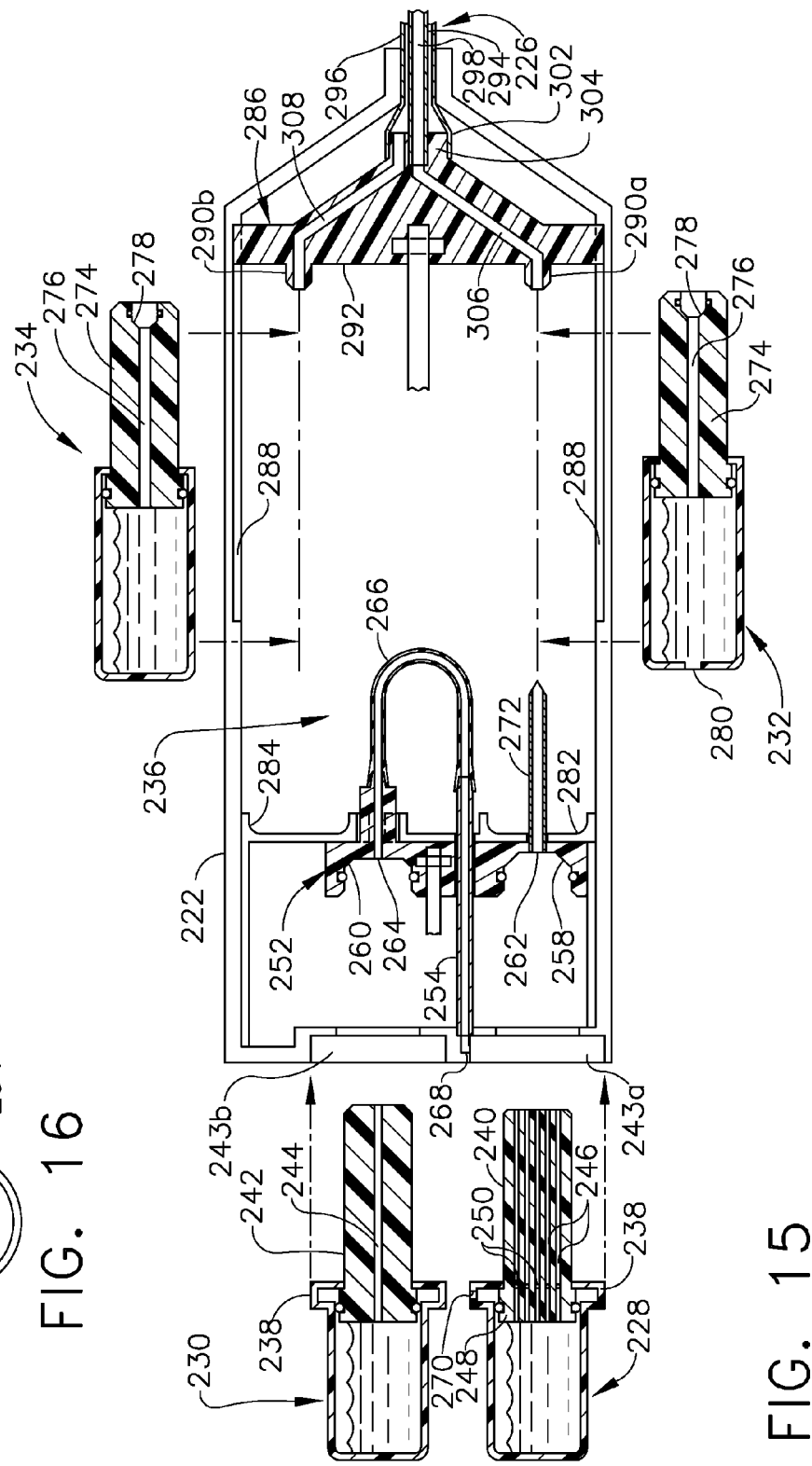
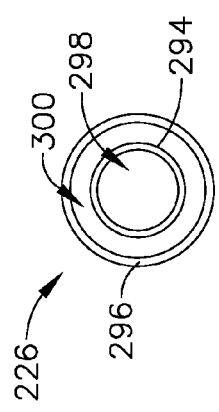
FIG. 15
FIG. 16

THERAPEUTIC CELL APPLICATOR INSTRUMENT WITH MODULAR TIPS

BACKGROUND

Fistulae can occur for a variety of reasons, such as, from a congenital defect, as a result of inflammatory bowel disease such as Crohn's disease, some sort of trauma, or as a side effect from a surgical procedure. Additionally, several different types of fistulae can occur in humans, for example, urethro-vaginal fistulae, vesico-vaginal fistulae, tracheo-esophageal fistulae, gastrointestinal fistulae, for example gastrocutaneous, enterocutaneous and colocutaneous fistulae, and any number of anorectal fistulae such as recto-vaginal fistula, recto-vesical fistulae, recto-urethral fistulae, and recto-prostatic fistulae. When fistulas form, they can track between intestinal segments or between an intestinal segment and other organs (e.g., bladder, vagina, etc.), adjacent tissue, or the skin. Fistulas are classified as internal when they communicate with adjacent organs (e.g., entero-enteric and rectovaginal fistulas, etc.) and external when they communicate with the dermal surface (e.g., enterocutaneous, peristomal and perianal fistulas, etc.).

Promoting and improving tissue healing around the fistula opening and in the fistula tract may be an important aspect of fistulae medical treatments. For instance, promoting and improving tissue healing may lead to quicker recovery times and lessen the opportunity for infection, particularly in a post-surgical context. Some advancements in the medical arts pertaining to systems, methods, and devices to promote and improve tissue healing in patients aim to add active biological components (e.g., tissue particles, stem cells, other types of cells, etc.) to a wound site (e.g., surgical site, accidental trauma site, etc.) or other defect site (e.g., caused by disease or other condition, etc.) to promote tissue regeneration or accelerate tissue healing. When adding biological components to a site, such components may be added independently or as part of a specifically designed matrix or other mixture depending on the condition being treated and goals of the treatment. Some examples of cell-based therapy technology are disclosed in U.S. Pub. No. 2008/0311219, entitled "Tissue Fragment Compositions for the Treatment of Incontinence," published Dec. 18, 2008, the disclosure of which is incorporated by reference herein. Additional examples of cell-based therapy technology are disclosed in U.S. Pub. No. 2004/0078090, entitled "Biocompatible Scaffolds with Tissue Fragments," published Apr. 22, 2004, the disclosure of which is incorporated by reference herein. Additional examples of cell-based therapy technology are disclosed in U.S. Pub. No. 2008/0071385, entitled "Conformable Tissue Repair Implant Capable of Injection Delivery," published Mar. 20, 2008, and issued Jan. 25, 2011 as U.S. Pat. No. 7,875,296, the disclosure of which is incorporated by reference herein.

Regardless of how the active biological components are delivered or applied to a site, the biological components must first be obtained and prepared. One approach for obtaining such biological components is to harvest the desired components from a healthy tissue specimen (e.g., in an adult human). Examples of devices and associated methods for collecting and processing harvested tissue are disclosed in U.S. Pub. No. 2004/0193071, and issued Sep. 14, 2010 as U.S. Pat. No. 7,794,408, entitled "Tissue Collection Device and Methods," published Sep. 30, 2004, the disclosure of which is incorporated by reference herein. Additional examples of devices and associated methods for collecting and processing harvested tissue are disclosed in U.S. Pub. No. 2005/0038520, entitled "Method and Apparatus for Resurfacing an Articular Surface," published Feb. 17, 2005, the disclosure of which is incorporated by reference herein. Additional examples of devices and associated methods for collecting and processing harvested tissue are disclosed in U.S. Pat. No. 7,611,473, entitled "Tissue Extraction and Maceration Device," issued Nov. 3, 2009, the disclosure of which is incorporated by reference herein. Additional examples of devices and associated methods for collecting and processing harvested tissue are disclosed in U.S. Pub. No. 2008/0234715, entitled "Tissue Extraction and Collection Device," published Sep. 25, 2008, and issued Oct. 11, 2011 as U.S. Pat. No. 8,034,003, the disclosure of which is incorporated by reference herein. Additional examples of devices and associated methods for processing harvested tissue are disclosed in U.S. Pub. No. 2005/0125077, entitled "Viable Tissue Repair Implants and Methods of Use," published Jun. 9, 2005, and issued Mar. 8, 2011 as U.S. Pat. No. 7,901,461, the disclosure of which is incorporated by reference herein. Additional examples of devices and associated methods for collecting and processing harvested tissue are disclosed in U.S. Pat. No. 5,694,951, entitled "Method for Tissue Removal and Transplantation," issued Dec. 9, 1997, the disclosure of which is incorporated by reference herein. Additional examples of devices and associated methods for collecting and processing harvested tissue are disclosed in U.S. Pat. No. 6,990,982, entitled "Method for Harvesting and Processing Cells from Tissue Fragments," issued Jan. 31, 2006, the disclosure of which is incorporated by reference herein. Additional examples of devices and associated methods for collecting and processing harvested tissue are disclosed in U.S. Pat. No. 7,115,100, entitled "Tissue Biopsy and Processing Device," issued Oct. 3, 2006, the disclosure of which is incorporated by reference herein.

Once harvested and suitably processed (e.g., incorporated with a scaffold, etc.), biological material such as tissue fragments may be applied to a wound site or other type of site within the human body in a variety of ways. Various methods and devices for applying such biological material are disclosed in one or more of the U.S. patent references cited above. Additional methods and devices for applying such biological material are disclosed in U.S. Pub. No. 2005/0113736, entitled "Arthroscopic Tissue Scaffold Delivery Device," published May 26, 2005, the disclosure of which is incorporated by reference herein.

While a variety of devices and techniques may exist for harvesting, processing, and applying biological components from a tissue specimen, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

FIG. 2 depicts a partial cross-sectional view of a portion of the lumen repair device shown in FIG. 1, with a media cartridge installed therein;

FIG. 3 depicts a partial cross-sectional view of a media cartridge used in the lumen repair device of FIG. 2;

FIG. 4 depicts a partial cross-sectional view of a portion of the lumen repair device shown in FIG. 2, with the contents expelled from the media cartridge installed therein;

FIG. 5 depicts a partial cross-sectional view of a portion of the lumen repair device shown in FIG. 1, with a tissue fragment cartridge and a tissue repair matrix cartridge installed therein;

FIG. 6 depicts a partial cross-sectional view of the tissue repair matrix cartridge shown in the lumen repair device of FIG. 5;

FIG. 7 depicts a partial cross-sectional view of the tissue fragment cartridge shown in the lumen repair device of FIG. 5;

FIG. 8 depicts a partial cross-sectional view of a portion of the lumen repair device shown in FIG. 1, with a tissue fragment cartridge installed therein for harvesting tissue fragments;

FIG. 9 depicts a partial cross-sectional view of a portion of the lumen repair device shown in FIG. 8, with the plunger of the tissue fragment cartridge withdrawn so as to pull tissue fragments into the cartridge;

FIG. 15 depicts a partial cross-sectional top view of the lumen repair device of FIG. 14;

FIG. 16 depicts a distal end view of the delivery probe of the lumen repair device of FIG. 14;

Figure 1:
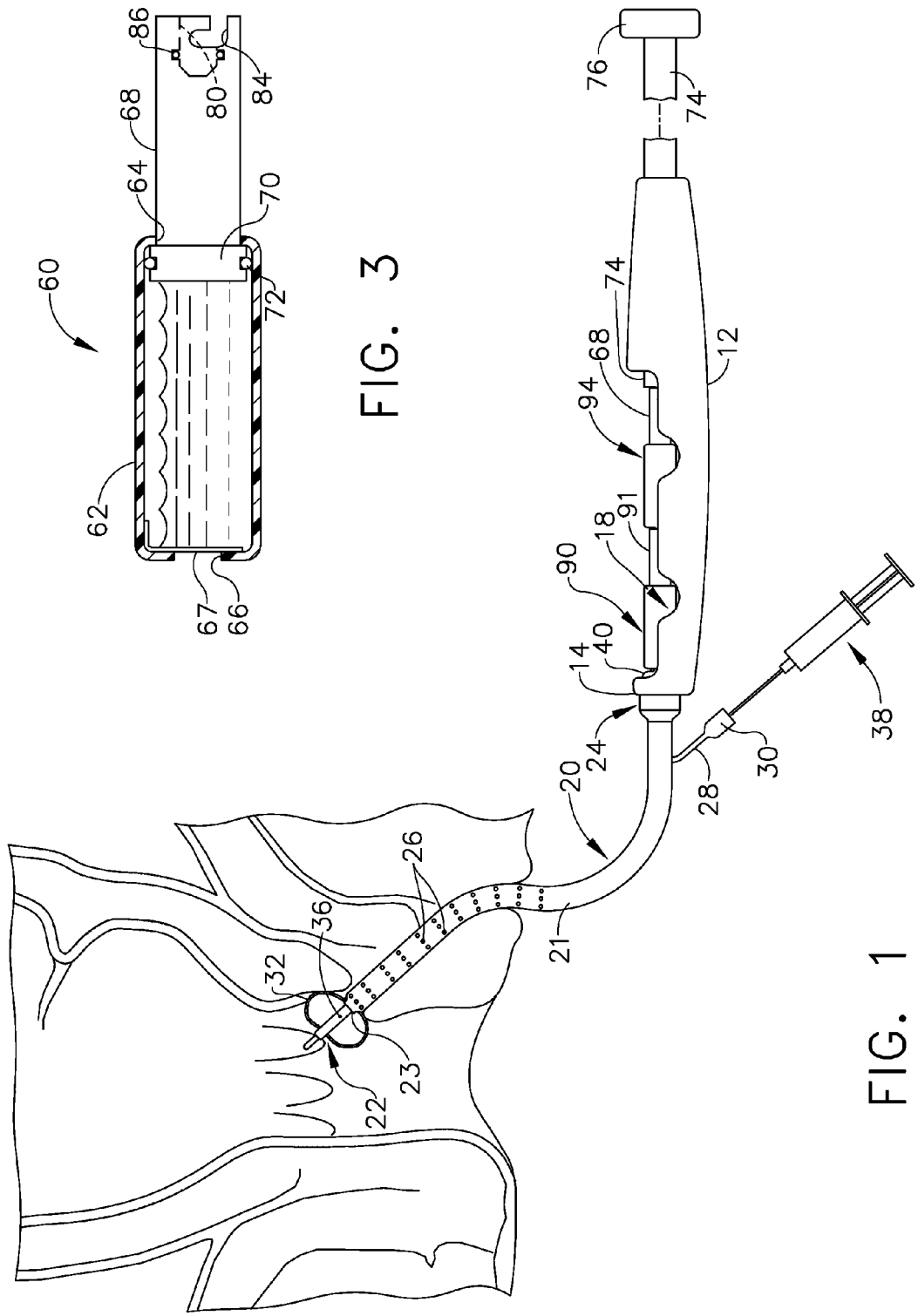
FIG. 1 depicts an exemplary lumen repair device being used to repair an anal fistula in a patient.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

I. Overview of Exemplary Treatment Compositions, Devices, and Methods

Examples described herein include devices that are operable to harvest tissue, mince or morcellate tissue, mix tissue particles with other medical fluid components, and/or dispense a medical fluid at a target site in a patient. As described in greater detail below, the medical fluid may include any of a variety of biocompatible materials that accelerate tissue healing, promote tissue regeneration, and/or provide other results. As used herein, the terms "tissue treatment composition," "tissue repair composition," and "medical fluid" should be read interchangeably. It should also be understood that a tissue treatment composition or medical fluid as referred to herein may have any suitable consistency, including but not limited to the consistency of a slurry.

A medical fluid as referred to herein may be derived from any biocompatible material, including but not limited to synthetic or natural polymers. The consistency of the medical fluid may be viscous, or gel-like, that of a slurry composed of microparticles, or any other suitable consistency. By way of example only, any fluid consistency that may permit injection through a catheter may be used. The medical fluid may also provide adhesive characteristics, such that once it is injected at a target site (e.g., into a fistula), the fluid coagulates or gels (e.g., allowing for a plug to be retained within a fistula). The medical fluid of the present example is also able to support cell migration and proliferation such that healing at a target site in a patient can occur. The fluid is suitable to be mixed with biological materials. Examples of medical fluid components include but are not limited to thrombin, platelet poor plasma (PPP) platelet rich plasma (PRP), starch, chitosan, alginate, fibrin, polysaccharide, cellulose, collagen, gelatin-resorcin-formalin adhesive, oxidized cellulose, mussel-based adhesive, poly(amino acid), agarose, amylose, hyaluronan, polyhydroxybutyrate (PHB), hyaluronic acid, poly(vinyl pyrrolidone) (PVP), poly(vinyl alcohol) (PVA), polylactide (PLA), polyglycolide (PGA), polycaprolactone (PCL), and their copolymers, VICRYL® (Ethicon, Inc., Somerville, N.J.), MONOCRYL material, PANACRYL (Ethicon, Inc., Somerville, N.J.), and/or any other material suitable to be mixed with biological material and introduced to a wound or defect site, including combinations of materials. Other suitable compounds, materials, substances, etc., that may be used in a medical fluid will be apparent to those of ordinary skill in the art in view of the teachings herein.

By way of example only, one or more components in a medical fluid or tissue treatment composition may comprise at least one viable tissue fragment having one or more viable cells that, once applied, can proliferate and integrate with tissue at a target site in a patient. For instance, viable cells may migrate out of a tissue particle and populate a scaffold material, which may be positioned at a target site in a patient. Such tissue fragments may have been harvested from the same patient in whom they are reapplied; or may have been harvested from another person or source. The tissue fragments may comprise autogenic tissue, allogenic tissue, xenogenic tissue, mixtures of any of the foregoing, and/or any other type(s) of tissue. The tissue fragments may include, for example, one or more of the following tissues or tissue components: stem cells, cartilage tissue, meniscal tissue, ligament tissue, tendon tissue, skin tissue, muscle tissue (e.g., from the patient's thigh, etc.), periosteal tissue, pericardial tissue, synovial tissue, fat tissue, bone marrow, bladder tissue, umbilical tissue, embryonic tissue, vascular tissue, blood and combinations thereof. Of course, any other suitable type of tissue may be used, including any suitable combination of tissue types. In some versions, the type of tissue used is selected from a tissue type most resembling the tissue at, near, or surrounding the target site (e.g., fistula, etc.).

Tissue for providing at least one viable tissue fragment may be obtained using any of a variety of tissue biopsy devices or using other types of tissue harvesting devices or techniques. Exemplary biopsy devices include those taught in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2007/0118048, entitled "Remote Thumbwheel for a Surgical Biopsy Device," published May 24, 2007, and issued Oct. 28, 2008 as U.S. Pat. No. 7,442,171; U.S. Pub. No. 2008/0214955, entitled "Presentation of Biopsy Sample by Biopsy Device," published Sep. 4, 2008; U.S. Non-Provisional patent application Ser. No. 12/337,942, entitled "Biopsy Device with Central Thumbwheel," filed Dec. 18, 2008, and published Jun. 24, 2010 as U.S. Pub. No. 2010/0160819; and U.S. Non-Provisional patent application Ser. No. 12/483,305, entitled "Tetherless Biopsy Device with Reusable Portion," filed Jun. 12, 2009, and issued Jun. 26, 2012 as U.S. Pat. No. 8,206,316. The disclosure of each of the above-cited U.S. Patents, U.S. Patent Application Publications, and U.S. Non-Provisional Patent Applications is incorporated by reference herein. Such biopsy devices may be used to extract a plurality of tissue specimens from one or more sites in a single patient. It should also be understood that any suitable device described in any other reference that is cited herein may be used to harvest tissue. Additional examples of devices that may be used to harvest tissue will be described in greater detail below. Other examples will be apparent to those of ordinary skill in the art in view of the teachings herein. Tissue harvesting sites may include the same sites in which tissue is reapplied as part of a treatment. In addition or in the alternative, tissue may be harvested from one site and then reapplied at some other site as part of a treatment. In some versions, the tissue is reapplied in the same patient from whom the tissue was originally harvested. In some other versions, the tissue is applied in a patient who is different from the patient from whom the tissue was originally harvested.

A tissue specimen may be obtained under aseptic conditions, and then processed under sterile conditions to create a suspension having at least one minced, or finely divided, tissue fragment. In other words, harvested tissue may be diced, minced or morcellated, and/or otherwise processed. Harvested tissue specimens may be minced and otherwise processed in any of a variety of ways. For instance, examples of tissue mincing and processing are described in U.S. Pub. No. 2004/0078090, the disclosure of which is incorporated by reference herein. Alternatively, merely exemplary non-conventional devices and techniques that may be used to mince and process tissue will be described in greater detail below, while other examples will be apparent to those of ordinary skill in the art in view of the teachings herein. In order to ensure viability of the tissue, agitators or other features of a mincing and/or mixing device may be designed to sever and mix (rather than crush or compress) the tissue. In some settings, tissue specimens may be minced and/or mixed in a standard cell culture medium, either in the presence or absence of serum. Tissue fragments may also be contacted with a matrix-digesting enzyme to facilitate cell migration out of an extracellular matrix surrounding the cells. Suitable matrix-digesting enzymes that may be used in some settings include, but are not limited to, collagenase, chondroitinase, trypsin, elastase, hyaluronidase, peptidase, thermolysin, and protease. The size of each tissue fragment may vary depending on the target location, method for delivering the treatment composition to the target site, and/or based on various other considerations. For example, the tissue fragment size may be chosen to enhance the ability of regenerative cells (e.g., fibroblasts) in the tissue fragments to migrate out of the tissue fragments, and/or to limit or prevent the destruction of cell integrity. In some settings, ideal tissue fragments are between approximately 200 microns and approximately 500 microns in size. As another merely illustrative example, ideal tissue fragments may be sized within the range of approximately 0.05 mm$^3$ and approximately 2 mm$^3$; or more particularly between approximately 0.05 mm$^3$ and approximately 1 mm$^3$. Of course, various other tissue fragment sizes may be ideal in various different settings.

In some versions, a medical fluid may comprise minced tissue fragments suspended in a biocompatible carrier. Suitable carriers may include, for example, a physiological buffer solution, a flowable gel solution, saline, and water. In the case of gel solutions, the tissue repair composition may be in a flowable gel form prior to delivery at the target site, or may form a gel and remain in place after delivery at the target site. Flowable gel solutions may comprise one or more gelling materials with or without added water, saline, or a physiological buffer solution. Suitable gelling materials include biological and synthetic materials. Exemplary gelling materials include the following: proteins such as collagen, collagen gel, elastin, thrombin, fibronectin, gelatin, fibrin, tropoelastin, polypeptides, laminin, proteoglycans, fibrin glue, fibrin clot, platelet rich plasma (PRP) clot, platelet poor plasma (PPP) clot, self-assembling peptide hydrogels, Matrigel or atelocollagen; polysaccharides such as pectin, cellulose, oxidized regenerated cellulose, chitin, chitosan, agarose, or hyaluronic acid; polynucleotides such as ribonucleic acids or deoxyribonucleic acids; other materials such as alginate, cross-linked alginate, poly(N-isopropylacrylamide), poly(oxyalkylene), copolymers of poly(ethylene oxide)-polypropylene oxide), poly(vinyl alcohol), polyacrylate, or monostearoyl glycerol co-Succinate/polyethylene glycol (MGSA/PEG) copolymers; and combinations of any of the foregoing. In addition to providing a flowable carrier solution for tissue fragments, a gelling agent(s) may also act as an adhesive that anchors the tissue repair composition at the target site. In some versions, an additional adhesive anchoring agent may be included in the tissue repair composition or medical fluid. Also, one or more cross-linking agents may be used in conjunction with one or more gelling agents in order to cross-link the gelling agent.

The concentration of tissue fragments in a carrier and/or one or more medical fluid components may vary depending on the target site location, method for delivering the treatment composition to the target site, and/or for various other reasons. By way of example, the ratio of tissue fragments to carrier (by volume) may be in the range of about 2:1 to about 6:1, or in the range of about 2:1 to about 3:1. The medical fluid may also include one more additional healing agents, such as biological components that accelerate healing and/or tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Similarly, in some versions where a scaffold plug is used in conjunction with a tissue repair composition, one or more of these additional biological components or additional treatment components may be provided on and/or within the scaffold plug. Some examples described herein may also include one or more adhesive agents in conjunction with viable tissue fragments.

As noted above, the harvested tissue may be combined with a scaffold material and/or other substances as part of a medical fluid, as described herein, for administration to the patient. To the extent that tissue is incorporated with a scaffold material, it should be understood that any suitable material or combination of materials may be used to provide a scaffold. By way of example only, scaffold material may include a natural material, a synthetic material, a bioabsorbable polymer, a non-woven polymer, other types of polymers, and/or other types of materials or combinations of materials. Examples of suitable biocompatible materials include starch, chitosan, cellulose, agarose, amylose, lignin, hyaluronan, alginate, hyaluronic acid, fibrin glue, fibrin clot, collagen gel, gelatin-resorcin-formalin adhesive, platelet rich plasma (PRP) gel, platelet poor plasma (PPP) gel, Matrigel, Monostearoyl Glycerol co-Succinate (MGSA), Monostearoyl Glycerol co-Succinate/polyethylene glycol (MGSA/PEG) copolymers, laminin, elastin, proteoglycans, polyhydroxybutyrate (PHB), poly(vinyl pyrrolidone) (PVP), polylactide (PLA), polyglycolide (PGA), polycaprolactone (PCL), and their copolymers, non-woven VICRYL® (Ethicon, Inc., Somerville, N.J.), MONOCRYL material, fibrin, non-woven poly-L-lactide, and non-woven PANACRYL (Ethicon, Inc., Somerville, N.J.). Polymers may include aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, polypropylene fumarate), polyurethane, poly(ester urethane), poly(ether urethane), and blends and copolymers thereof. Suitable synthetic polymers for use in examples described herein may also include biosynthetic polymers based on sequences found in collagen, laminin, glycosaminoglycans, elastin, thrombin, fibronectin, starches, poly(amino acid), gelatin, alginate, pectin, fibrin, oxidized cellulose, chitin, chitosan, tropoelastin, hyaluronic acid, silk, ribonucleic acids, deoxyribonucleic acids, polypeptides, proteins, polysaccharides, polynucleotides, and combinations thereof. Other suitable materials or combinations of materials that may be used will be apparent to those of ordinary skill in the art in view of the teachings herein. It should also be understood that tissue mixed with a scaffold material may have any suitable particle size, and that the resulting mixture may at least initially have the consistency of a slurry or have any other suitable consistency. In some versions, the tissue particles include an effective amount of viable cells that can migrate out of the tissue particle and populate the scaffold. The term "viable," as used herein, should be understood to include a tissue sample having one or more viable cells.

In some versions, one or more components in a medical fluid or tissue treatment composition comprise one or more healing agents that promote tissue regeneration at a target site (e.g., within a fistula) and/or accelerate tissue healing at the target site. Healing agents may include any of a variety of biocompatible materials that accelerate tissue healing and/or promote tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Some examples described herein may also include one or more adhesive agents in conjunction with viable tissue fragments.

Examples described herein relate to the repair (e.g., closing) of lumens in a patient, such as anal fistulas and other types of fistulas. In particular, examples described herein include devices used in at least part of a process to create and/or deliver tissue repair compositions or medical fluid into a lumen such as an anal fistula. It should be understood that anal fistulas and/or other types of fistulas may be relatively difficult to repair (e.g., close) in some settings. The goal of a surgical repair of an anal fistula may be to close the fistula with as little impact as possible on the sphincter muscles. In some settings, a tissue repair composition or medical fluid as described herein may be delivered into the fistula as a liquid composition, a flowable gel or paste, a scaffold plug, or a combination of the two or more of the foregoing (e.g., a porous scaffold plug loaded with a medical fluid composition, etc). Anal fistulas may also be repaired by injecting bioresorbable fibrin glue into the fistula that seals the fistula and promotes tissue growth across the fistula in order to provide permanent closure. Various bioresorbable plugs may also be used to repair anal fistulas. The plug may comprise, for example, collagen protein, tissue, stem cells, and/or other medical fluid components referred to herein; and the plug may be inserted into the fistula where it promotes tissue growth across the fistula as the plug dissolves. If desired, the plug may be secured in place using one or more fasteners and/or one or more adhesive agents. As another merely illustrative example, a medical fluid may be introduced within the fistula, and the medical fluid may eventually harden and then dissolve and/or be absorbed.

Prior to applying a medical fluid to a fistula, it may be desirable in some settings to debride the wall of a fistula (e.g., to remove epithelial cells, etc.), otherwise agitate the wall of the fistula, and/or otherwise treat the walls of the fistula. Merely illustrative examples of how the walls of a fistula may be treated and how a medical fluid may be applied in a fistula will be described in greater detail below. While examples herein are discussed in the context of an anorectal fistula, it should be understood that the following exemplary devices and techniques may be readily applied to various other types of fistulae. Similarly, while the present example relates to treatment of a fistula in a patient, it should also be understood that the following exemplary devices and techniques may be readily applied with respect to various other types of conditions in a patient. Other suitable ways in which the devices and techniques described herein may be used will be apparent to those of ordinary skill in the art in view of the teachings herein.

As used herein, the term "fluid communication" (or in some contexts "communication") means that there is a path or route through which fluid (gas, liquid or other flowable material) may flow between two components, either directly or through one or more intermediate components. Similarly, the term "conduit" encompasses a conduit within or integrated with a valve. In other words, fluid communication between two components means that fluid can flow from one component to another but does not exclude an intermediate component (e.g., a valve, etc.) between the two recited components that are in fluid communication. Similarly, two or more components may be in mechanical "communication" with each other even if intermediate components are interposed between those two or more components.

II. Exemplary Lumen Repair Device for Delivering Tissue Repair Compositions from Media Cartridges A. Cartridge-Receiving Housing with Interchangeable End Effectors FIGS. 1 and 2 depict an exemplary lumen repair device (10) for delivering a tissue repair composition into a lumen in a patient (e.g., in order to close or otherwise repair the lumen, etc.). In FIG. 1, lumen repair device (10) is depicted treating an anal fistula in a patient. However, lumen repair device (10) may be used to treat a variety of other types of fistulas or lumens. Lumen repair device (10) includes a housing (12), which also serves as a handle for device (10), for receiving a plurality of media reservoirs in the form of media cartridges therein. As further discussed herein, a variety of media cartridges are provided for insertion into housing (12). The media cartridges are configured to contain a flowable media to be discharged from the cartridge when located in the housing (12). An elongate end effector (20) is removably mounted to the distal end (14) of housing (12), and extends distally away therefrom. A pumping device is also provided in order to expel media from one or more cartridges positioned in the housing.

The exemplary end effector (20) of lumen repair device (10) may be used to clean and irrigate an anal fistula (or other lumen to be repaired), as well as to deliver a tissue repair composition to the fistula. In some versions as described herein, a multi-mode end effector may be provided that not only cleans/irrigates a fistula and delivers a tissue repair composition into the fistula, but also may be used to harvest tissue fragments for inclusion in the tissue repair composition. End effector (20) of the present example comprises a fluid conduit extending therethrough, and is foraminous along at least a portion of its length adjacent the distal end of end effector (20). In the example shown, end effector (20) comprises a hollow tube (21) that provides a fluid conduit therein, and a plurality of apertures (or orifices) (26) are provided about the circumference of hollow tube (21) adjacent the distal tip (23) of hollow tube (21). Thus, fluid (or other flowable media) such as saline or medical fluid, etc., urged through end effector (20) from its proximal end (24) towards its distal end (22), will be expelled through the plurality of apertures (26) provided about the circumference of end effector (20). As further described herein, any of a variety of flowable compositions may be expelled through the apertures (26), such as a cleaning solution, an antibiotic solution, or a tissue repair composition for closing the fistula.

While an end-user may maintain end effector (20) within the lumen being treated simply by manipulating housing (12) and/or end effector (20), the example shown also includes a balloon catheter on end effector (20) in order to help maintain end effector (20) in a fistula or other lumen. As shown in FIG. 2, a catheter (28) extends through at least a portion of the hollow tube (21) of end effector (20) and protrudes outwardly of the distal end of hollow tube (21). Catheter (28) is hollow and extends outwardly away from hollow tube (21) near the proximal end (24) of end effector (20). An inflation/deflation port (30) is also provided on the proximal end of catheter (28). A flexible, inflatable balloon (32) is provided at the opposite end of catheter (28), adjacent the distal tip (34) of the catheter (28). The distal tip (34) of catheter (28) is blunt in order to prevent trauma during insertion of the end effector (20) into a fistula, though it should be understood that distal tip (34) may have a variety of other configurations. The balloon (32) is positioned on catheter (28) so as to extend distally beyond the distal tip (23) of hollow tube (21). The distal tip (23) of hollow tube (21) of end effector (20) may be attached to the exterior surface of balloon (32) such that fluid urged through tube (21) will not be expelled through past the distal tip (23) of hollow tube (21).

Balloon (32) is generally cylindrical in shape, and is attached to catheter (28) at its distal and proximal ends. One or more apertures (36) are provided on catheter (28) in the region surrounded by balloon (32) for purposes of inflation. As best seen in FIG. 1, once the end effector (20) has been inserted into a fistula until the balloon (32) progresses past the internal opening of the fistula, balloon (32) is inflated with a fluid (e.g., air or a sterile liquid such as saline, etc.). In the example shown in FIG. 1, the distal end (22) of end effector (20) has been inserted into the exterior opening of an anal fistula (adjacent the patient's anus), advanced through the fistula until the balloon (32) has progressed just past the interior opening of the fistula within the anal canal, and the balloon (32) then inflated. Inflation of balloon (32) may be accomplished in any of a variety of ways known to those skilled in the art (e.g., in the same manner as a balloon on a Foley catheter is inflated). In the example shown in FIG. 1, a syringe (38) is used to inject an inflation fluid into the catheter (28) through inflation/deflation port (30). Port (30) may include a self-sealing septum such that a needle attached to the syringe (38) may be used to inject an inflation fluid into catheter (28). As another alternative, port (30) may comprise a Luer connector to which the barrel of syringe (38) is operatively attached. As yet another merely illustrative example, a charged fluid canister may be activated to inflate balloon (32).

By providing a balloon catheter assembly on end effector (20), the end effector (20), once properly positioned within the fistula or other lumen to be repaired, may be substantially maintained in place during the repair procedure. Following completion of the repair procedure, balloon (32) is simply deflated to allow removal of end effector (20) from the fistula. End effector (20), including both hollow tube (21) and catheter (28) may also be made of a flexible material in order to facilitate insertion of end effector (20) into a fistula or other lumen. By way of example, hollow tube (21) and catheter (28) may be made from a flexible material such as silicone, polyisoprene, Santoprene, or natural rubber.

End effector (20) may be operatively attached to housing (12) in any of a variety of ways that allow flowable media from one or more media cartridges inserted into the housing (12) to be urged through the fluid conduit provided by hollow tube (21) of end effector (20). In the example shown, a connector (40) is mounted in the distal end portion (14) of the housing (12). Connector (40) includes a bore (42) extending therethrough, as well as a flange (44) extending about the outer circumference of connector (40). Connector (40) is secured within the distal end portion (14) of housing (12), for example, by affixing the flange (44) to an interior distal end wall of the housing (12) such that a distal coupler (46) of connector (40) extends outwardly beyond the distal end portion (14) of housing (12). Distal coupler (46) on connector (40) is configured such that end effector (20) may be removably attached thereto, with the fluid conduit of end effector (20) in fluid communication with the bore (42) within connector (40). In the example shown, the proximal end (25) of flexible hollow tube (21) is simply friction fit over the distal coupler (46) of connector (40). Of course other configurations will be apparent to those skilled in the art, such as by friction fitting the proximal end (25) of hollow tube (21) within distal coupler (46), or by providing any of a variety of connector arrangements (e.g., male and female Luer lock fittings on proximal end (25) and distal coupler (46), etc.).

As best seen in FIG. 2, a tubular inlet port (47) is provided on the proximal end of the connector (40). Tubular inlet port (47) is in fluid communication with the bore (42), and is sized so as to be smaller in diameter than the interior diameter of bore (42). In the example shown, tubular inlet port (47) is angled with respect to the longitudinal axis of bore (42) in order to facilitate fluid flow through inlet port (47) from a fluid cartridge attached thereto (as further described herein). An O-ring (48) is provided about the exterior circumference of tubular inlet port (47) in order to sealingly engage the end wall of a fluid cartridge and prevent fluid leakage. Fluid of other flowable media urged through inlet port (47) will flow through bore (42) of connector (40), and into the fluid conduit of end effector (20) attached to the distal coupler (46).

In the present example, connector (40) also includes a screen member (50), which extends across at least a portion of bore (42). As further described in U.S. Non-Provisional patent application Ser. No. 12/779,155, entitled "METHODS AND APPARATUS FOR MORCELLATING TISSUE," filed on even date herewith, and published Nov. 17, 2011 as U.S. Pub. No. 2011/0282238, the disclosure of which is incorporated by reference herein, screen member (50) includes a plurality of elongate cutting members (52) extending across bore (42). Cutting members (52) are arranged so as to define a plurality of passageways therebetween. In one example, and as further described in patent application Ser. No. 12/779,155, published as U.S. Pub. No. 2011/0282238, cutting members (52) may comprise wire members arranged in a grid pattern. The cutting members (52) may be mounted within a frame. In the embodiment shown, cutting members (52) are mounted within connector (40) so as to extend across the entire interior diameter of bore (42). As further described herein, screen member (50) will morcellate soft specimens passing through bore (42) of connector (40) in either direction.

As mentioned previously, one or more media cartridges may be removably inserted into housing (12) so that the cartridge is in fluid communication with end effector (2) attached to housing (12). Media cartridges may be provided to an end-user pre-loaded with any of a variety of flowable media, or may be supplied empty for filling by an end-user. In some versions, the lumen repair device (10) may be provided as a kit which includes one or more pre-loaded media cartridges, as well as one or more empty media cartridges. Media cartridges may be provided in one or more configurations, depending on the intended use of the cartridge. For example, and as further described herein, a first type of media cartridge may be configured for insertion into housing (12) adjacent the distal end thereof, and operatively connected to tubular inlet port (47) of connector (40). A flowable media in the first type of media cartridge may be expelled therefrom into tubular inlet port (47), and thereafter into the fluid conduit of end effector (20). A second type of media cartridge may be configured for insertion into the proximal portion of housing (12), and operatively connected to the first type of fluid cartridge inserted in housing (12). In such an arrangement, the first and second types of media cartridges are in fluid communication with one another such that a flowable media in the second type of media cartridge may be expelled therefrom into the first type of media cartridge positioned in the housing (12), such that the flowable media from the second type of media cartridge will mix with the contents of the first type of media cartridge, with the mixture ultimately flowing from the first type of media cartridge.

FIG. 3 depicts an exemplary media cartridge (60) filled with a fluid media (e.g., a cleaning solution, saline, antibiotic solution, a medical fluid component, etc.). As further described below, media cartridge (60) is configured for insertion into housing (12), operatively connected to tubular inlet port (47) of connector (40). Media cartridge (60) comprises a cylindrical barrel (62) having proximal and distal orifices (64, 66) in the proximal and distal end walls of barrel (62). A plunger (68) extends through the proximal orifice (64) of barrel (62) such that the plunger head (70) is located within barrel (62), as shown. Plunger head (70) is larger in diameter than the proximal orifice (64) such that plunger head (70) will be retained within barrel (62). An O-ring (72) is provided about the exterior circumference of plunger head (70), and sealingly engages the interior wall of barrel (62). Alternatively, plunger head (70) may be made from a resilient, compressible material, and shaped so as to snugly and sealingly fit within barrel (62) (e.g., in a manner similar to the plunger head of a syringe). Plunger (68) functions similar to the plunger of a syringe in that, when plunger (68) is urged in the distal direction (i.e., towards distal orifice 66 of barrel (62)), flowable media within cartridge (60) will be expelled from the distal orifice (66).

Housing (12) of the present example includes a cartridge-receiving chamber (18), which is sized and configured to alignably and securely receive one or more media cartridges therein. Cartridge-receiving chamber (18) may include features that facilitate the insertion and removal of media cartridges therein, as well as ensuring the proper alignment of the media cartridges for the expulsion of media therefrom, as further described herein.

In order to prevent inadvertent release of media from cartridge (60) a valve or other seal may be provided at the distal end of cartridge (60). In the present example, a flap valve (67) is positioned over distal orifice (66), within barrel (62). Flap valve (67) may be shaped similar to distal orifice (66), but slightly larger to completely cover distal orifice (66). A portion of flap valve (67) is fastened to an interior wall of barrel (62), such as by adhesively attaching an upper end of flap valve (67) to a side wall of barrel (62) (as best seen in FIG. 2). In this manner, flap valve (67) may be opened by urging the portion of flap valve (67) extending over distal orifice (66) in the proximal direction. In the example shown, cartridge (60) is inserted into housing (12) such that tubular inlet port (47) of connector (40) extends through distal orifice (66) of cartridge (60) (see FIG. 2). Tubular inlet port (47) flexes flap valve (67) in the proximal direction, thus allowing fluid media to be urged through distal orifice (66) into connector (40). As best seen in FIG. 2, the angled configuration of tubular inlet port (47) will increase fluid flow as compared to a configuration in which inlet port (47) is not angled with respect to the longitudinal axis of cartridge (60) and bore (42) of connector (40). Cartridge (60) is also urged against O-ring (48) on tubular inlet port (47) to provide a sealed connection between inlet port (47) and the interior of cartridge (60).

Of course other structures besides a flap valve urged open by tubular inlet port (47) may be employed. For example, a septum or other penetrable wall may be provided at the distal end of cartridge (60). Tubular inlet port (47) may have a proximal end configured to puncture the penetrable wall of the cartridge in order to allow media to be expelled from the cartridge (60) into the tubular inlet port (47). By way of further example, the penetrable wall may comprise a resilient, self-sealing septum, and the tubular inlet port (47) may have a sharpened proximal end that punctures the resilient septum when the cartridge (60) is urged distally against tubular inlet port (47).

While media may be expelled from a fluid cartridge (60) inserted into housing (12) simply by manually pushing plunger (68) in the distal direction, in the present example a push rod (74) is slidably positioned within housing (12) and extends outwardly away from the proximal end (16) of housing (12) through an aperture (not shown) provided in the proximal end of housing (12). Push rod (74) has an enlarged head (76) at its proximal end for facilitating reciprocal movement of push rod (74). As further discussed herein, push rod (74) may be spring-biased in the proximal direction (away from housing (12)) in order to prevent inadvertent fluid expulsion. Push rod (74) may also be alignably supported within housing (12) by one or more alignment members (not shown), which allow for reciprocal movement of push rod (74) within housing (12). Push rod (74) and/or housing (12) may also include a ratcheting feature or similar type of feature to selectively restrict longitudinal movement of push rod (74) relative to housing (12).

As best seen in FIG. 2, the distal end of push rod (74) includes a connector element configured to securely attach to a complementary connector element provided on, or associated with, plunger (68) of media cartridge (60). In the example shown, a male coupling (76) is provided at the distal end of push rod (74). Male coupling (76) is sized and configured to be received in a female coupling chamber (80) provided in the proximal end of plunger (68) of cartridge (60). Male coupling (76) of the exemplary embodiment is cylindrical, with a frustoconical distal tip, and female coupling chamber (80) has a corresponding shape for snugly receiving male coupling (76) therein. In order to further alignably secure male coupling (76) within female coupling chamber (80), one or more pins (82) extend radially away from the outer surface of the cylindrical portion of male coupling (76), and are matingly received by corresponding J-shaped slots (84) on the proximal end of plunger (68) adjacent the female coupling chamber (80). In this manner, male coupling (76) is inserted into female coupling chamber (80), with pins (82) passing into J-shaped slots (84). When pins (82) abut against the distal end wall of J-shaped slots (84), the push rod (74) or the fluid cartridge (60) is simply twisted until the pins (82) are lockingly positioned within the J-shaped slots (84), as shown in FIG. 2. In order to further secure male coupling (76) within female coupling chamber (80), an O-ring (86) may be provided in a slot extending around the interior circumference of female coupling chamber (80), as shown. As further described herein, O-ring (86) may also provide a fluid-tight seal when a fluid conduit extends axially through plunger (68).

When a media cartridge (60) is inserted into the cartridge-receiving chamber (18) of housing (12), push rod (74) may be urged in the distal direction until male coupling (76) on the distal end of push rod (74) is received within female coupling chamber (80). The push rod (74) and/or the cartridge (60) is then rotated to lock pins (82) within the J-shaped slots (84) on plunger (68). Once the push rod (74) and the cartridge (60) are operably connected, the push rod (74) may be further urged distally in order to slide fluid cartridge (60) in the distal direction until the distal end of cartridge (60) is pressed against O-ring (48) on inlet port (47), with inlet port (47) extending through the distal orifice (66) of cartridge (60) so as to displace flap valve (67). Thereafter, as push rod (74) is further urged in the distal direction, plunger (68) of cartridge (60) is also urged distally so as to expel media contained therein. The flowable media will be expelled through inlet port (47) of connector (40), through the fluid conduit provided by hollow tube (21) of end effector (20), and expelled through apertures (26) on end effector (20). If the end effector (20) is positioned within a fistula, as shown in FIG. 1, the media will be applied throughout the interior of the fistula. By way of example, a cleaning solution, antibiotic solution, and/or saline solution may be applied to the interior walls of the fistula. Multiple solutions may be applied sequentially in this manner by expelling the contents of a first media-containing cartridge (60), removing the empty cartridge (60) from housing (12), inserting a new media-containing cartridge (60) into housing (12), and then expelling its contents into the fistula in the same manner. This process may be repeated any number of times in order to apply various types of treatment media to the interior wall of the fistula.

One of the medical fluid media compositions that may be applied to the interior of a fistula or other lumen is a tissue repair composition comprising a flowable suspension of one or more viable tissue fragments. The end-user may prepare such a tissue repair composition, for example, by harvesting one or more tissue specimens from the patient, and mincing the tissue specimen(s) into smaller fragments (e.g., to facilitate cell migration out to the tissue fragments once delivered into a fistula). The viable tissue fragments are then combined with a suitable carrier composition which may comprise, for example, saline, a buffer solution, water, or a gel solution. Various other healing agents may also be included in the tissue repair composition, such as growth factors. Various suitable medical fluid compositions are described above. The thus-prepared tissue repair composition may then be used to fill an empty media cartridge (60), and the cartridge (60) then inserted into housing (12) in the manner described previously. The tissue repair composition may then be expelled from the media cartridge (60) into hollow tube (21), and thereafter expelled through apertures (26) on end effector (20) so as to coat the interior of the fistula with the tissue repair composition. The tissue repair composition will then promote tissue regeneration and tissue healing in order to close the fistula.

In addition or in the alternative, a tissue repair composition may be formulated within housing (12) by combining a tissue repair matrix with one or more viable tissue fragments. The tissue repair matrix may comprise, for example, one or more of the carriers (e.g., gelling agents) described previously, as well as one or more additional healing agents. The tissue repair matrix and viable tissue fragments are provided in separate cartridges, which are placed into housing (12) in series. The tissue repair matrix is expelled distally from its cartridge into the next cartridge containing the viable tissue fragments in order to formulate a tissue repair composition within the tissue fragment cartridge. Thereafter, the tissue repair composition is expelled distally from the tissue fragment cartridge through the end effector (20) and through apertures (26) so as to coat the interior of the fistula.

FIG. 5 schematically depicts a tissue fragment cartridge (90) and a tissue repair matrix cartridge (94) positioned within housing (12) (not shown), in series. Tissue fragment cartridge (90) is similar in construction to media cartridge (60) and includes a tubular barrel (62) and a plunger (91) for expelling material from the tissue fragment cartridge (90). Tissue fragment cartridge (90) differs from media cartridge (60) in that a fluid conduit (92) extends through the interior of plunger (91). Fluid conduit (92) extends from the distal end wall of female coupling chamber (80), along the longitudinal axis of plunger (91), and through the plunger head (93).

Tissue repair matrix cartridge (94) is also similar in construction to media cartridge (60) and includes a tubular barrel (62) and a plunger (68) for expelling material from the tissue repair matrix cartridge (94) (see FIG. 6). Tissue repair matrix cartridge (94) may contain any medical fluid component referred to herein (or any suitable combination of such medical fluid components) or any other suitable fluid(s). While a fluid conduit is not provided in the plunger (68) of tissue repair matrix cartridge (94), the distal end of cartridge (94)

has a male coupling (96) that may be configured similar to male coupling (78) on the distal end of push rod (74). Thus, male coupling (96) is cylindrical, with a frustoconical distal tip such that male coupling (96) is snugly received within female coupling chamber (80) provided in the proximal end of plunger (91) of tissue fragment cartridge (90). In the present example, the male coupling (96) includes mounting pins for engaging the J-shaped slots the proximal end of plunger (91), though such mounting pins are merely optional. A fluid conduit (98) extends through the entire length of male coupling (96), and is aligned such that, when male coupling (96) of tissue repair matrix cartridge (94) is inserted into female coupling chamber (80) on plunger (91) of tissue fragment cartridge (90), the distal outlet (99) of fluid conduit (98) will be aligned with fluid conduit (92) in plunger (91) of tissue fragment cartridge (90). Thus, fluid conduits (92, 98) provide fluid communication between the interiors of tissue fragment cartridge (90) and tissue repair matrix cartridge (94). As shown in FIG. 6, a seal (100) is provided over a media filled tissue repair matrix cartridge (94) in order to prevent media leakage prior to use. Seal (100) may be removed by the end-user prior to use. In addition or in the alternative, plunger (91) may include a proximally extending hollow needle tip that is configured to pierce seal (100) and provide fluid communication from fluid conduit (98) to fluid conduit (92).

As shown in FIG. 5, tissue fragment cartridge (90) and tissue repair matrix cartridge (94) are positioned within housing (12) (not shown), in series. In order to prevent loss of fluid from cartridge (94), seal (100) may be removed from cartridge (94) while maintaining cartridge (94) in an upright orientation (distal end up). Thereafter, while maintaining repair matrix cartridge (94) in an upright orientation, tissue fragment cartridge (90) and tissue repair matrix cartridge (94) are connected to one another by pushing male coupling (96) into female coupling chamber (80) of plunger (91) of the tissue fragment cartridge (90) until a snug fit is achieved. The coupled cartridges (90, 94) are then inserted into housing (12), with push rod (74) fully retracted in the proximal direction. Push rod (74) is then urged in the distal direction until male coupling (76) on the distal end of push rod (74) is received within female coupling chamber (80) in plunger (68) of tissue repair matrix cartridge (94). The push rod (74) and/or the coupled cartridges (90, 94) is then rotated to lock pins (82) within the J-shaped slots (84) on plunger (68) of repair matrix cartridge (94).

In the example shown schematically in FIG. 5, a cam (102) is provided within housing (12). Cam (102) is pivotally mounted within housing (12) and is resiliently biased, in the direction shown by the arrow in FIG. 5, by a spring (103). Cam (102) is positioned such that, when coupled cartridges (90, 94) are inserted into housing (12) in the manner described above and as shown in FIG. 5, the cam (102) will press against the outer distal end wall of repair matrix cartridge (94). In this manner, spring-biased cam (102) will urge repair matrix cartridge in the proximal direction. As further discussed below, by providing a spring-biased cam (102) which urges repair matrix cartridge (94) in the proximal direction, a dual-stage plunger action is provided. A fixed stop member (104) is also provided in housing (112) and is located so as to limit rearward rotation of the cam (102).

Once the push rod (74) and repair matrix cartridge (94) are operably connected, the push rod (74) may be further urged distally in order to slide coupled cartridges (90, 94) in the distal direction until the distal end of tissue fragment cartridge (90) is pressed against O-ring (48) on inlet port (47), with inlet port (47) extending proximally through the distal orifice (66) of cartridge (90) so as to displace flap valve (67).

Thereafter, as push rod (74) is further urged in the distal direction, with end effector (20) positioned in a fistula as shown in FIG. 1, plunger (68) of tissue repair matrix cartridge (94) is also urged distally so as to expel the flowable media (i.e., a tissue repair matrix) contained therein. The media will be expelled through fluid conduit (98) of male coupling (96), through fluid conduit (92) in plunger (91) and expelled into tissue fragment cartridge (90). Because tissue repair matrix cartridge (94) is spring-biased in the proximal direction (i.e., away from tissue fragment cartridge (90)), plunger (91) on tissue fragment cartridge (90) will not be urged distally until all or nearly all of the tissue repair matrix has been expelled from cartridge (94) into tissue fragment cartridge (90). In other words, the spring constant of spring (103) is great enough to resist distal movement of barrel (62) of the tissue repair matrix cartridge (94) within housing (12) as plunger (98) is distally advanced in tissue repair matrix cartridge (94). This dual-stage plunger action allows the tissue repair matrix composition to be mixed with the tissue fragments in cartridge (90) as the repair matrix composition is expelled from cartridge (94) into cartridge (90), thus formulating a tissue repair composition comprising the tissue fragments suspended in the tissue repair matrix.

Once the tissue repair matrix has been expelled into the tissue fragment cartridge (90) so as to formulate the tissue repair composition, push rod (74) is further urged in the distal direction. At this stage, the resilient bias of spring (103) is overcome, such that cam (102) rotates forward, allowing barrel (62) of the tissue repair matrix cartridge (94) to translate distally. Plunger head (70) will press against the interior distal wall of barrel (62) of the tissue repair matrix cartridge (94), and male coupling (96) of cartridge (94) will urge plunger (91) of tissue fragment cartridge (90) in the distal direction. Distal movement of plunger (91) will cause the tissue repair composition comprising viable tissue fragments suspended in the tissue repair matrix to be expelled from cartridge (90), through inlet port (47) of connector (40), through the fluid conduit provided by hollow tube (21) of end effector (20), and expelled through apertures (26) on end effector (20). If the end effector (20) is positioned within a fistula, as shown in FIG. 1, the tissue repair composition will be applied throughout the interior of the fistula. If desired, tissue repair matrix cartridge (94) and tissue fragment cartridge (90) may be replaced in housing (12) by an additional media cartridges (60), and media within the additional cartridge expelled into the fistula. This process may be repeated any number of times to apply additional media to the interior of the fistula.

It should be noted that in order to reduce the number of separate components to be manufactured, media cartridge (60) may be constructed the same as tissue fragment cartridge (90) (e.g., with a fluid conduit or bore extending through then entire length of the plunger). If the thus-constructed cartridge is not to be used in series with another upstream cartridge such as tissue repair matrix cartridge (94), the fluid conduit (92) in plunger (91) may be blocked such as by positioning a plug or other sealing member within fluid conduit (92) between the distal end wall of female coupling chamber (80) and the distal end of plunger head (93). Alternatively, a seal may be provided over the distal end of plunger head (93) so as to sealingly cover the distal end of fluid conduit (92). It should also be noted that, when only a single media cartridge such as cartridge (60) is inserted into housing (12), spring-biased cam (102) will be in facing relationship to the distal end of push rod (74). Thus, cam (102) may also be used to spring-bias push rod (74) in the proximal direction, and thus prevent inadvertent expulsion of media from cartridge (60).

Lumen repair device (10) may be supplied to an end-user with one or more empty tissue fragment cartridges (90) depicted in FIG. 7. The end-user may then fill cartridge (90) with one or more viable tissue fragments harvested or obtained in any of a variety of manners. Alternatively, a coring biopsy probe (106) for harvesting viable tissue specimens may be used in conjunction with lumen repair device (10) in order to harvest one or more viable tissue specimens from a patient directly into a tissue fragment cartridge (90). In the example shown in FIGS. 8-9, biopsy probe (106) comprises an elongate cannula (108) having a sharpened distal tip (110). The proximal end (112) of cannula (108) is configured for attachment to the distal coupler portion (46) of connector (40) provided at the distal end of housing (12). In the present example, the proximal end (112) of cannula (108) is merely friction fit over the coupler portion (46). Alternatively, any of a variety of couplings may be used instead of, or in addition to, a friction fit. It should also be understood that biopsy probe (106) may have a variety of alternative configurations. By way of example only, biopsy probe (106) may have a closed distal end, a transverse aperture located proximal to the distal end, and an inner tubular cutter that translates relative to the transverse aperture to sever tissue protruding through the transverse aperture. Other suitable configurations for biopsy probe (106) will be apparent to those of ordinary skill in the art in view of the teachings herein.

Once biopsy probe (106) has been attached to housing (12), as shown, an empty tissue fragment cartridge (90) is inserted into housing (12). The male coupler (78) on the distal end of push rod (74) is inserted into female coupling chamber (80) in the proximal end of plunger (91) of cartridge (90). Thereafter, the push rod (74) is urged distally in order to slide cartridge (90) in the distal direction until the distal end of tissue fragment cartridge (90) is pressed against O-ring (48) on inlet port (47), with inlet port (47) extending through the distal orifice (66) of cartridge (90) so as to displace flap valve (67).

Push rod (74) is then urged further in the distal direction until plunger head (93) of cartridge (90) is pressed against (or nearly against) flap valve (67) as shown in FIG. 8. With the push rod (74) maintained in this position (e.g., urged distally as far as possible), the sharp distal tip (110) of cannula (108) is urged into tissue at the desired biopsy location. Tissue specimens may be obtained from any of a variety of locations, such as a muscle in the thigh, abdomen or other large muscle group having a high fat content. Once distal tip (110) has been advanced through the patient's tissue to the desired location, the push rod (74) is pulled in the proximal direction. As push rod (74) moves proximally away from cartridge (90), plunger (91) is pulled proximally away from the interior distal end surface of the cartridge (90). Because plunger head (93) is in sealing engagement with the interior wall of cartridge (90), proximal movement of plunger head (93) will create a vacuum within barrel (62) of cartridge (90) and within cannula (108), which is in fluid communication therewith. By creating such a vacuum, a soft tissue sample will be pulled into the distal orifice (111) provided at the distal end (110) of cannula (108). As the user continues to pull or urge push rod (74) in the proximal direction, the soft tissue specimen will move proximally through the interior of cannula (108). The amount of the harvested tissue specimen may be increased by slightly tipping cannula (108) relative to the axis of insertion and/or rotating cannula (108) about its own axis. As shown in FIG. 9, soft tissue specimens will be pulled by the induced vacuum through screen member (50) within housing (40) such that the tissue specimens are morcellated into smaller tissue fragments. In particular, screen member (50) acts as a die to morcellate the tissue specimens as they are extruded through screen member (50) under the influence of vacuum.

After one or more viable tissue fragments have been deposited into tissue fragment cartridge (90), biopsy probe (106) may be removed from the tissue repair device (10) and replaced by end effector (20). Tissue fragment cartridge (90) may be removed from the housing (12) in order to be operatively connected to a tissue repair matrix cartridge (94) in the manner described previously. Alternatively, tissue fragment cartridge (90) may remain in housing (12), and a tissue repair matrix cartridge (94) may be inserted into housing (12) and be operatively connected to tissue fragment cartridge (90) and push rod (74). Thereafter, the end effector (20) may be inserted into the anal fistula as shown in FIG. 1, and a tissue repair composition or medical fluid comprising a suspension of the tissue fragments in the tissue repair matrix then ejected through the apertures (26) on the end effector (20) so as to coat the interior of the fistula, as described previously.

An exemplary anal fistula repair procedure using lumen repair device (10) will now be described. End effector (20) is attached to housing (12) and a media cartridge (60) is inserted into housing (12) as shown schematically in FIG. 2. The distal end of end effector (20) is inserted through the external opening of the fistula and advanced through the length of the fistula the balloon (32) progresses past the internal opening of the fistula into the anal canal. Balloon (32) is then inflated with a fluid (e.g., air or a sterile liquid such as saline), using syringe (38). End effector (20 may be pulled away from the external fistula opening so as to seat inflated balloon (32) at least partially within the interior opening of the fistula or adjacent to the interior opening of the fistula. Once end effector (20) has been suitably positioned within the fistula, push rod (74) is urged distally so as to urge media from fluid cartridge (60) through the interior of end effector (74) to be expelled through apertures (26) into the fistula. The fluid may comprise, for example, saline or a cleaning solution. By way of example, a suitable cleaning solution may comprise an aqueous solution containing one or more iodine compounds, acetic acid, chlorhexidine, hydrogen peroxide, and/or silver compounds. If desired one or more additional media compositions may be applied to the interior of the fistula. While maintaining end effector (20) within the fistula, empty media cartridge (60) may be removed from housing (12) and replaced with another media-filled cartridge (60) containing, for example, an antibiotic solution. Push rod (74) may once again be urged distally in order to expel the antibiotic solution through apertures (26) into the fistula. This process may be repeated any number of times. It should also be understood that a debriding end effector (not shown) may be coupled with housing (12) and be used to debride the fistula before, during, and/or after the cleaning of the fistula. Various examples of debriding end effector configurations will be described in greater detail below, while other examples will be apparent to those of ordinary skill in the art in view of the teachings herein.

Housing (12) may then be detached from end effector (20), while end effector (20) is maintained within the fistula by inflated balloon (32). An empty tissue fragment cartridge (90) is then inserted into housing (12) in the manner described previously, and biopsy probe (106) attached to the distal end of housing (12). One or more soft tissue specimens are then harvested using biopsy probe (106) in the manner described above so as to provide one or more viable tissue fragments within cartridge (90) in housing (12). Biopsy probe (106) is then detached from housing (12). In some other versions, the tissue cartridge (90) may have been previously filled (e.g., before the above process of cleaning and/or debriding the fistula was started).

Next, a filled tissue repair matrix cartridge (94) inserted into housing (12), and is operatively attached to tissue fragment cartridge (90) and push rod (74) in the manner described previously. Housing (12) is then reattached to end effector (20) which is still positioned within the fistula. In some versions where cartridge (90) was already filled with tissue before the process of cleaning/debriding the fistula began, end effector (20) may remain coupled with housing (12) before, during, and after the acts of removing media cartridge (60) from housing (12) and adding cartridges (90, 94) to housing. Push rod (74) is then urged distally so as to deliver the tissue repair matrix to the interior of cartridge (90), where it mixes with the viable tissue fragments to form a tissue repair composition comprising a suspension of the tissue fragments in the repair matrix. As push rod (74) is urged further distally, the tissue repair composition is urged out of cartridge (90) and expelled from apertures (26) so as to coat the interior walls of the fistula. It should be understood that screen member (50) may assist in further mixing the tissue and matrix as the mixture is expelled distally through screen member.

It should also be mentioned that, while the example described above utilizes end effector (20) both for fistula cleaning and delivery of the tissue repair composition, separate end effectors may be provided for these purposes. Thus, different end effectors may be used for fistula cleaning and delivering the tissue repair composition to the interior of the fistula. Other suitable variations, components, features, configurations, and operabilities of lumen repair device (10) will be apparent to those of ordinary skill in the art in view of the teachings herein.

B. Multi-Use End Effector with Interchangeable Handles

Figure 9A:
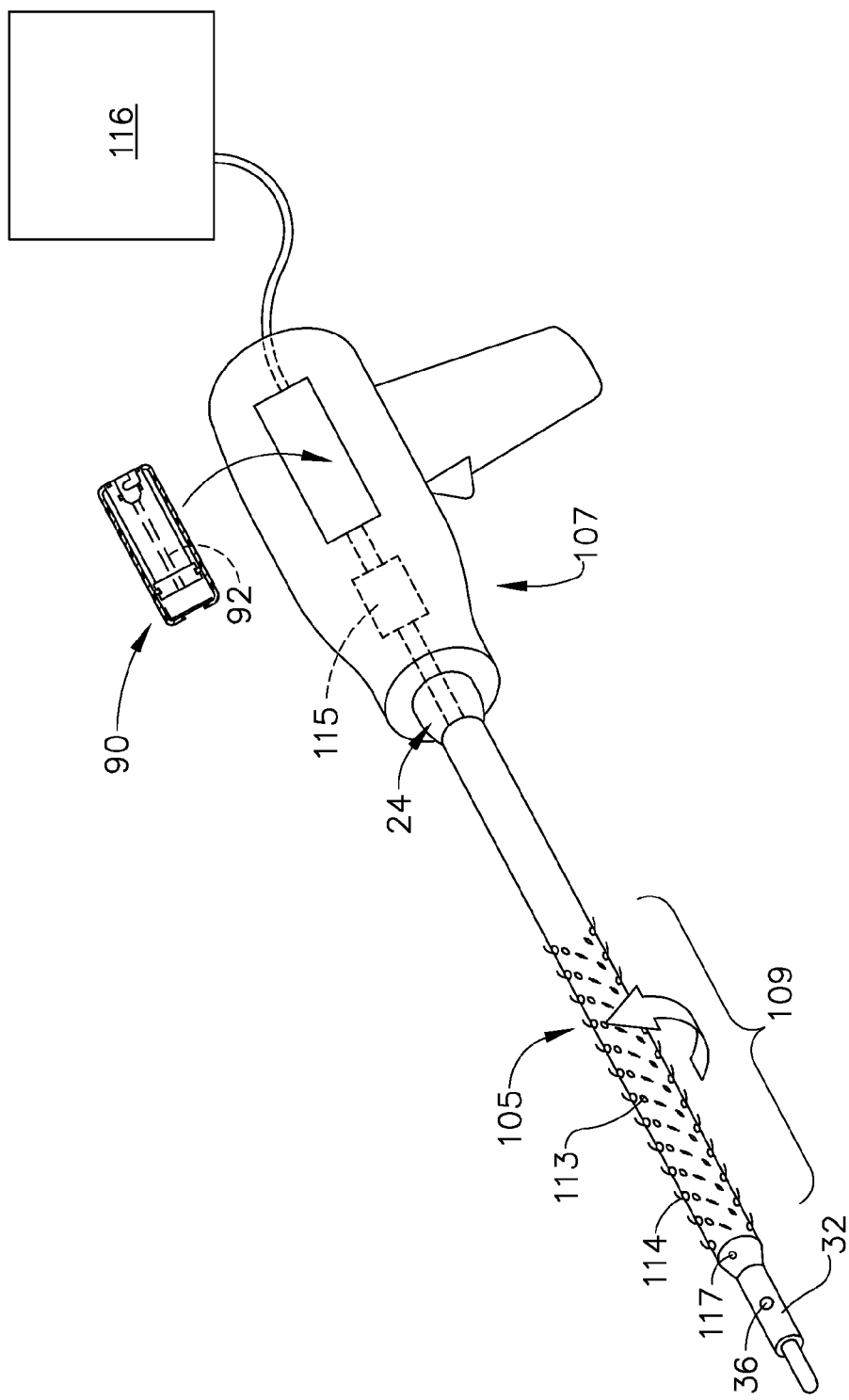
FIG. 9A depicts a schematic view of another exemplary device for harvesting tissue specimens.

FIG. 9A depicts an alternative example of an end effector (105) that may used in conjunction with housing (12) described previously. The proximal end of end effector (105) is similar to that of end effector (20), and the distal end of end effector (105) includes a balloon catheter similar to that of end effector (20). Once again, the balloon catheter may be inflated and deflated using an inflation/deflation port (not shown in FIG. 9A).

End effector (105), like end effector (20), may be used for cleaning/irrigating a fistula as well as for delivering a tissue repair composition into the fistula. End effector (105) may also be used to harvest one or more tissue fragments by attaching end effector (105) to a tissue harvesting handle (107). In order for end effector (105) to be used to harvest tissue fragments, a tissue cutting section (109) is provided on end effector (105) adjacent its distal end. Tissue cutting section (109) is similar to the tissue cutting section (750) of harvesting end effector (740) (FIGS. 46-47), described further herein. Thus, a tissue grating surface extends about tissue cutting section (109), and is structured similar to a cheese grater. In particular, a plurality of openings (or orifices) (113) are provided in the outer wall of tissue cutting section (109) of end effector (105), and cutting teeth (114) extend away from the outer wall of tissue cutting section (109) so as to partially surround each of the openings (113). Tissue cutting section (109) of end effector (105) may be inserted into soft tissue in a patient (e.g., muscle) and then rotated such that cutting teeth (114) will cut off small pieces of tissue, which will pass through openings (113) into the interior of hollow end effector (105) within tissue cutting section (109). Cutting teeth (114) and openings (113) may be provided in any of a variety of shapes and configurations, including but not limited to slits, slots, triangular openings with sharp raised edges, diamond-shaped openings with sharp raised edges, cheese-grater configurations, etc.

During repair of a fistula (e.g., an anal fistula), end effector (105) may be used in place of end effector (20) throughout the entire process. Thus, end effector (105) is attached to housing (12) described previously, and various media such as a cleaning solution and an antibiotic solution expelled from media cartridges installed in housing (12) into the interior of end effector (105) so as to then be expelled through openings (113) into the fistula. Thereafter, housing (12) is removed from end effector (105), and a motorized biopsy handle (107) attached to the proximal end of end effector (105), as shown in FIG. 9A. Biopsy handle (107) includes a motor (115) operable to cause end effector (105) to rotate and/or reciprocate when actuated (e.g., by an actuator such as a switch provided on handle (107)). A tissue fragment cartridge (90) may also be inserted into handle (107), in communication with the interior of end effector (105). A vacuum source (116) is operably attached to handle (107) such that a vacuum may be pulled through fluid conduit (92) of tissue fragment cartridge (90). Vacuum source (116) may comprise a conventional electromechanical vacuum pump, a manually operated pump (e.g., plunger in barrel, similar to a syringe, etc), or any other suitable type of vacuum source (116).

Following cleaning/irrigation of the fistula, handle (107) is attached to end effector (105). End effector (105) may be removed from the fistula for harvesting, or may remain in the fistula in order to harvest tissue fragments from the lining of the fistula itself. Motor (115) is then actuated so as to cause end effector (105) to rotate and/or reciprocate within the fistula. Cutting teeth (114) will cut off small pieces of tissue, which then pass through openings (113) into the interior of hollow end effector (105) (along with fluid from within the tissue at the harvesting site). The tissue fragments and fluid will then be pulled under vacuum into tissue fragment cartridge (90) within handle (107). In order to facilitate tissue harvesting, saline or other fluid may be injected into the fistula or other biopsy site while end effector (105) is rotated and/or reciprocated. For example, one or more irrigation apertures (117) may be provided on or near the distal end of tissue cutting section (109), and saline or other fluid delivered to aperture (117) through a fluid conduit (not shown) extending through end effector (105) and connected at its proximal end to a source of saline or other fluid (not shown).

After tissue fragments have been harvested using end effector (105), tissue fragment cartridge (90) containing the harvested tissue fragments is removed from handle (107) and inserted into housing (12) along with a tissue repair matrix cartridge (94) in the manner described previously. Motorized biopsy handle (107) is also detached from end effector (105); and housing (12) is reattached to the proximal end of end effector (105). If tissue harvesting was not performed in the fistula, the distal end of end effector (105) is inserted back into the fistula. The repair matrix is then expelled into tissue fragment cartridge (90) in the manner described previously, and the thus formulated tissue repair composition or medical fluid is delivered into the fistula through openings (113) on end effector (105).

III. Exemplary Lumen Repair Device Having Mixing Chamber for Formulating and Delivering a Tissue Repair Composition FIGS. 10-13 depict another exemplary lumen repair device (120) that may be used to formulate a tissue repair composition within the device (120) and deliver that tissue repair composition into a lumen in a patient in order to close, repair, and/or otherwise treat a bodily lumen. By way of example, device (120) may be used to repair a fistula, such as an anal fistula. Lumen repair device (120) of this example has a housing that comprises a handle (122) having a grip portion (124) at a proximal end of handle (122), and a mixing chamber (126) at a distal end of handle (122). It will be understood that, even though mixing chamber (126) is depicted as being an integral component of handle (122), a separate mixing chamber operatively attached to handle (122) may be used instead. Mixing chamber (126), as shown, comprises a hollow cylindrical structure having a fluid conduit (128) in fluid communication with the interior of mixing chamber (126). Fluid conduit (128) is configured for selectively dispensing various components of a tissue repair composition into mixing chamber (126), where these components are combined to formulate a tissue repair composition or medical fluid. The tissue repair composition may comprise, for example, at least one viable tissue fragment suspended in a tissue repair matrix (e.g., fibrin, growth factors and saline) and/or any other medical fluid component(s) referred to herein. The thus-formulated tissue repair composition is then expelled from mixing chamber (126) through an end effector comprising a delivery probe (130) attached to, and extending distally away from, mixing chamber (126) of handle (122).

Delivery probe (130) comprises an elongate hollow tube providing a fluid conduit therein, and an orifice (132) at its distal end through which the tissue repair composition is expelled. The proximal end (134) of delivery probe (130) is attached to mixing chamber (126) such that a fluid repair composition may be expelled from mixing chamber (126) into delivery probe (130). In the present example, the distal end (127) of mixing chamber (126) is open, and the proximal end (134) of delivery probe (130) is simply sized to fit snugly over the outer surface of mixing chamber (126) adjacent its distal end (127). The proximal end (134) of delivery probe (130) may be secured to outer surface of mixing chamber (126) using, for example, an adhesive, friction fit, and/or other attachment means. Delivery probe (130) is merely exemplary of one type of delivery device that may be used to deliver the tissue repair composition. Any of the various other delivery devices described herein may be used instead of delivery probe (130), such as end effector (20) shown in FIG. 1.

Figure 10:
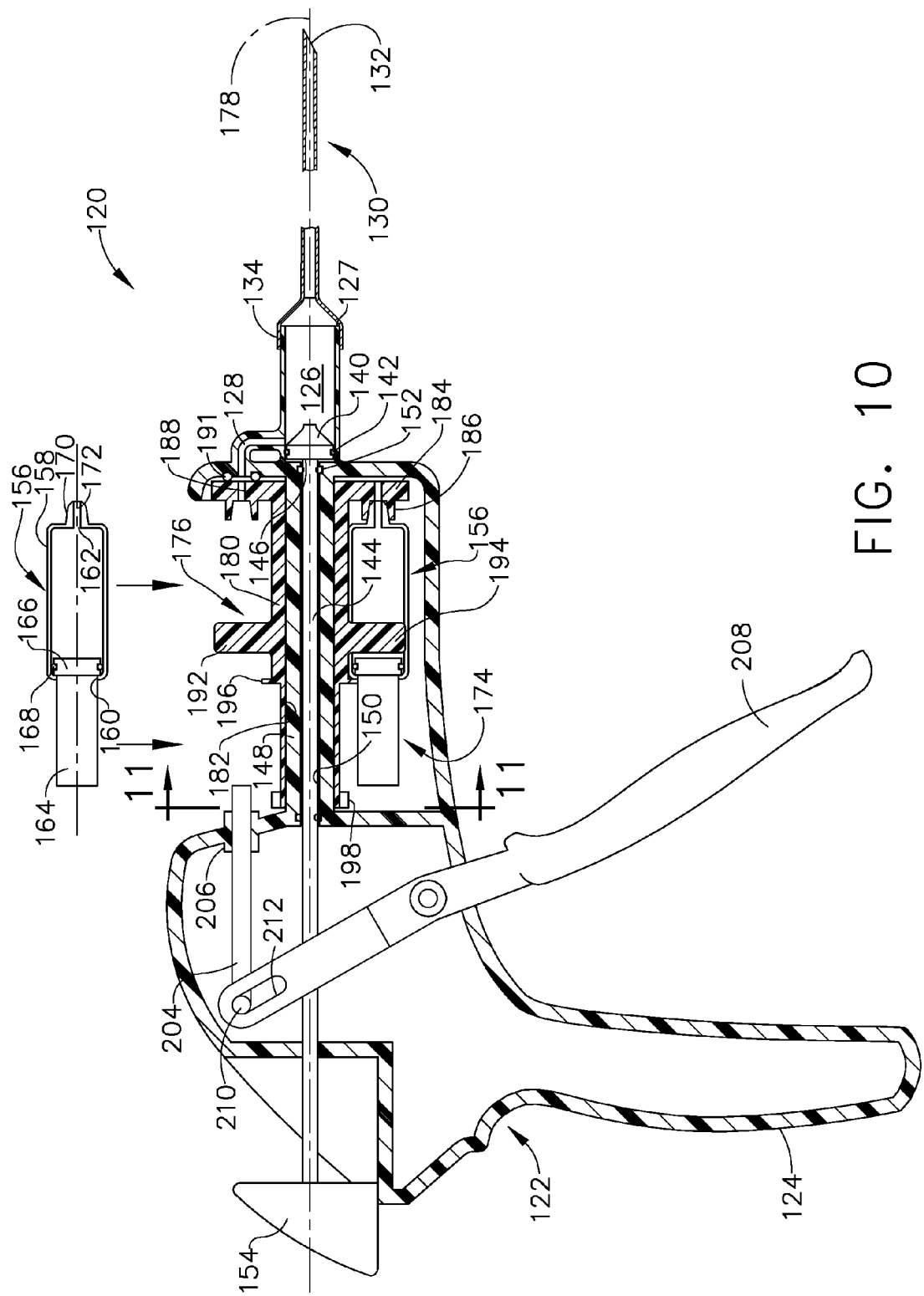
FIG. 10 depicts a partial cross-sectional view of another exemplary lumen repair device.

While tissue repair composition may be expelled from mixing chamber (126) into delivery probe (130) in a variety of ways, the embodiment shown in FIG. 10 uses a pumping device similar to a syringe. Thus, a plunger head (140) is located within cylindrical mixing chamber (126), as shown. An O-ring (142) is provided about the exterior circumference of plunger head (140), and sealingly engages the interior wall of mixing chamber (126). Alternatively, plunger head (140) may be made from a resilient, compressible material, and be shaped so as to snugly, and sealingly fit within mixing chamber (126) (i.e., in a manner similar to the plunger head of a syringe). Plunger head (140) functions similar to the plunger head of a syringe in that, when plunger head (140) is urged in the distal direction (i.e., towards distal orifice (132) of delivery probe (130)), a tissue repair composition within mixing chamber (126) will be expelled from the distal orifice (132).

In order to allow a user to urge plunger head (140) distally so as to expel the tissue repair composition, a push rod (144) extends away from the proximal end surface (146) of plunger head (140). Push rod (144) extends through a cylindrical bore (150) provided in a tubular housing (148) integrally formed in handle (122). Tubular housing (148) extends proximally away from mixing chamber (126), and cylindrical bore (150) within tubular housing (148) communicates with the interior of mixing chamber (126) through an aperture provided in the proximal end wall of mixing chamber (126). Push rod (144) is slidingly received within cylindrical bore (150). O-rings (152) are positioned in circumferential slots extending about the interior circumference of cylindrical bore (150), and the O-rings (150) press against the outer surface of push rod (144) in order to maintain proper alignment of push rod (144) while still allowing axial movement of push rod (144) within cylindrical bore (150) of housing (148). To expel tissue repair composition from mixing chamber (126) into delivery probe (130) and thereafter out of probe (130) through orifice (132), a user forces push rod (144) in the distal direction. Plunger head (140) will be urged distally within mixing chamber (126) in order to expel the tissue repair composition.

In order to facilitate expulsion of the tissue repair composition, an enlarged head (154) is provided at the proximal end of push rod (144). When plunger head (140) is fully retracted (e.g., such that proximal end surface (146) is against the interior proximal end wall of mixing chamber (126)), head (154) extends proximally away from the proximal end of handle (122) above grip (124), as shown in FIG. 10. In this fashion, a user holding can use the thumb of the hand holding grip (124) to push head (154), and hence push rod (144), in the distal direction to expel tissue repair composition from mixing chamber (126).

In order to supply mixing chamber (126) with the various components used to formulate a tissue repair composition or medical fluid in the mixing chamber (126), a plurality of media reservoirs in the form of media cartridges (156) are provided. Media cartridges (156) are similar in construction to the cartridges (60, 90, 94) shown and described above, and are operatively insertable into handle (122) such that flowable media within the cartridges may be selectively and individually supplied to mixing chamber (126) through the fluid conduit (128).

As best seen in FIG. 10, each media cartridge (156) comprises a cylindrical barrel (158) having proximal and distal orifices (160, 162) in the proximal and distal end walls of barrel (158). A plunger (164) extends through the proximal orifice (160) of barrel (158) such that the plunger head (166) is located within barrel (158), as shown. Plunger head (166) is larger in diameter than the proximal orifice (160) such that plunger head (166) will be retained within barrel (158). An O-ring (168) is provided about the exterior circumference of plunger head (166), and sealingly engages the interior wall of barrel (158). Alternatively, plunger head (166) may be made from a resilient, compressible material, and be shaped so as to snugly, and sealingly fit within barrel (158) (e.g., in a manner similar to the plunger head of a syringe). Plunger (164) functions similar to the plunger of a syringe in that, when plunger (164) is urged in the distal direction (i.e., towards distal orifice (162) of barrel (158)), media within cartridge (158) will be expelled from the distal orifice (162). The distal end of cartridge (156) has a male coupling (170) that is cylindrical in shape and has a frustoconical distal tip. As further described herein, male coupling (170) is sized and configured to be snugly received within a female coupling chamber provided in a mounting frame located in handle (122). A fluid conduit (172) extends through the entire length of male coupling (170) and communicates with the interior of barrel (158) through distal orifice (162) in the distal end wall of barrel (158). Like the tissue repair matrix cartridge (94) described previously, when plunger (164) is urged in the distal direction, media within cartridge (156) will be expelled therefrom through fluid conduit (172) of male coupling (170).

Handle (122) of lumen repair device (120) further includes a chamber (174) for alignably and detachably receiving a plurality of media cartridges (156) therein. As shown in FIG.

10, chamber (174) is located proximal to mixing chamber (126), with tubular housing (148) extending axially through the chamber (174). Tubular housing (148) provides an axle about which a cartridge mounting frame (176) is revolvably positioned. Cartridge mounting frame (176) is configured such that a plurality of media cartridges (156) may be detachably mounted to frame (176), with the longitudinal axis of each media cartridge (156) parallel to the longitudinal axis (178) of lumen repair device (120). (Longitudinal axis (178) of lumen repair device (120) extends through the center of push rod (144), the center of tubular housing (148), the central axis of mixing chamber (126), and through the center of delivery probe (130), as shown in FIG. 10.) Once media cartridges (156) are mounted in cartridge mounting frame (176), the frame (176) may be revolved around tubular housing (148) so as to selectively and individually align a media cartridge (156) with fluid conduit (128) in order to allow media contained within the aligned media cartridge (156) to be expelled through fluid conduit (128) into mixing chamber (126).

Cartridge mounting frame (176) comprises a central shaft (180) in which tubular housing (148) is positioned. The interior bore (182) extending through the length of central shaft (180) is sized to receive tubular housing (148) with a close fit that still allows mounting frame (176) to rotate about tubular housing (148). The length of central shaft (180) is slightly less than the length of tubular housing (148) in order to limit longitudinal movement of mounting frame (176) when positioned within chamber (174) of handle (122). A radially extending flange (184) is provided on the distal end of central shaft (180) of cartridge mounting frame (176). A plurality of female couplings (186) extend proximally away from radial flange (184). In the present example, five female couplings (186) are evenly spaced about flange (184). Each coupling (186) comprises a tapered chamber configured to matingly receive the male coupling (170) of a media cartridge (156). A fluid conduit (188) extends from the distal base of the tapered chamber, through the entire thickness of radial flange (184). Couplings (186) are arranged about radial flange (184) such that, as mounting frame (176) is revolved around tubular housing (148), the fluid conduit (188) associated with any one of female couplings (186) may be selectively aligned with inlet (190) of fluid conduit (128) provided in handle (122) (see FIG. 12). An O-ring 191 is provided in a circular groove extending around the distal interior end wall of chamber (174) so as to surround inlet (190). O-ring (191) provides a seal between the distal surface of flange (184) and the distal interior end wall of chamber (174) in the region surrounding inlet (190).

Figure 11:
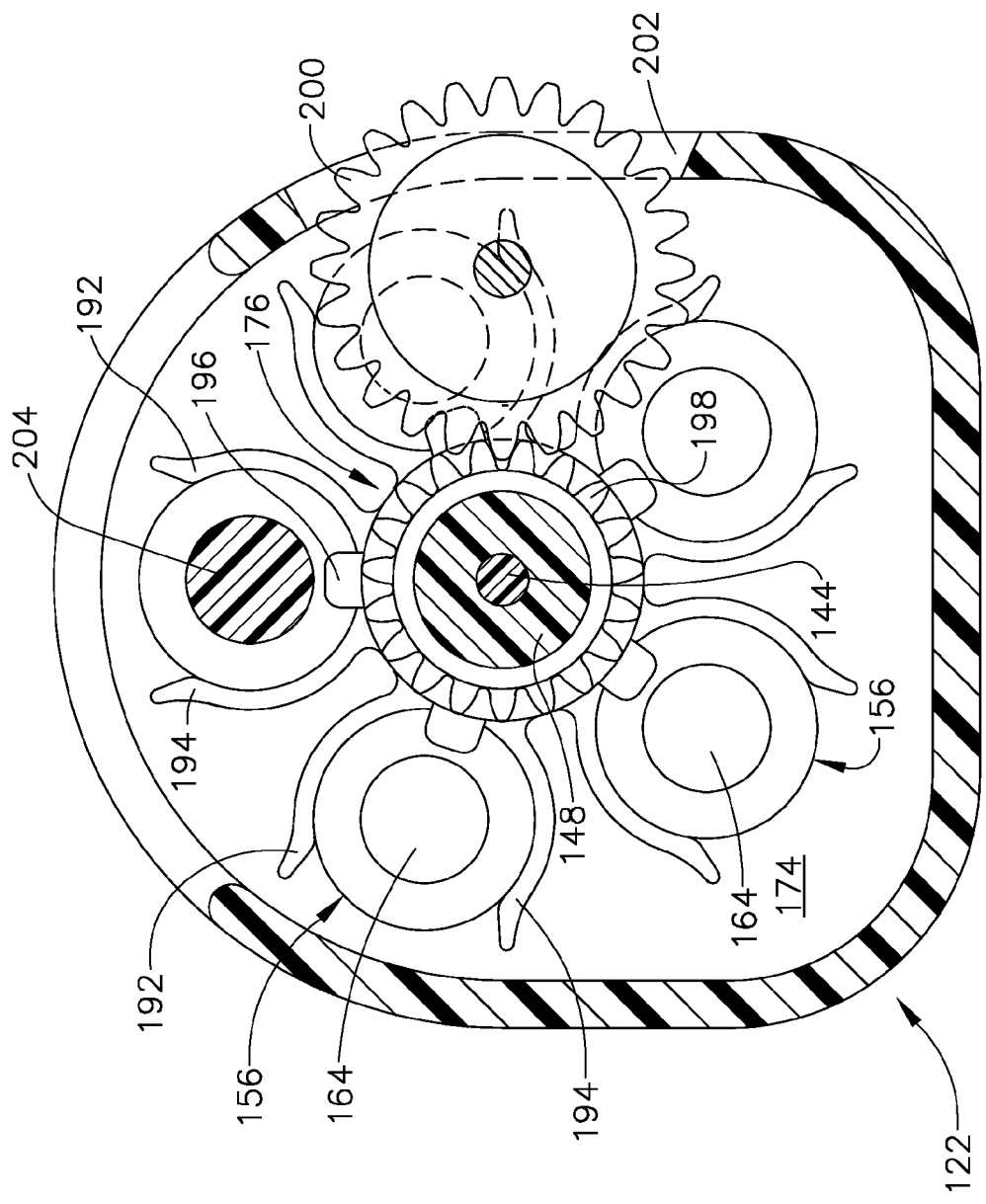
FIG. 11 depicts a cross-sectional view of the lumen repair device of FIG. 10, taken along line 11-11 of FIG. 10.
Figure 12:
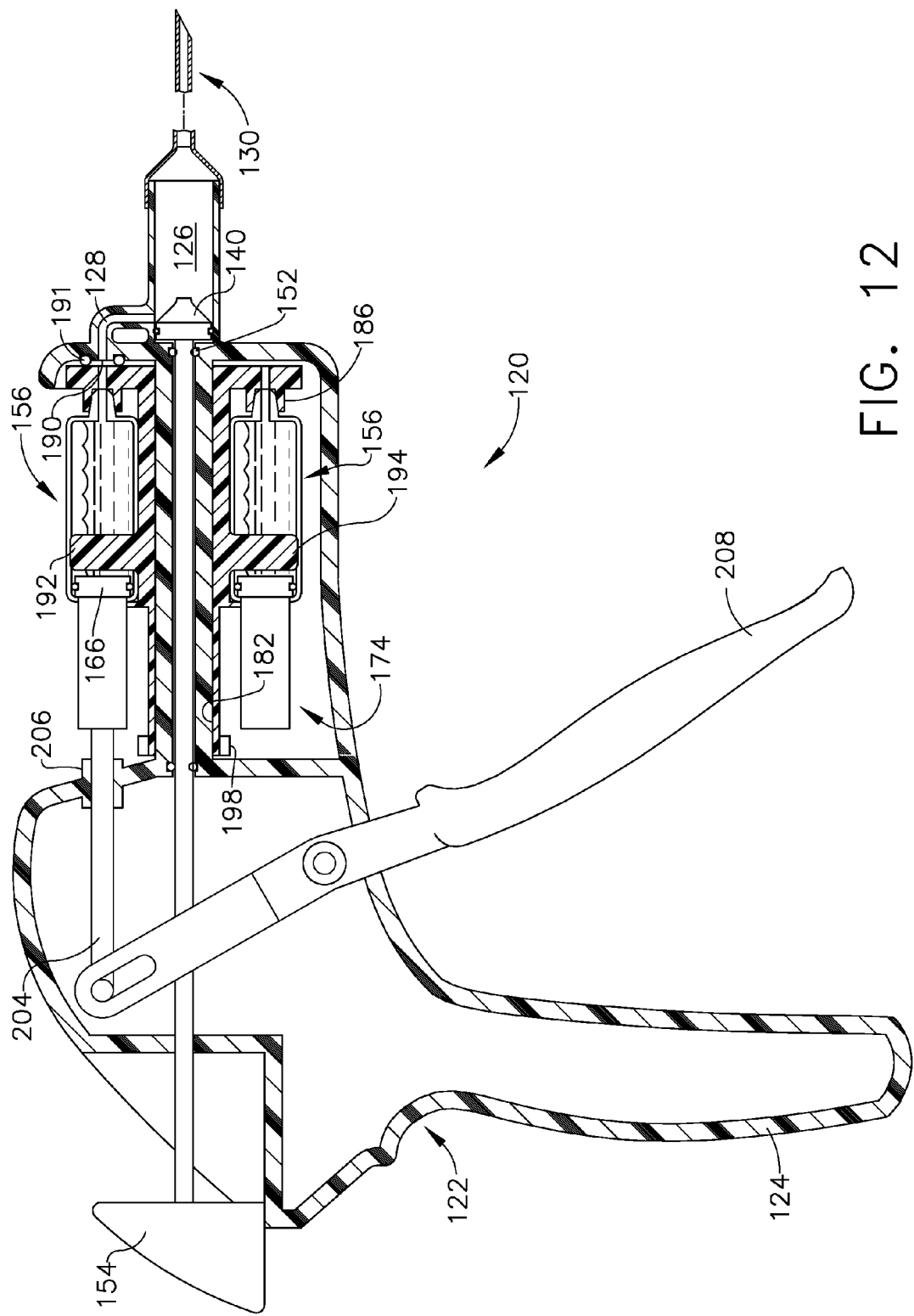
FIG. 12 depicts a partial cross-sectional view of the lumen repair device of FIG. 10, with a plurality of media cartridges installed in the body of the device.

As best shown in FIG. 11, cartridge mounting frame (176) of the present example further includes a plurality of pairs of arcuate fingers (192, 194) which extend curvingly and outwardly away from central shaft (180) of frame (176). Each pair of arcuate fingers (192, 194) define a curved region therebetween for snugly receiving the barrel (158) of a media cartridge (156) in order to mount the media cartridge (156) in the mounting frame (176). A plurality of retention tabs (196) extend radially away from central shaft (180), proximate to arcuate fingers (192, 194). Retention tabs (196) are positioned such that the barrel (158) of a media cartridge (156) may be securely held between a retention tab (196) and a female coupling (186) in which the male coupling (170) of the media cartridge (156) is positioned. Frame (176) may be made from a resilient material such as plastic so that the retention tabs (196) and arcuate fingers (192, 194) may be flexed such that media cartridges may be detachably snap fit into mounting frame (176), as shown.

In order to facilitate revolving movement of cartridge mounting frame (176) about tubular housing (148), a gear (198) is provided on the proximal end of central shaft (180) of frame (176). Thus, as gear (198) is rotated, cartridge mounting frame (176) is revolved around tubular housing (148). In order to further facilitate revolving mounting frame (176) a second drive gear (200) is rotationally mounted within handle (122), in meshing relationship with gear (198) (see FIG. 11). Drive gear (200) may be mounted within handle (122) such that a portion of drive gear (200) extends outwardly of handle (122) through a slot (202) located on a sidewall of handle (122). Thus, the user may revolve cartridge mounting frame (176) by manually rotating drive gear (200) like a thumbwheel. An indexing mechanism (e.g., detent mechanism) may also be provided in order to provide audible and/or tactile feedback to the user when a media cartridge (156) is properly aligned with inlet (190) so that media can be expelled from the aligned cartridge (156) through fluid conduit (128) into mixing chamber (126).

Figure 13:
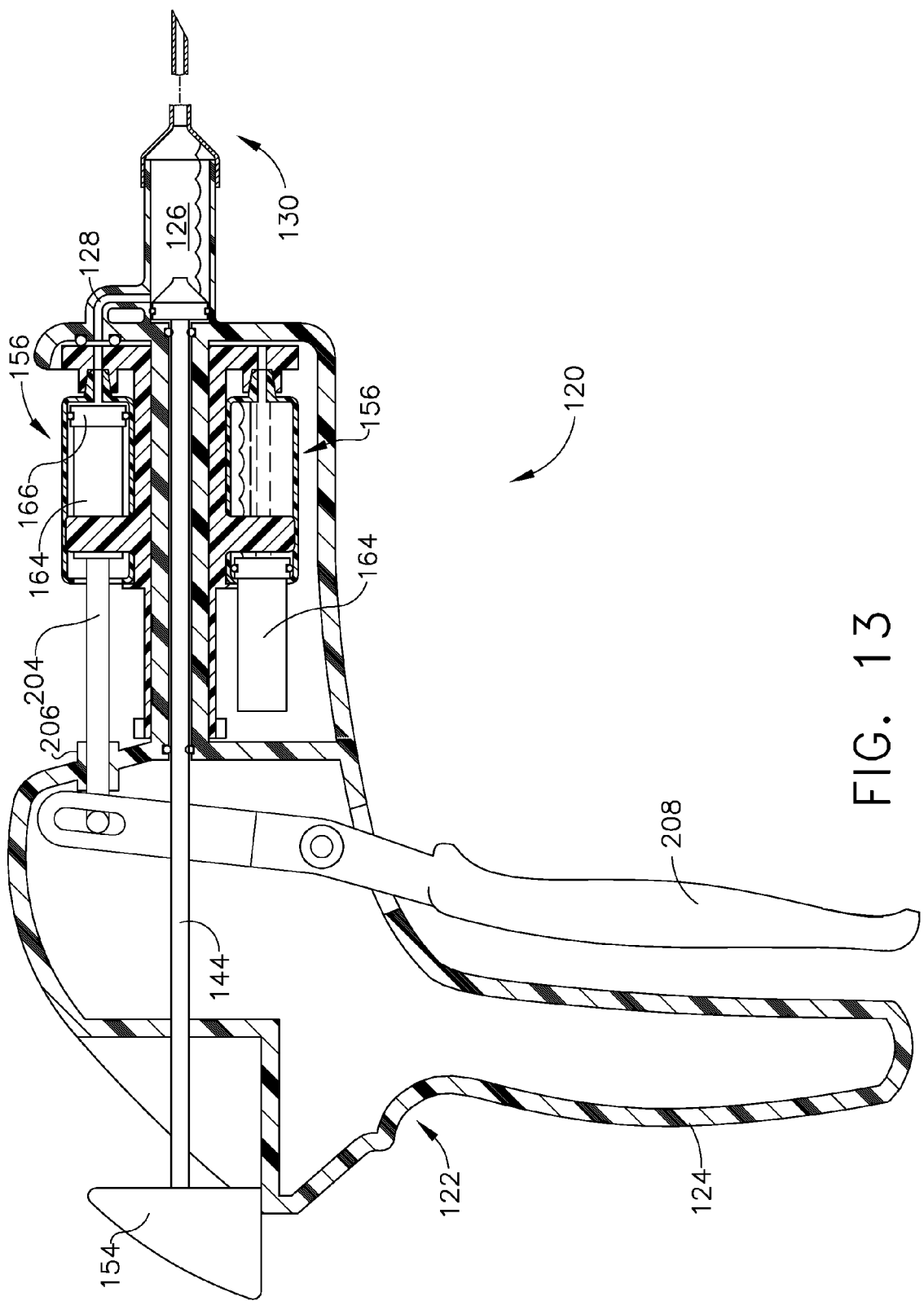
FIG. 13 depicts a partial cross-sectional view of the lumen repair device of FIG. 12, with the contents of one of the media cartridges expelled into the mixing chamber of the device.
Figure 14:
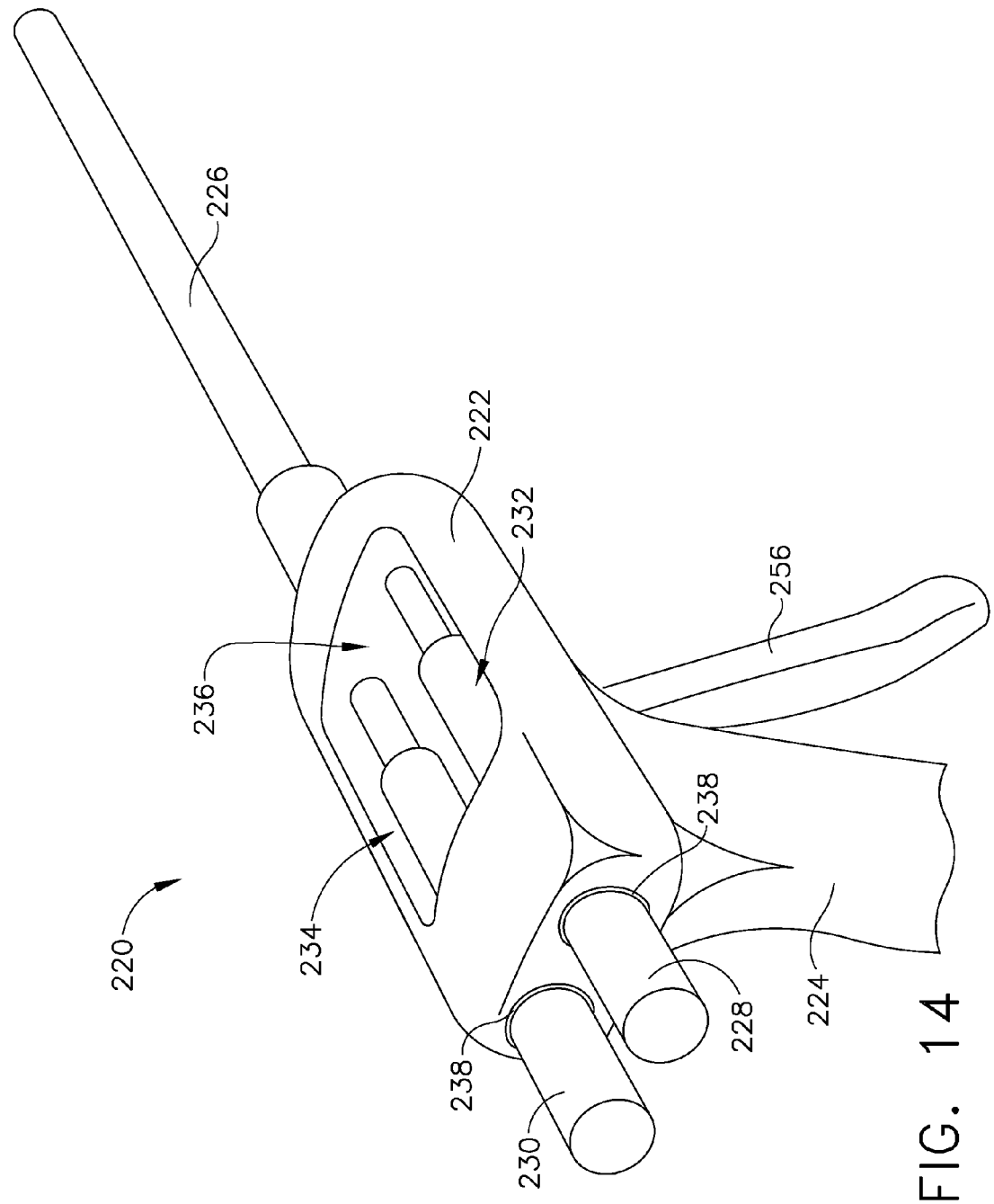
FIG. 14 depicts a partial perspective view of another exemplary lumen repair device.

When a media cartridge (156) mounted in frame (176) is located in the media delivery position (i.e., aligned with inlet (190)), the plunger (164) of the aligned media cartridge (156) may be urged distally in order to expel media from the cartridge into mixing chamber (126). In the present example, a plunger drive member (204) is mounted within handle (122) for sliding, axial movement. Plunger drive member (204) extends through a sleeve (206) located on handle (122) above tubular housing (148). A trigger (208) is pivotally mounted within handle (122) and is in facing alignment with grip (124). The upper end of trigger (208) is attached to drive member (204) by means of a pin (210), which extends laterally away from drive member (204) and is positioned within an elongate slot (212) in the upper end of trigger (208). Thus, when trigger (208) is squeezed towards grip (124), plunger drive member (204) will be urged axially and distally against the proximal end of plunger (164) of a media cartridge mounted in frame (176) located in the media delivery position. As trigger (208) is further squeezed towards grip (124), the contents of the media cartridge (156) will be expelled into mixing chamber (126), as shown in FIG. 13. In some versions, a spring or other type of resilient member is coupled with trigger (208) to bias trigger (208) toward the position shown in FIG. 10. Thus, when a user actuates trigger (208) by squeezing trigger (208) toward grip (124) as shown in FIG. 13, the spring or other resilient member may cause trigger (208) to return to the position shown in FIG. 10 as soon as the user releases trigger (208).

As mentioned previously, lumen repair device (120) may used to formulate and deliver a tissue repair composition to a site in need of repair or other form of treatment such as a fistula. By way of example only, device (120) may be used with one cartridge (156) containing morcellated tissue, with another cartridge (156) containing fibrin, with another cartridge (156) containing saline, and with one or more cartridges (156) containing one or more of the various medical fluid components referred to herein. In use, the user may successively index each cartridge (156) relative to fluid conduit (128) by rotating second drive gear (200). When each cartridge (156) is indexed to fluid conduit (128), the user may squeeze trigger (208) toward grip (124) to empty at least some of the contents of the indexed cartridge (156) into mixing chamber (126), repeating this process until the desired number of cartridges (156) have had contents expelled into mixing chamber (126). The user may then advance head (154) of push rod (144) distally to expel the contents of mixing chamber (126) through probe (130) at the target site in the patient.

Device (120) may be supplied to the end-user with one or more media cartridges (156) already filled with media and/or empty cartridges that are filled by the end-user with the desired media for formulating a tissue repair composition within mixing chamber (126). In some versions, at least one media cartridge (156) is provided to the end user empty so that the user may fill the empty media cartridge (156) with one or more tissue fragments suspended in a suitable carrier (e.g., saline). The tissue fragments may be obtained in any of a variety of ways described herein or known to those skilled in the art. The tissue fragment containing cartridge is then inserted into frame (176) along with the other media cartridges (156) (if not supplied to the end-user already installed in the device (120)). The user then formulates a tissue repair composition by expelling the contents of the media cartridges (156) (including the suspension of tissue fragments) into mixing chamber (126) as described above. A mixing feature such as a rotating impeller may be provided in mixing chamber (126) to facilitate mixing of the media. A fine mesh port (not shown) may also be provided in a side or bottom wall of the mixing chamber (126) to allow excess fluid (e.g., saline) to escape from the mixing chamber (126) prior to delivery of the tissue repair composition. Such a feature may allow for the formulation of a more viscous tissue repair composition that more readily adheres to the interior of the fistula. Thereafter, the formulated tissue repair matrix is delivered to the desired location such as the interior of a fistula via probe (130). Other suitable variations, components, features, configurations, and operabilities of lumen repair device (120) will be apparent to those of ordinary skill in the art in view of the teachings herein.

IV. Exemplary Lumen Repair Device for Formulating and Delivering a Fiber-Containing Tissue Repair Composition Yet another merely illustrative example of a lumen repair device (220) is depicted in FIGS. 14-21. Lumen repair device (220) may be used to prepare a fiber-containing tissue repair composition within the device (220) and deliver that tissue repair composition into a lumen in a patient in order to close, repair, or otherwise treat the lumen. By way of example, device (220) may be used to repair a fistula, such as an anal fistula. Lumen repair device (220) of this example comprises a housing (222) having a handle (224) extending downwardly away from housing (222) adjacent a proximal end of housing (222). An end effector comprising a delivery probe (226) extends distally away from the housing (222). As further described herein, delivery probe (226) has a pair of lumens (i.e., fluid conduits) extending therethrough such that a fiber-containing tissue repair composition as well as a polymer cross-linking solution may be urged through the lumens within delivery probe (226) and expelled from the distal end of probe (226) within a bodily lumen to be repaired. Once delivered into the bodily lumen, the polymer cross-linking solution will cross-link one or more components of the tissue repair composition into a gel or solid material such that the tissue repair composition will fill and be retained in the lumen. The tissue fragments contained in the tissue repair composition will thus be maintained within the lumen, and cells therefrom will integrate with the surrounding cells lining the lumen.

A plurality of media reservoirs comprising media cartridges are insertable into housing (222), and these media cartridges may be similar to those previously described (e.g., comprising a barrel and a plunger for expelling the contents of the cartridge). A pumping device is also provided for expelling the contents of the media cartridges. In the present example and as will be described in greater detail below, the pumping device is provided by a pair of movable frames that selectively drive plungers on media cartridges for expelling the contents of the media cartridges.

In the present example, first and second media cartridges (228, 230) may be removably attached to the proximal end of housing (222), and third and fourth media cartridges (232, 234) may be removably inserted into a cartridge-receiving chamber (236) in housing (222). First cartridge (228) may contain, for example, a solution of one or more cross-linkable, biocompatible proteins such as albumin, casein, fibrin, thrombin, and/or collagen. Second cartridge (230) may contain, for example, a solution of one or more suitable cross-linkers that will cross-link the protein(s) of first cartridge (228) to form a gel or solid. Suitable cross-linkers include, for example, multi-valent iron complexes (e.g., $FeCl_3$), aldehydes, photo-reactive amino acids, or carbodiimides. The cross-linkable protein(s) and cross-linker(s) are combined in a die and extruded therethrough to form microfibrils made of cross-linked protein(s). These mircofibrils are then injected into a tissue fragment-containing matrix having one or more cross-linkable materials such as sodium alginate and carboxymethylcellulose. The thus formulated tissue repair composition is then expelled through delivery probe (226) along with a solution containing one or more cross-linkers for the cross-linkable material(s) in the matrix. Suitable cross-linkers include, for example, a multi-valent calcium complex (e.g., calcium chloride), which cross-links sodium alginate and carboxymethylcellulose. The tissue repair composition and cross-linker solution exit delivery probe (226) separately into the bodily lumen (e.g., fistula), where the cross-linker(s) will coat the tissue repair composition and gel the cross-linkable material in the tissue repair composition to form a semisolid plug that fills the fistula or other lumen being repaired.

Figure 17:
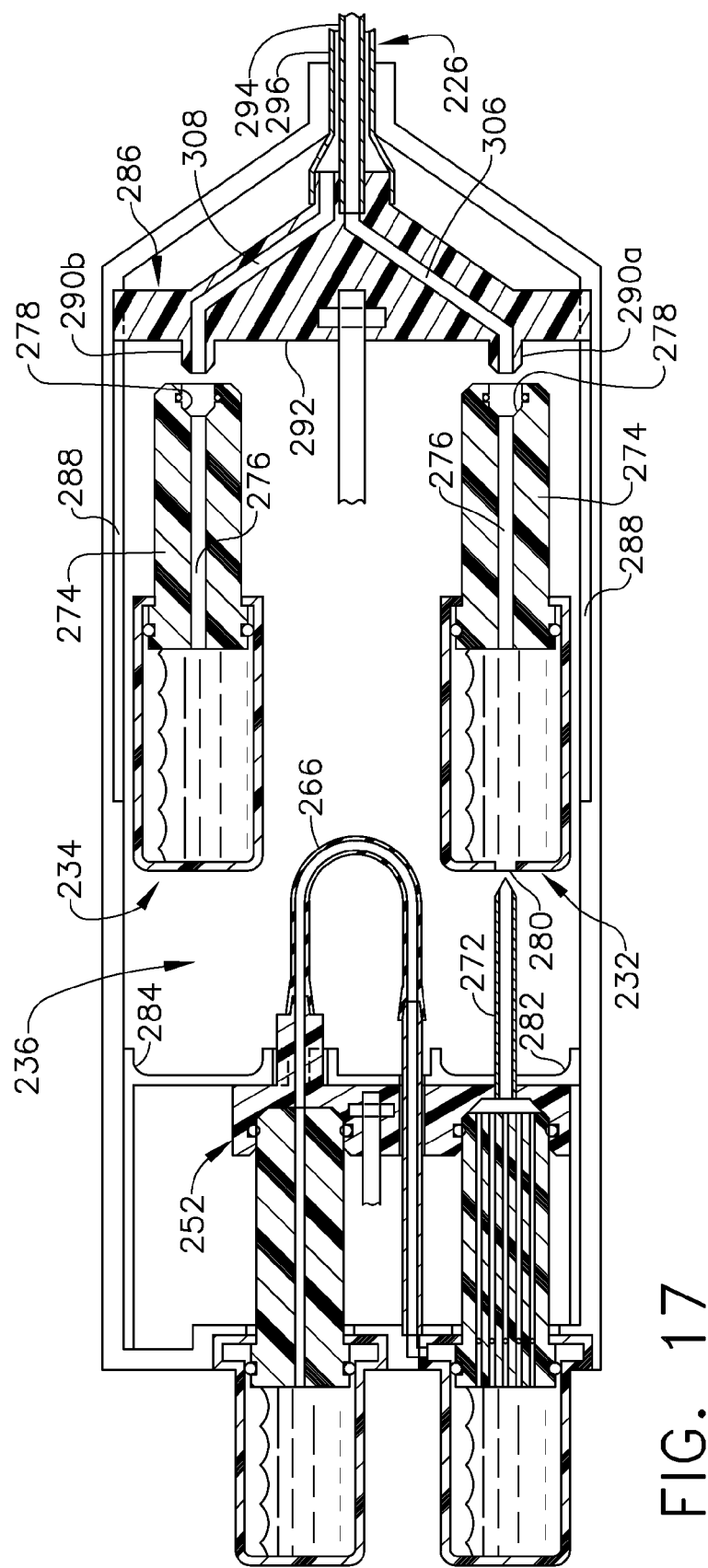
FIG. 17 depicts a partial cross-sectional top view of the lumen repair device of FIG. 14, with two media cartridges installed in the housing of the device, and two additional media cartridges in the process of being installed.

As shown in FIG. 17, first and second media cartridges (228, 230) each have a hollow flange (238) that circumferentially extends about the periphery of the cartridge barrel at one end thereof. Flanges (238) are sized and configured to be mountingly received in first and second mounting cups (243a, 243b) on the proximal end of housing (222), with the plungers (240, 242) of first and second media cartridges (228, 230) extending into housing (222) through apertures provided in the bottom wall of mounting cups (243a, 243b). A fluid conduit (244) extends axially through the length of second plunger (242) of second media cartridge (230), such that when plunger (242) is urged into the barrel of second cartridge (230), media will be expelled from cartridge (230) through fluid conduit (244).

Figure 20:
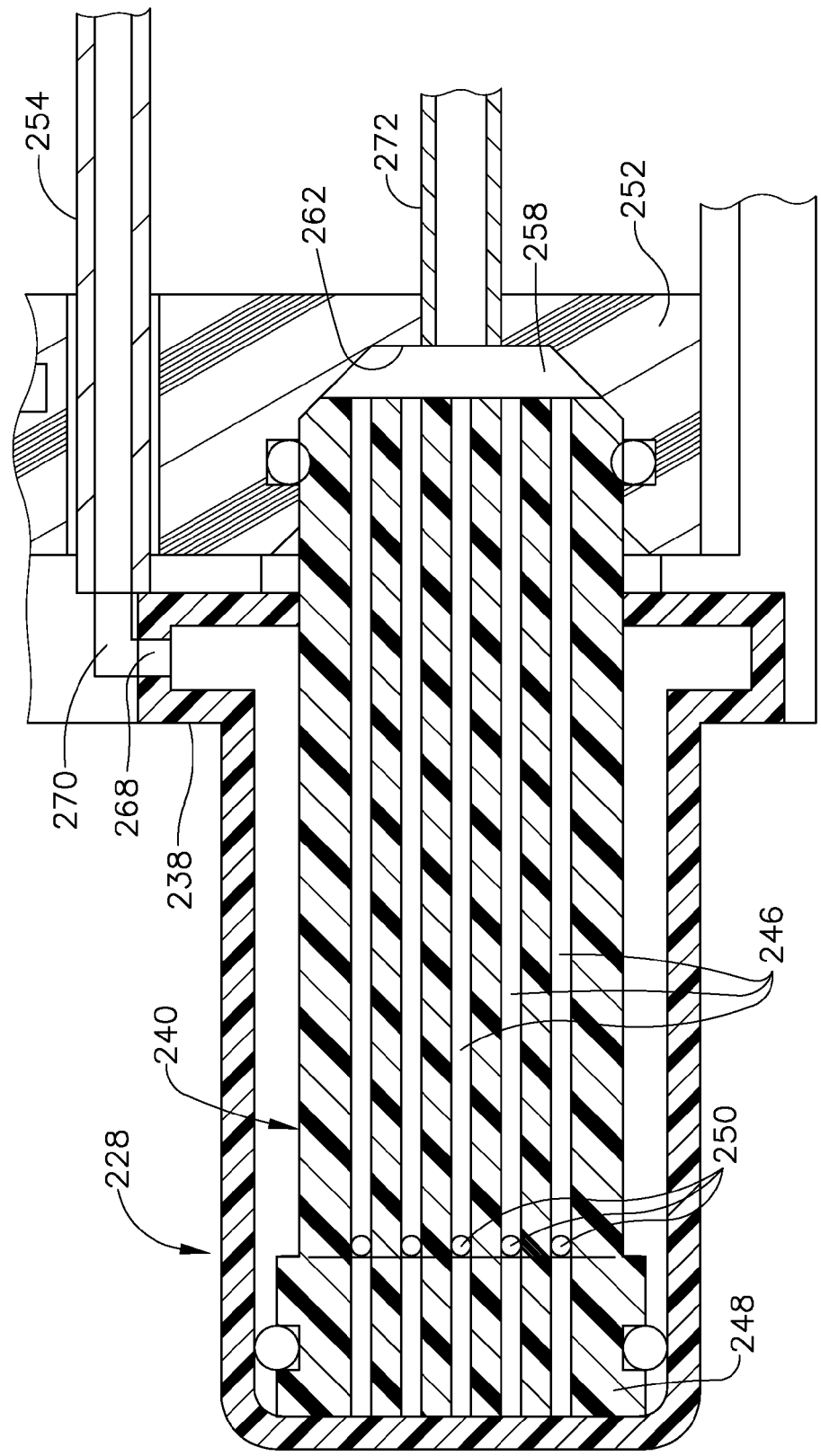
FIG. 20 depicts an enlarged partial cross-sectional view of the first media cartridge installed in the housing of the lumen repair device of FIG. 19, with its contents expelled.
Figure 21:
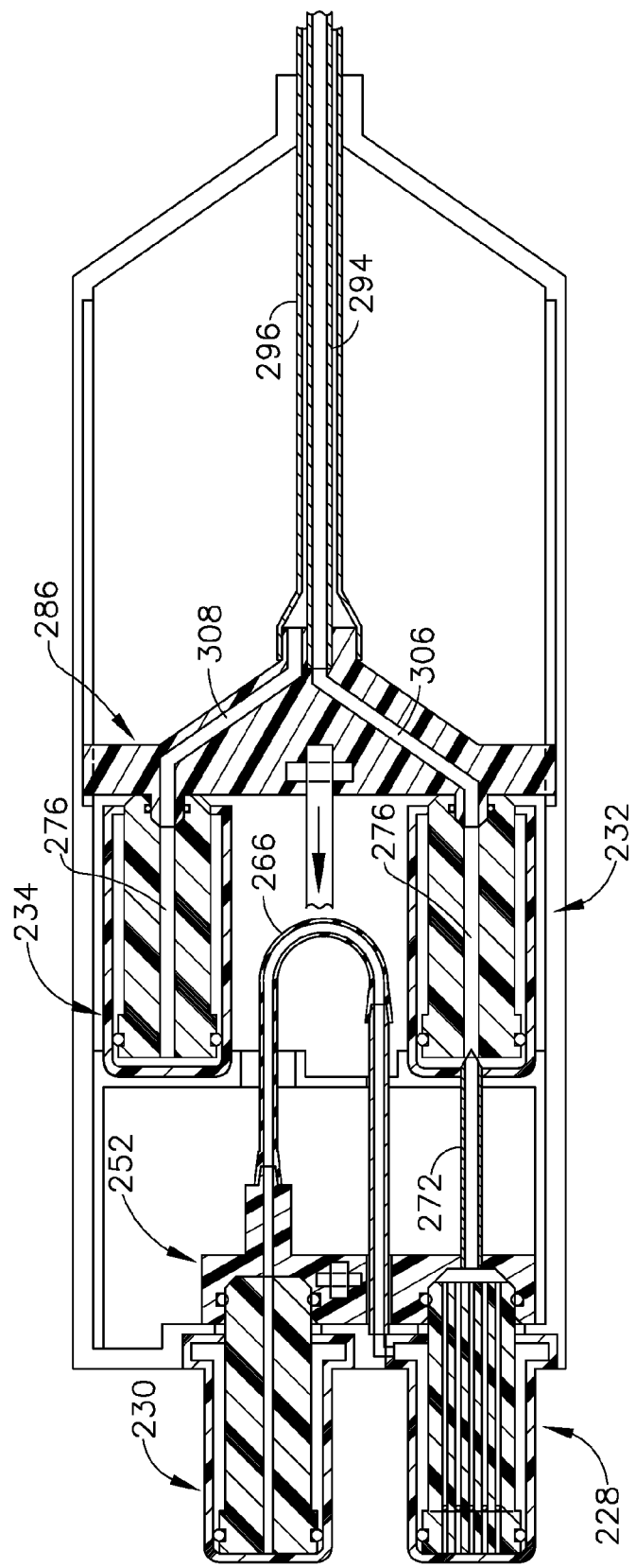
FIG. 21 depicts a partial cross-sectional top view of the lumen repair device of FIG. 19, with the contents of the third and fourth media cartridges expelled from the device.

As best seen in FIG. 20, plunger (240) of first media cartridge (228) includes a plurality of longitudinal passageways (246) that extend lengthwise through plunger (240) such that when plunger (240) is urged into the barrel of first cartridge (228), media will be expelled from cartridge (228) through passageways (246). Plunger (240) also includes an enlarged head portion (248) sealingly positioned in the barrel of first media cartridge (228). A plurality of transverse apertures (250) are also provided in the outer circumference of plunger (240), adjacent the distal base of enlarged head portion (248). Each transverse aperture (250) is in fluid communication with a corresponding passageway (246). As described below, media from second cartridge (230) is urged through apertures (250) into passageways (246) as media in first media cartridge (228) is urged through passageways (246). In this fashion, when the media in second cartridge (230) includes a cross-linker for a protein material in first cartridge (228), cross-linked microfibrils will be formed in passageways (246) in a combined mixing and extrusion process. Thus, passageways (246) in plunger (240) provide a fiber-forming die.

A moveable first frame (252) is provided in housing (222), spaced away from the proximal end wall of housing (222). First frame (252) is slidably movable along a hollow shaft (254), and may be selectively moved proximally towards first and second media cartridges (228, 230) by a trigger (256) or other mechanism or actuator provided on housing (222). First frame (252) includes a first mounting cavity (258) for securely receiving the distal end of plunger (240) of first cartridge (228); and a second mounting cavity (260) for securely receiving the distal end of plunger (242) of first cartridge (230). An aperture (262, 264) extends through the bottom wall of each mounting cavity (258, 260). The aperture (264) in the bottom wall of second mounting cavity (260) is in fluid communication with a cross-linker delivery tube (266), which is also in fluid communication with the interior of hollow shaft (254) on which first frame (252) is slidingly movable. At its proximal end, the interior of hollow shaft (254) is in fluid communication with a port (268), which opens into the sidewall of first mounting cup (243a). Plunger (240) on first media cartridge (228) includes an aperture (270), which may be aligned with port (268) when first cartridge (228) is inserted into first mounting cup (243a). The aperture (262) in the bottom wall of first mounting cavity (258) is in fluid communication with an elongate cannula (272), which extends distally away from first frame (252) into cartridge-receiving chamber (236). The distal tip of cannula is also pointed for penetration of a septum or other seal provided on a proximal end of the barrel of third media cartridge (232).

Figure 18:
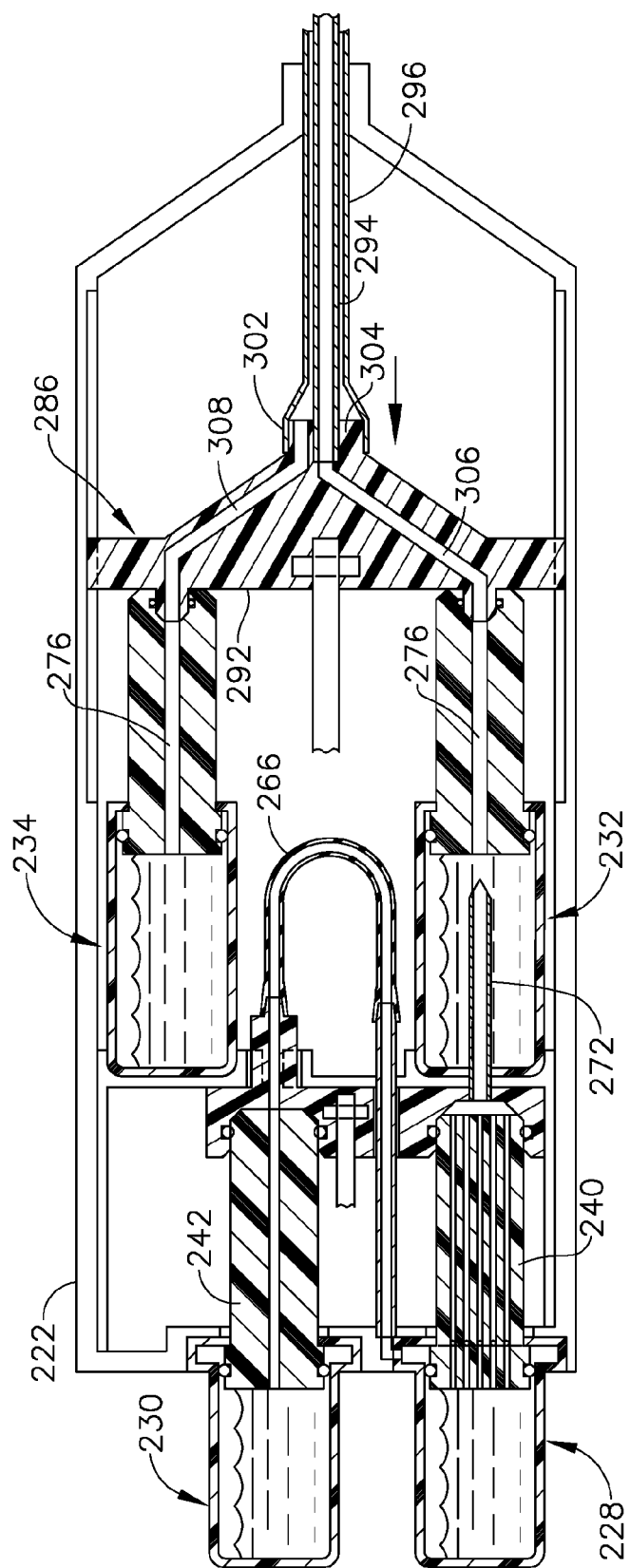
FIG. 18 depicts a partial cross-sectional top view of the lumen repair device of FIG. 17, with four media cartridges installed in the housing of the device.
Figure 19:
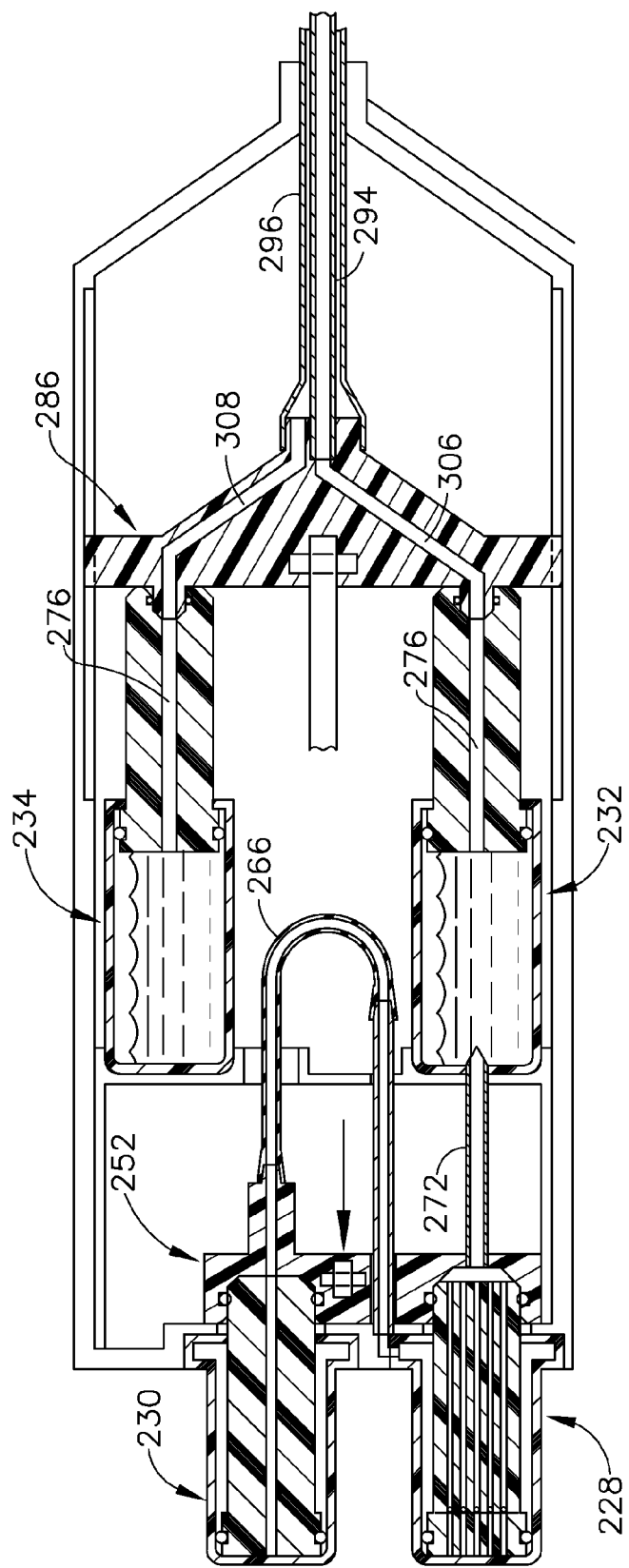
FIG. 19 depicts a partial cross-sectional top view of the lumen repair device of FIG. 17, with the contents of the first and second media cartridges expelled into the third media cartridge.

When first and second media cartridges (228, 230) are mounted on the proximal end of housing (222) as shown in FIG. 18, and first frame (252) is moved proximally along hollow shaft (254) towards first and second media cartridges (228, 230), the bottom walls of first and second mounting cavities (258, 260) will urge plungers (240, 242) proximally into the barrels of the cartridges (228, 230). The cross-linking solution (or other media) in second cartridge (230) will be expelled through cross-linker delivery tube (266) and port (268) into hollow flange (238) of the first media cartridge (228) via aperture (270). At the same time, the protein solution (or other media) will be expelled through the passageways (246) in plunger (240). The cross-linker from second media cartridge (230) will also pass through apertures (250) in plunger (240) into the passageways (246), where the cross-linker will cross-link the protein(s) so as to form microfibrils in passageways (246). These microfibrils will be urged through the passageways into cannula (272), and thereafter into a third media cartridge (232) into which cannula (272) extends (as further described below).

Third and fourth media cartridges (232, 234) may be inserted into cartridge-receiving chamber (236) of housing (222) as shown in FIG. 17. Third and fourth cartridges (232, 234) are similar in construction to tissue fragment cartridge (90) shown in FIG. 7, and thus each include a barrel and a plunger (274) for expelling material from the cartridges (232, 234). A fluid conduit (276) extends through the interior of each plunger (274), from the distal end wall of a female coupling chamber (278), along the longitudinal axis of plunger (274), and through the plunger head. The proximal end wall of fourth cartridge (234) is solid, while the proximal end wall of third cartridge (232) includes a self-sealing septum (280) that may be penetrated by the distal tip of cannula (272).

Cartridge-receiving chamber (236) includes third and fourth cartridge mounts (282, 284) for receiving the proximal ends of third and fourth cartridges (232, 234) therein. Cannula (272) also extends through the bottom wall of third cartridge mount (282). A second movable frame (286) is slidably located in a distal end of cartridge-receiving chamber (236), and is slidably supported by a pair of support rails (288) on opposite sides thereof. A pair of male couplings (290a, 290b) extend away from the proximal end surface (292) of second frame (286). Male couplings (290a, 290b) are configured to be snugly and alignably received within female coupling chambers (278) in the distal end of plungers (274). Thus, male couplings (290a, 290b) are cylindrical, with a frustoconical distal tip such that male couplings (290a, 290b) are snugly received within female coupling chambers (278).

Third and fourth cartridges (232, 234) are inserted into cartridge-receiving chamber (236), with their proximal ends positioned in cartridge mounts (282, 284). As shown in FIG. 18, second frame (286) is then slid proximally until male couplings (290a, 290b) are snugly and alignably received within female coupling chambers (278) in the distal end of plungers (274) on third and fourth cartridges (232, 234).

The end effector comprising delivery probe (226) extends distally away from the housing (222), and comprises an inner tube (294) and an outer tube (296). The inner and outer tubes (294, 296) are coaxial with one another and each terminates in an orifice at the distal end of delivery probe (226). Thus, as best seen in FIG. 16, the inner tube (294) defines a central lumen (298) and an annular outer lumen (300) between outer tube (296) and inner tube (294). A plurality of struts (not shown) may extend between inner tube (294) and outer tube (296) along the lengths thereof in order to maintain a spaced-apart relationship between tubes (294, 296) without preventing flow through both lumens (298, 300). The proximal end (302) of outer tube (296) of delivery probe (226) is flared outwardly for friction fit to a sleeve (304) extending away from the distal end wall of second frame (286). First and second fluid conduits (306, 308) extend through male couplings (290a, 290b) of second frame (286), through the interior of second frame (286), and through sleeve (304). Thus, when a delivery probe (226) is attached to sleeve (304) of second frame (286), first fluid conduit (306) provides fluid communication between the interior of third cartridge (232) and the central lumen (298) of delivery probe (226); and second fluid conduit (308) provides fluid communication between the interior of fourth cartridge (234) and the outer lumen (300) of delivery probe (226).

As mentioned previously, when first frame (252) is slidably moved proximally towards first and second cartridges (228, 230), microfibrils formed within plunger (240) will be urged through cannula (272) into third media cartridge (232). Third media cartridge (232) may contain, for example, one or more tissue fragments suspended in a repair matrix comprising a cross-linkable polymer and any one or more of the various medical fluid components referred to herein. The microfibrils will combine with the tissue fragments and repair matrix to form a tissue repair composition. Thereafter, second frame (286) is urged proximally by, for example, further actuation of trigger (256) or other mechanism or actuator provided on housing (222). In some versions, trigger (256) may be operatively connected to first and second frames (252, 286) such that as trigger (256) is initially squeezed towards handle (224), first frame (252) is urged proximally to form microfibrils and expel the microfibrils into third cartridge (232). Thereafter, trigger (256) is squeezed further towards handle (224) causing second frame (286) to move proximally towards the first and second cartridges (228, 230) to evacuate cartridges (228, 230). In some other versions, trigger (256) is squeezed toward handle (224) in one full stroke to urge first frame (252) proximally to form microfibrils and expel the microfibrils into third cartridge (232); then trigger (256) is squeezed toward handle (224) again in a second full stroke to urge second frame (286) proximally to simultaneously expel the contents of cartridges (232, 234) through delivery probe (226).

It should be understood from the foregoing that proximal movement of second frame (286) causes plungers (274) of third and fourth media cartridges (232, 234) to be urged proximally, expelling the contents of the cartridges into the lumens (298, 300) of the delivery probe (226). The media from third cartridge (232) comprising one or more tissue fragments, a plurality of microfibrils and a cross-linkable polymer is expelled from the distal end of inner tube (294) into a fistula or other lumen as a cylindrical semisolid paste, and the cross-linker solution from fourth cartridge (234) is expelled from the outer lumen (300) of the delivery probe (226) so as to coat the cylindrical paste. The polymer within the cylindrical paste will be cross-linked so as to solidify the paste into a plug structure, and the protein microfibrils and cross-linked polymer will act as a scaffold that supports the tissue fragments within the fistula. Thereafter, the microfibrils and cross-linked polymer will slowly dissolve as cells migrate from the tissue fragments and integrate with the surrounding tissue, thus healing the fistula. Other suitable variations, components, features, configurations, and operabilities of lumen repair device (220) will be apparent to those of ordinary skill in the art in view of the teachings herein.

V. Exemplary Alternative Lumen Repair Device With Mixing Chamber for Formulating a Tissue Repair Composition Another exemplary lumen repair device (320) is shown in the schematic illustration of FIG. 22. Lumen repair device (320) of this example may be used to prepare a tissue repair composition within the device (320) and deliver that tissue repair composition into a lumen in a patient in order to close, repair, or otherwise address the lumen. By way of example, device (320) may be used to repair a fistula, such as an anal fistula. Lumen repair device (320) has a housing that comprises a handle (324), and a mixing chamber (326) movably mounted on handle (324). As further described herein, mixing chamber (326) is mounted on handle (324) such that mixing chamber (326) may be shaken or vibrated in handle (324). By way of example, mixing chamber (326) may be loosely positioned within a housing (not shown) attached to handle (324). An end effector comprising a delivery probe (328) extends distally away from the mixing chamber (326), with a fluid conduit (330) extending longitudinally through delivery probe (328). The fluid conduit (330) of delivery probe (328) is in fluid communication with mixing chamber (326) such that a tissue repair composition medical fluid formulated within mixing chamber (326) may be expelled therefrom through fluid conduit (330) for delivery into a fistula or other site to be addressed. The tissue repair composition is thus expelled through an orifice provided on the distal end of probe (328) within a fistula or other site to be addressed.

Lumen repair device (320) further includes first and second supply reservoirs (332, 334) mounted above mixing chamber (326). Each supply reservoir (332, 334) is configured to contain media comprising one or more components of a tissue repair composition. The media within each supply reservoir (332, 334) may be separately delivered to mixing chamber (326) through first and second supply tubes (336, 338), respectively. First and second supply tubes (336, 338) extend from a distal end of their respective first and second supply reservoir (332, 334) to mixing chamber (326), and provide fluid communication between the supply reservoirs (332, 334) and the interior of the mixing chamber (326). The proximal end of each supply reservoir (332, 334) may be open as shown, with resilient plunger heads (340, 342) sealingly positioned therein. In this manner, media within supply reservoirs (332, 334) may be expelled through supply tubes (336, 338) by urging plunger heads (340, 342) distally (i.e., to the right in FIG. 22).

In order to facilitate expulsion of media from supply reservoirs (332, 334) in mixing chamber (326), a dual plunger arrangement is provided. A plunger handle (344) is connected to first and second plunger heads (340, 342) by plunger rods (not shown), which extend between the proximal end wall of each plunger head (340, 342) and the distal end surface of plunger handle (344). Thus, the contents of each supply reservoir (332, 334) may be simultaneously expelled into mixing chamber (326) by urging plunger handle (344) in the distal direction. Alternatively, separate plunger handles may be provided for each supply reservoir (332, 334) such that the media within the supply reservoirs may be individually delivered to mixing chamber (326).

Figure 22:
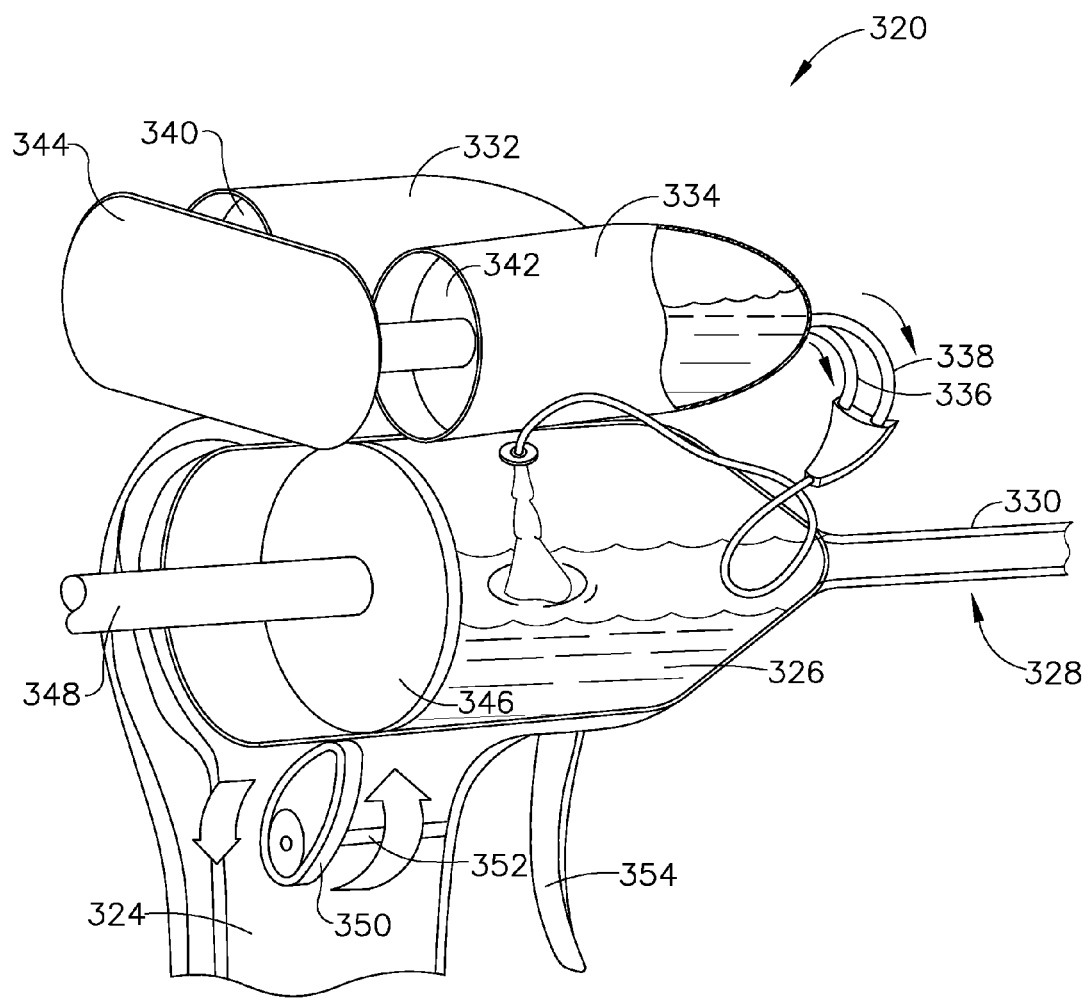
FIG. 22 schematic perspective view of another exemplary lumen repair device.

A pumping device comprising a plunger mechanism is also used to expel a tissue repair composition from mixing chamber (326) through the fluid conduit (330) of delivery probe (328). A resilient plunger head (346) is sealingly positioned within mixing chamber (326), as shown in FIG. 22. A plunger shaft (348) extends proximally away from the proximal end wall of plunger head (346), and may be used to urge plunger head (346) in the distal direction so as to expel a tissue repair composition from mixing chamber (326) into distal probe (328) for delivery into a lumen to be repaired. An enlarged head (not shown) or other member may be attached to the proximal end of plunger shaft (348) in order to facilitate movement of the plunger shaft (348) in the distal direction.

Lumen repair device (320) also includes a mixing feature that shakes or vibrates mixing chamber (326) in order to gently mix the media delivered to mixing chamber (326) from first and second supply reservoirs (332, 334). In the present example, a rotating eccentric cam mechanism similar to a paint mixer is provided. In particular, a rotatable cam (350) is mounted eccentrically on a shaft (352) within handle (324), as shown schematically in FIG. 22. Cam (350) is located beneath mixing chamber (326), adjacent the proximal end of mixing chamber (326). As shaft (352) is rotated (in either direction, or reciprocally), the cam (350) will impinge against the bottom surface of mixing chamber (326) causing an up and down vibratory movement of mixing chamber (326). Such vibratory movement will mix the contents of mixing chamber (326) in order to form a more uniform tissue repair composition. Rotation of shaft (352) and cam (350) may be provided by any number of mechanisms. In the present example shown in FIG. 22, trigger (354) is operatively linked to shaft (352) such that movement of trigger (354) towards handle (324) (such as by squeezing trigger (354) into handle (324)) is translated into rotational movement of shaft (352). Trigger (354) may also be spring-biased away from handle (324) such that cam (350) may be reciprocated back and forth, as shown, by repeatedly squeezing and releasing trigger (354) into and away from handle (324). Such reciprocal rotation of cam (350) will cause the distal end of mixing chamber (326) to bounce up and down in order to mix the contents of the mixing chamber (326), without damaging viable cells therein. In place of a mechanical arrangement for rotating cam (350), a motor may be provided in order to selectively rotate cam (350) for mixing purposes.

Lumen repair device may be supplied to an end-user with one or both of supply reservoirs (332, 334) pre-filled. Alternatively, both supply reservoirs (332, 334) may be empty to allow subsequent filling by the end-user. In one some versions, first supply reservoir (332) may be filled with one or more of the various medical fluid components described herein (e.g., a matrix material, etc.), and second supply reservoir (334) may be filled with a suspension of one or more viable tissue fragments in a biocompatible carrier such as saline. The contents of the supply reservoirs (332, 334) may then be expelled into mixing chamber (326), mixed by vibratory action of rotatable cam (350) to formulate a tissue repair composition, and then expelled into a fistula through delivery probe (328). Delivery probe (328) may be provided in any of a variety of configurations, such as those described herein in conjunction with other examples of lumen repair devices. Other suitable variations, components, features, configurations, and operabilities of lumen repair device (320) will be apparent to those of ordinary skill in the art in view of the teachings herein.

VI. Exemplary Tissue Repair Device with Automated Bioprocessing Module

FIGS. 23-32 depict another exemplary tissue repair device (380). Tissue repair device (380) may be used to deliver a tissue repair composition into a lumen (e.g., an anal fistula) or other site in a patient in order to close, repair, or otherwise address the site. Tissue repair device (380) may also be used to deliver a tissue repair composition to other treatment locations besides fistulas or other lumens, such as anastomosis locations in cancer treatment or gastric bypass surgery, biopsy locations, or any other internal transsection or otomy location. Repair device (380) is similar to lumen repair device (10) shown in FIGS. 1-9 in that it may be used not only to deliver a tissue repair composition to a location in need of repair, but also to harvest one or more tissue specimens, morcellate the tissue specimen(s) to provide viable tissue fragments, and then combine the tissue fragments with various media in order to formulate a tissue repair composition or medical fluid for subsequent delivery to a site in or on a patient.

Figure 23:
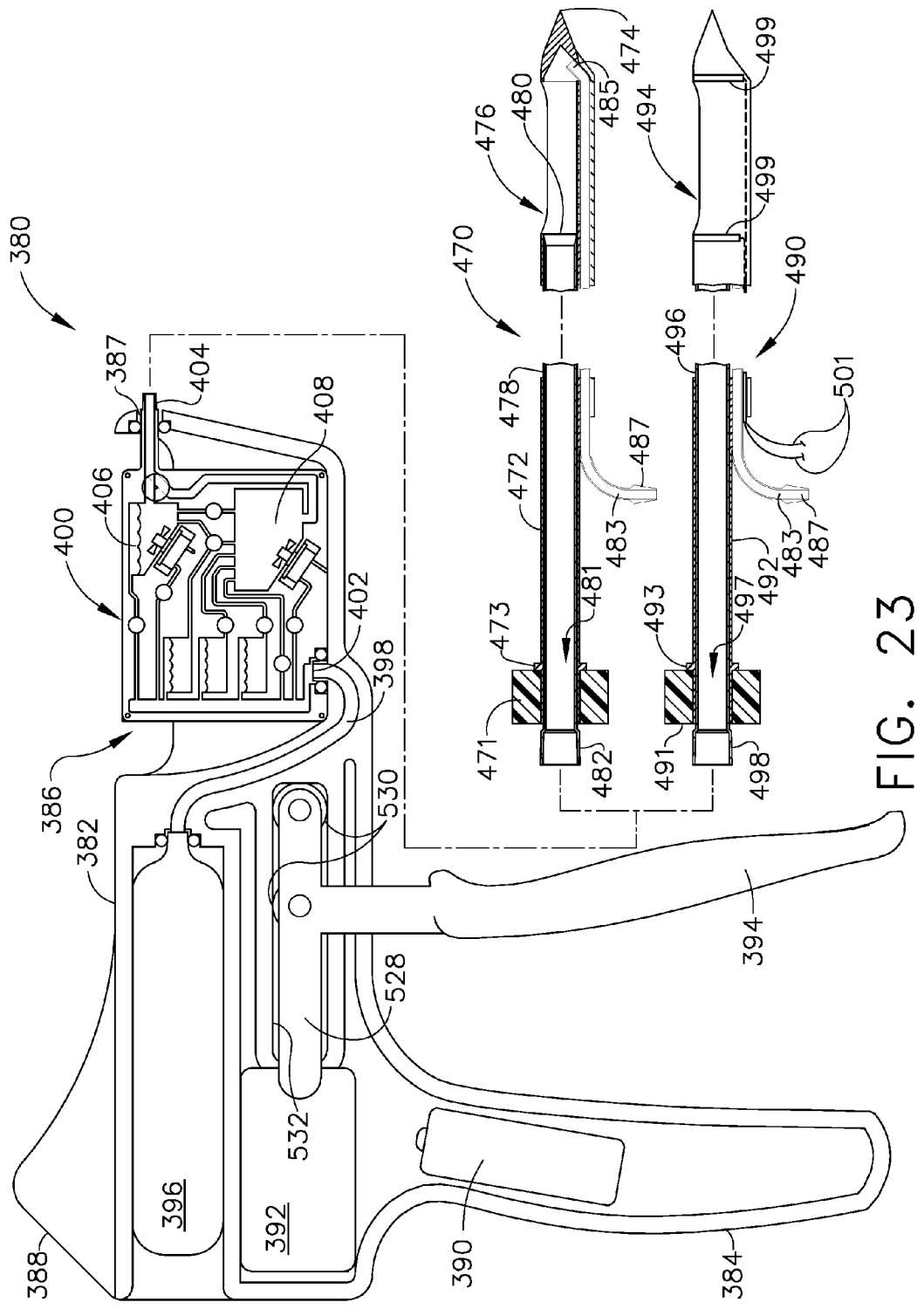
FIG. 23 depicts a partial cross-sectional view of another exemplary lumen repair device, with two different harvesting probes.

As shown in FIG. 23, tissue repair device (380) includes a housing (382) having a handle (384) extending downwardly away from the housing (382). Housing (382) also includes a chamber (386) sized and configured to alignably and securely receive therein a bioprocessing module (400), as further described herein. An end effector is attachable at a distal end of housing (382) so as to extend distally away from housing (382). The tissue repair device (380) of the present example is provided as a kit having a plurality of different end effectors that may be used for different purposes. The end effectors may be removably attached to the housing (382) itself, or, as shown in FIGS. 23-32, removably attached to an outlet port (404) provided on the bioprocessing unit (400). A pumping device, as further described herein, is also provided in order to expel the tissue repair composition.

An LCD display screen (388) is provided at an upper proximal end of housing (382) so as to be easily viewed by an end-user manipulating repair device (380) while holding handle (384). A variety of other types of displays may be used besides an LCD screen. A processing unit (392) is also provided in handle (384), and includes at least one processor (such as a CPU) and at least one memory for providing instructions to the at least one processor. Processing unit (392) functions as a control system for controlling the operation of tissue repair device (380) in accordance with preprogrammed instructions as well as user input. The processing unit (392) is in electrical communication with LCD display (388) in order to cause LCD screen (388) to display various information to an end-user during use of tissue repair device (380). As further described herein, a plurality of input keys are also provided on housing (382) adjacent LCD screen (388), and are in electrical communication with processing unit (392) in order for an end-user to provide input to the tissue repair device (380). A trigger (394) is also provided, and extends downwardly away from housing (382) in facing relationship to handle (384). Trigger (394) is operatively connected to processing unit (392) such that movement of trigger (394) towards handle (384) results in an input signal to processing unit (392). As further described herein, various control elements such as valves and sensors are also in electrical communication with processing unit (392) so that the processing unit (392) may monitor and control operation of repair device (380). Various suitable components, features, and configurations of processing unit (392) will be apparent to those of ordinary skill in the art in view of the teachings herein.

While repair device (380) may be supplied electricity by an external power supply connected thereto, the present example includes a battery (390) located in handle (384). Battery (390) supplies power to LCD display screen (388), processing unit (392), as well as various other components described herein which require electrical power. A pressurized supply of compressed gas is also provided in housing (382), and is used to move and expel various media contained within bioprocessing module (400), as further described herein. In the present example, the pressurized supply of compressed gas comprises a $CO_2$ cartridge (396), and a gas conduit (398) is also included in housing (382), in fluid communication with the interior of $CO_2$ cartridge (396). Of course, compressed gas may be provided in various other ways, including but not limited to an external source coupled via a conduit, a motorized pump, and/or a manually operated device such as a modified syringe or pump.

Figure 24:
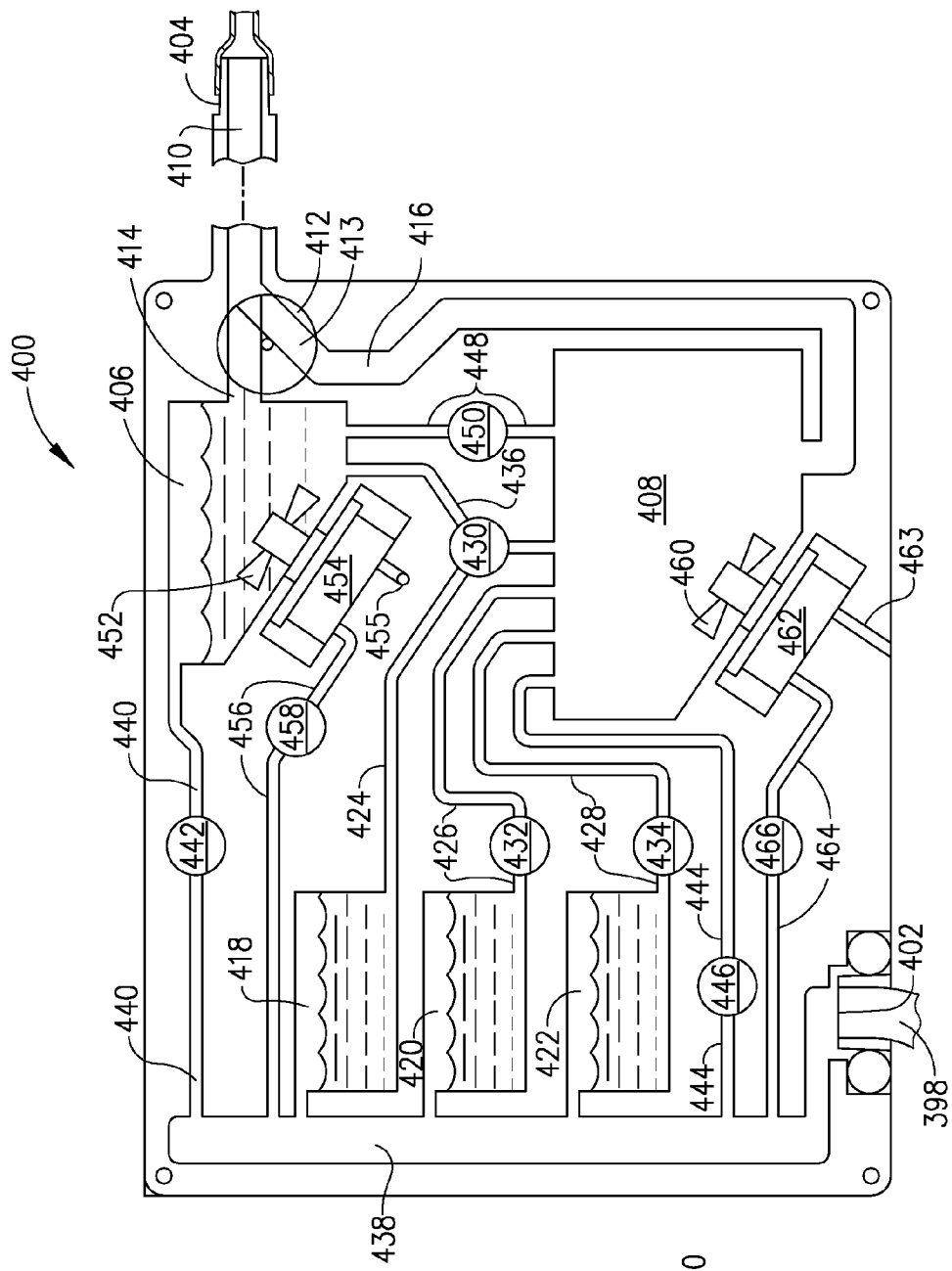
FIG. 24 depicts a schematic cross-sectional view of the bioprocessing module of the lumen repair device of FIG. 23.
Figure 25:
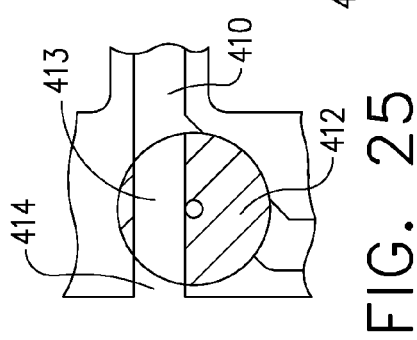
FIG. 25 depicts an enlarged schematic cross-sectional view of a fluid control valve of the bioprocessing module of FIG. 24 in a first position.

Bioprocessing module (400) is shown schematically in FIG. 24, and is configured to be securely, yet detachably positioned within chamber (386) provided in housing (382) of tissue repair device (380). Bioprocessing module (400) may be removably secured within housing (382) by any of a variety of means, such as a by providing a plurality of mounting bosses in housing (382) that are alignably received by corresponding apertures in module (400). Bioprocessing module (400) also includes a plurality of electrical conduits (not shown) such as electrical traces and contacts that are in electrical communication with processing unit (392) when bioprocessing module (400) is properly seated in chamber (386) of housing (382). The electrical conduits transmit power and electrical signals between processing unit (392) and various components of bioprocessing module (400) such as the various valves further described herein. The bioprocessing module (400) also includes a gas inlet (402), which may be sealingly placed in fluid communication with gas conduit (398). An inlet/outlet port (404) is also provided on bioprocessing module (400). Inlet/outlet port (404) is configured and located such that, when bioprocessing module (400) is secured within chamber (386), inlet/outlet port (404) extends outwardly of housing (382) through, and is supported by, a bore (387) extending through a distal end wall of housing (382) adjacent chamber (386).

Figure 26:
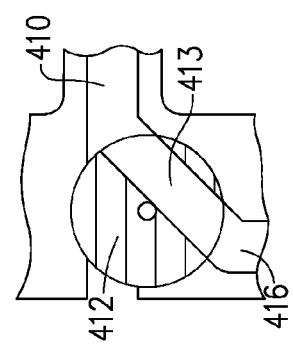
FIG. 26 depicts an enlarged schematic cross-sectional view of a fluid control valve of the bioprocessing module of FIG. 24 in a second position.

As best seen in FIG. 24, bioprocessing module (400) further comprises a morcellating chamber (406) for morcellating one or more soft tissue specimens into viable tissue fragments, and a mixing chamber (408) for combining the viable tissue fragments with fluid media supplied by a plurality of reservoirs in module (400). Morcellating chamber (406) and mixing chamber (408) are in selective fluid communication with main fluid conduit (410), which extends through the interior of inlet/outlet port (404). Thus, a morcellating chamber input conduit (414) is provided in fluid communication with morcellating chamber (406), and a mixing chamber output conduit (416) is provided in fluid communication with mixing chamber (408). Morcellating chamber input conduit (414) and mixing chamber output conduit (416) may each be selectively placed in fluid communication with main fluid conduit (410) via three-way valve (412). Three-way valve (412) may comprise, for example, a three-way ball valve. In the present example, three-way valve (412) includes a rotatable valve body having a fluid passageway (412) extending therethrough. The valve body of valve (412) may be rotated so that fluid passageway (413) provides fluid communication between morcellating input conduit (414) and main conduit (410) (FIG. 25); or between mixing chamber output conduit (416) and main conduit (410) (FIG. 26). The valve body of valve (412) may also be positioned so that no fluid communication is provided therethrough (e.g., fluid communication is only provided through fluid passageway (413)). Valve (412) is selectively positioned by a signal from processing unit (392) delivered to a motor (not shown) or other means for driving the valve body of valve (412).

A plurality of media reservoirs are provided in bioprocessing module (400). In the present example, bioprocessing module (400) has first, second, and third media reservoirs (418, 420, 422), each of which is in selective fluid communication with mixing chamber (408) through first, second, and third reservoir conduits (424, 426, 428), respectively. First, second, and third media valves (430, 432, 434) are provided on first, second and third reservoir conduits (424, 426, 428), respectively, in order to selectively control fluid communication between each media reservoir (418, 420, 422) and mixing chamber (408). Second and third media valves (432, 434) are 2-way valves; while first media valve (430) is a three-way valve. Three-way first media valve (430) may be selectively positioned so as to provide fluid communication between first media reservoir (418) and mixing chamber (408) via first reservoir conduit (424); or between first media reservoir (418) and morcellating chamber (406) via first reservoir conduit (424) and first media delivery conduit (436) extending from first media valve (430) to morcellating chamber (406). Once again media valves (430, 432, 434) are selectively positioned by a signal from processing unit (392) delivered to motors (not shown) or other means for driving each media valve (430, 432, 434) between open and closed orientations. In some other versions, any number of media reservoirs may be provided in bioprocessing module (400), along with a corresponding number of valves for regulating media delivery from the reservoirs. Of course, the number of valves need not necessarily correspond with the number of reservoirs.

Bioprocessing module (400) may be provided to an end-user with first, second and third media reservoirs (418, 420, 422) already filled with a variety of media suitable for formulating a tissue repair composition within mixing chamber (408). In some versions, reservoirs (418, 420, 422) may each comprise a fluid cartridge that may be similar to those previously described with respect to other examples, such that the fluid cartridges may be removably secured to or within bioprocessing module (400). Such an arrangement may allow the end-user to choose the types of media used in formulating a tissue repair composition. One or more of the cartridges may even be provided empty so that an end-user may fill the cartridge with a desired media before the cartridge is removably secured to or within bioprocessing module (400).

While some versions of bioprocessing module (400) may include one or more pumps for moving fluid and delivering a tissue repair composition into a lumen or other site, the repair device (380) of the present example pneumatically drives fluid media using gas from $CO_2$ cartridge (396). Thus, module (400) includes a gas manifold (438) in fluid communication with gas inlet (402), such that pressurized $CO_2$ from cartridge (396) will be provided under pressure in gas manifold (438). Gas manifold (438) is in fluid communication (in some instances, selective fluid communication) with morcellating chamber (406), mixing chamber (408), and media reservoirs (418, 420, 422). In the case of media reservoirs (418, 420, 422), a valve is not provided between gas manifold (438) and the interior volume of the media reservoirs (418, 420, 422) in the present example. In some other versions, one-way check valves may be provided between gas manifold (438) and the media reservoirs (418, 420, 422) in order to prevent fluid media in the reservoirs from entering gas manifold (438). Since the media reservoirs (418, 420, 422) are thus pressurized by $CO_2$ from gas manifold (438), fluid media will be expelled from a reservoir when its corresponding media valve (430, 432, 434) is opened. For example, if third media valve (434) is opened, fluid media will be expelled from third reservoir (428) into mixing chamber (408). During such fluid communication, air within mixing chamber (408) may be vented through mixing chamber output conduit (416), three-way valve (412), and main fluid conduit (410).

A morcellating chamber gas conduit (440) is also provided, and extends between gas manifold (438) and morcellating chamber (406). A valve (442) (e.g., a two-way valve) is provided on morcellating chamber gas conduit (440) in order to provide selective fluid communication between gas manifold (438) and morcellating chamber (406). In this manner, morcellating chamber (406) can be selectively pressurized in order to expel fluid therefrom. Similarly, a mixing chamber gas conduit (444) is also provided, and extends between gas manifold (438) and mixing chamber (408). A valve (446) (e.g., a two-way valve) is provided on mixing chamber gas conduit (444) in order to provide selective fluid communication between gas manifold (438) and mixing chamber (408). In this manner, mixing chamber (408) also can be selectively pressurized in order to expel fluid therefrom. A tissue fragment delivery conduit (448) extends between morcellating chamber (406) and mixing chamber (408) so as to provide fluid communication therebetween. A valve (450) is provided along the tissue fragment delivery conduit (448), so that the fluid communication between the morcellating chamber (406) and the mixing chamber (408) is selective. Thus, fluid or other material, particularly minced tissue fragments suspended in a fluid media, may be moved from morcellating chamber (406) to mixing chamber (408) by opening valve (442) on morcellating chamber gas conduit (440) and valve (450) on tissue fragment delivery conduit (448).

The tissue repair composition delivered by tissue repair device (380) to a fistula or other repair site may comprise one or more viable tissue fragments such as, for example, a muscle tissue specimen acquired from the patient or a donor (autologous, allergenic, and/or xenogenic, etc.) using appropriate harvesting tools. In order to facilitate delivery of the tissue fragments through an end effector of repair device (380), as well as to facilitate migration of viable cells from the tissue fragments, the tissue specimen(s) may be finely minced into small fragments before being provided in mixing chamber (408), where the fragments are combined with other media to form a tissue repair composition. Tissue mincing may be accomplished as the tissue is collected, such as described in U.S. Non-Provisional patent application Ser. No. 12/779,155 entitled "METHODS AND APPARATUS FOR MORCELLATING TISSUE," filed on even date herewith, and published Nov. 17, 2011 as U.S. Pub. No. 2011/0282238, the disclosure of which is incorporated by reference herein. Alternatively, the tissue may be minced after being harvested and collected from a donor (e.g., the patient). Mincing the tissue can be accomplished by a variety of methods, such as by using one or more scalpels or by a processing tool that automatically divides the tissue into particles of a desired size. The viable tissue fragments may then be inserted into morcellating chamber (406) or directly into mixing chamber (408).

In the example shown in FIG. 24, a tissue mincer is provided within the morcellating chamber (406) so that tissue specimens may be minced within the tissue repair device (380). Such a configuration facilitates the processing (e.g., mincing) of viable tissue specimens immediately prior to use, particularly when the tissue specimens are harvested from the patient using tissue repair device (380). In the example shown, the morcellating chamber (406) includes an impeller (452) mounted within the morcellating chamber (406). The impeller (452) has a bladed configuration and is thus configured to mince one or more tissue fragments provided within morcellating chamber (406) so as to cut the tissue fragments into even smaller pieces. In the present example, the impeller (452) is driven by a pneumatic motor (454) provided in bioprocessing module (400). An impeller motor gas conduit (456) provides fluid communication between gas manifold (438) and motor (454), and a valve (458) is provided on impeller motor gas conduit (456) to selectively control the delivery of pressurized $CO_2$ to motor (454). Valve (458), like the other valves described herein, is controlled by a signal from processing unit (392) delivered to valve (458). A vent conduit (455) provides a pressure differential to allow pneumatic motor (454) to be driven by pressurized $CO_2$. Thus, the motor (454) is selectively driven, under control of the processing unit (392), in order to drive the impeller (452) and mince tissue fragments within morcellating chamber (406). In order to facilitate tissue mincing, fluid media (e.g., saline, etc.) may be delivered from first media reservoir (418) into morcellating chamber (406) via first media delivery conduit (436). After mincing, the viable tissue fragments may be expelled from morcellating chamber (406) into mixing chamber (408) via tissue fragment delivery conduit (448).

As an alternative to the motor driven mincer (452) depicted in FIG. 24, any of a variety of other devices and structures suitable for cutting or dividing tissue into smaller fragments may be provided in morcellating chamber (406). Such alternative mincers may be manually or mechanically driven. For example, one or more manually driven cutting blades may be located in the morcellating chamber (406) in order to mince tissue fragments therein. As another merely illustrative example, pneumatic motor (454) may be replaced with an electric motor.

Mixing chamber (408) receives minced, viable tissue fragments from morcellating chamber (406) suspended in a fluid. Various media from the reservoirs (418, 420, 422) are also supplied to mixing chamber (408) in order to formulate a tissue repair composition comprising viable tissue fragments in a tissue repair matrix. For instance, reservoirs (418, 420, 422) may contain any of the various medical fluid components referred to herein, among others. A mixing feature is provided in mixing chamber (408) in order to facilitate mixing of the various components used to formulate the tissue repair composition. In the example shown, a mixing impeller (460) is mounted within the mixing chamber (408). The mixing impeller (460) is configured to blend the tissue fragments and various media within mixing chamber (406) so as to provide a more homogeneous tissue repair composition. In the present example, the mixing impeller (460) is driven by a pneumatic motor (462) provided in bioprocessing module (400). A mixing impeller gas conduit (464) provides fluid communication between gas manifold (438) and motor (462), and a valve (466) is provided on mixing impeller gas conduit (464) to selectively control the delivery of $CO_2$ to motor (462). Valve (466), like the other valves described herein, is controlled by a signal from processing unit (392) delivered to valve (466). A vent conduit (463) provides a pressure differential to allow pneumatic motor (462) to be driven by pressurized $CO_2$. Thus, the motor (462) is selectively driven, under control of the processing unit (392), in order to drive the mixing impeller (460) within mixing chamber (408).

As mentioned previously, tissue repair device (380), may be used not only to deliver a tissue repair composition into a lumen or other site in a patient, it may also be used to harvest one more soft tissue specimens from the patient. The harvested tissue specimens are then morcellated within tissue repair device (380) and used to formulate the tissue repair composition. In order to provide these additional functions, a variety of end effectors configured for operative attachment to tissue repair device (380) are provided. In the present example shown in FIG. 23, two different types of end effectors for harvesting soft tissue specimens are depicted.

First harvesting probe (470) is a side-cutting biopsy probe, and comprises an outer tube (472) having a sharp distal tip (474) configured for penetrating tissue and a transverse tissue receiving port (476) proximal to distal tip (474). A cutting tube (478) is positioned partially within outer tube (472) so as to be longitudinally translatable relative to outer tube (472). Cutting tube (478) has a cutting blade (480) at its distal end. The proximal end (482) of cutting tube (478) extends outwardly away from the proximal end of outer tube (472), and is configured for removable attachment to inlet/outlet port (404) of bioprocessing module (400), as shown. In the example shown, the proximal end (482) of cutting tube (478) is friction fit over inlet/out port (404). Other alternative types of couplings may be employed instead, such as Luer lock fittings.

A block (471) is secured to a proximal flange (473) of outer tube (472), facilitating relative translation between outer tube (472) and cutting tube (478). For instance, with cutting tube (478) being held in a fixed position relative to a patient, a user may grip block (471) and slide it proximally/distally to translate outer tube (472) relative to cutting tube (478). Alternatively, a user may grip block (471) to hold outer tube (472) in a fixed position relative to a patient, then slide cutting tube (478) distally/proximally to translate cutting tube (478) relative to outer tube (472). It should be understood that relative translational movement between cutting tube (478) and outer tube (472) may effectively open and close tissue receiving port (476). When the distal portion of harvesting probe (470) is inserted in a patient, this relative motion may also cause cutting blade (480) of cutting tube (478) to sever a tissue core, which will then be captured in the lumen (481) defined by cutting tube (478). While relative movement between cutting tube (478) and outer tube (472) is provided manually in the present example, it should be understood that such movement may alternatively be provided by an actuation mechanism using any suitable actuation components described as will be apparent to those of ordinary skill in the art in view of the teachings herein.

First harvesting probe (470) of the present example also includes a conduit (483) that extends along outer tube (472). Conduit (483) has a distal port (485) in communication with the interior of outer tube (472) and a proximal port (487). Proximal port (487) is configured to couple with a pressurized medium source (not shown). For instance, proximal port (487) of conduit (483) may be in communication with a pump, a charged air canister, a syringe, etc. The pressurized medium communicated through conduit (483) may comprise air, saline, a medical fluid component, and/or any other suitable type of medium. It should be understood that communication of a pressurized medium through conduit (483) will act on the distal face of a tissue core within cutting tube (478), transporting the tissue core proximally through lumen (481) of cutting tube (478) and ultimately into morcellating chamber (406). Bioprocessing module (400) and/or some other component of tissue repair device (380) may selectively open a vent (not shown) to provide a pressure differential to facilitate proximal transport of tissue through harvesting probe (470) to morcellating chamber (406). It should also be understood that a vacuum may be communicated through conduit (483) to assist in prolapsing tissue through tissue receiving port (476) before the tissue core is severed from the patient and during the severing of the tissue core from the patient. Such a vacuum may be provided by a pump or syringe, etc., coupled with proximal port (487); and may be switched to a pressurized medium after the tissue core has been severed. Of course, first harvesting probe (470) may alternatively have a variety of other components, features, configurations, and/or operabilities.

Second harvesting probe (490) is similar in construction to first harvesting probe (470), and thus comprises an outer tube (492) having a sharp distal tip configured for penetrating tissue, and a tissue receiving port (494) proximal to the distal tip of outer tube (492). A cutting tube (496) is positioned partially within outer tube (492) so as to be longitudinally translatable relative to outer tube (492). Cutting tube (496) has a cutting blade at its distal end. The proximal end (498) of cutting tube (496) extends outwardly away from the proximal end of outer tube (492), and is configured for removable attachment to inlet/outlet port (404) of bioprocessing module (400), as shown. In the example shown, the proximal end (498) of cutting tube (496) is friction fit over inlet/out port (404). Other alternative types of couplings may be employed instead, such as Luer lock fittings.

A block (491) is secured to a proximal flange (493) of outer tube (492), facilitating relative translation between outer tube (492) and cutting tube (496). For instance, with cutting tube (496) being held in a fixed position relative to a patient, a user may grip block (491) and slide it proximally/distally to translate outer tube (492) relative to cutting tube (496). Alternatively, a user may grip block (491) to hold outer tube (492) in a fixed position relative to a patient, then slide cutting tube (496) distally/proximally to translate cutting tube (496) relative to outer tube (492). It should be understood that relative translational movement between cutting tube (496) and outer tube (492) may effectively open and close tissue receiving port (494). When the distal portion of harvesting probe (490) is inserted in a patient, this relative motion may also cause the cutting blade of cutting tube (496) to sever a tissue core, which will then be captured in the lumen (497) defined by cutting tube (496). While relative movement between cutting tube (496) and outer tube (492) is provided manually in the present example, it should be understood that such movement may alternatively be provided by an actuation mechanism using any suitable actuation components described as will be apparent to those of ordinary skill in the art in view of the teachings herein.

Second harvesting probe (490) of the present example also includes a conduit (483) that extends along outer tube (492). Conduit (483) is configured and operable in the same manner as described above with respect to first harvesting probe (470), such that the details of conduit (483) will not be repeated here. Of course, conduit (483) may have any other suitable configuration and/or operability. Second harvesting probe (490) also includes a pair of annular conductive ribbons (499). Conductive ribbons (499) are each circumferentially configured and positioned at each longitudinal end of tissue receiving port (494), within outer tube (492). A respective wire (501) is coupled with each conductive ribbon (499). Wires (501) are in communication with processing unit (392), which is operable to apply a voltage to conductive ribbons (499) and sense the current passing between ribbons (499). With such information, processing unit (392) is further configured to determine the resistance of a material between ribbons (499), such that conductive ribbons (499) and processing unit (392) provide an ohmmeter. It should be understood that such impedance sensing functionality may provide tissue sensing capabilities to determine whether and how much tissue is prolapsed through tissue receiving port (494). In some versions, such information is used to provide feedback to the user via LCD display (388) (e.g., to indicate to the user that sufficient tissue is prolapsed, prompting the user to actuate outer tube (492) and/or cutting tube (492) to sever the prolapsed tissue, etc.). Alternatively, the presence and/or amount of tissue may be sensed in any other suitable fashion, and such information may be used in any other suitable way. Other suitable components, features, configurations, and/or operabilities for second harvesting probe (490) will be apparent to those of ordinary skill in the art in view of the teachings herein.

Once either first or second harvesting probe (470, 490) is operatively attached to the inlet/outlet port (404) of bioprocessing module (400), the harvesting probe (470, 490) may be used to harvest one or more soft tissue specimens. The soft tissue specimens are communicated proximally through harvesting probe (470, 490) and into morcellating chamber (406) as described above. The tissue may then be morcellated within morcellating chamber (406) as described above. In some other versions, tissue is harvested in some other fashion and/or communicated to morcellating chamber (406) in some other fashion. Furthermore, bioprocessing module (400) may be provided pre-loaded with un-minced tissue that is minced in morcellating chamber (406) just before use; or even with already minced tissue such that tissue does not need to be minced in morcellating chamber (406). Ultimately, minced tissue may be mixed in mixing chamber (408) as described above to provide a medical fluid or tissue repair composition.

Figure 27:
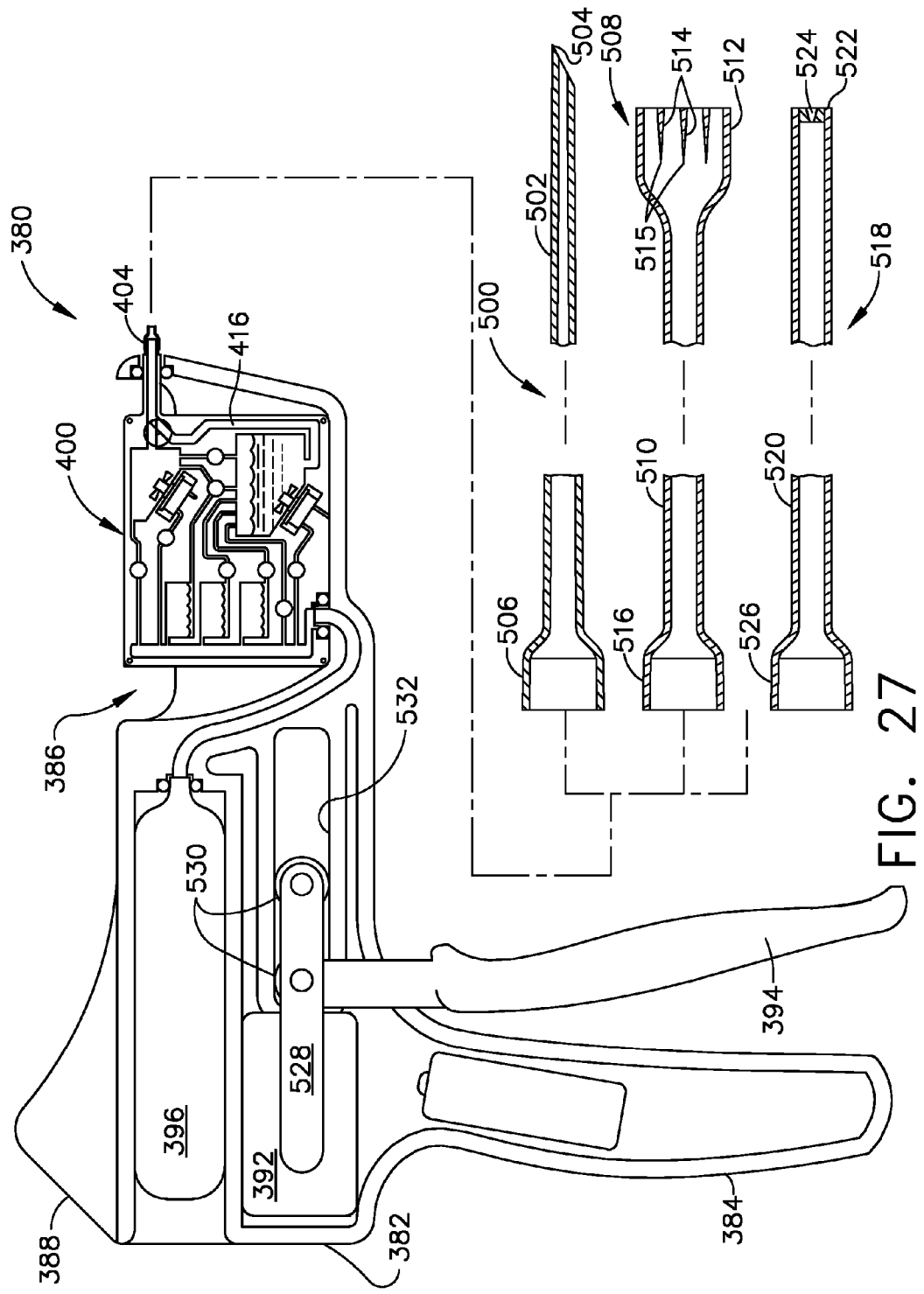
FIG. 27 depicts a partial cross-sectional view of the lumen repair device of FIG. 23, with three different delivery probes.

In order to deliver a tissue repair composition from mixing chamber (408) into a lumen (e.g., a fistula) or other site to be repaired or otherwise addressed, an end effector for delivering the tissue repair composition may be attached to the repair device (380). FIG. 27 depicts three exemplary types of delivery probes that are removably attachable to inlet/outlet port (404) on bioprocessing module (400). First delivery probe (500) comprises an elongate tube (502) defining a fluid conduit therein. Tube (502) has a sharp distal tip (504) and a proximal end portion (506) configured to be matingly received on inlet/outlet port (404) of the module (400). The proximal end portion (506) of tube (502) is friction fit over inlet/out port (404). Other alternative types of couplings may be employed instead, such as Luer lock fittings. When first delivery probe (500) is thus attached to inlet/outlet port (404), a tissue repair composition may be expelled from mixing chamber (408) through mixing chamber output conduit (416), through inlet/outlet port (404), and into the elongate, hollow tube (502) of the first delivery probe (500). The tissue repair composition will be expelled out of the orifice provided at the distal end of tube (502) for delivery to the desired location.

Second delivery probe (508) shown in FIG. 27 comprises an elongate tube (510) having a proximal end portion (506) configured to be matingly received on inlet/outlet port (404) of the module (400) similar to first delivery probe (500). Thus, the proximal end portion (506) of tube (502) is friction fit over inlet/out port (404). Other alternative types of couplings may be employed instead, such as Luer lock fittings. The distal end portion (512) of the tube (510) of second delivery probe (508) is enlarged compared to the size of tube (510) located between the proximal and distal end portions (512, 516) thereof. In addition, a plurality of tapered fins (514) extend laterally across the interior of distal end portion (512), and each fin (514) includes a tapered proximal end (515). When a tissue repair composition comprising one or more viable tissue fragments is expelled from the distal end of tube (510) of second delivery probe (508), the fins (514) may further mince the tissue fragments and/or mix the medical fluid as it is being expelled. In addition, the flared distal end portion (512) will allow the user to more easily spread the tissue repair composition over a surface.

Third delivery probe (518) shown in FIG. 27 comprises an elongate tube (520) having a proximal end portion (526) configured to be matingly received on inlet/outlet port (404) of the module (400), similar to first and second delivery probes (500, 508). Thus, the proximal end portion (526) of tube (520) is friction fit over inlet/out port (404). Other alternative types of couplings may be employed instead, such as Luer lock fittings. The distal end (522) of the tube (520) of third delivery probe (518) includes a nozzle (524) mounted therein. Nozzle (524) is configured such that a tissue repair composition urged therethrough will be expelled from the distal end (522) of tube (520) as a spray.

In the example shown in FIG. 27, in order to expel a tissue repair composition through a delivery probe attached to module (400), the user may simply squeeze trigger (394) towards handle (384). A lever (528) is attached to the upper end of trigger (394), and is supported by a pair of wheels (530) rotatably attached to lever (528) and rollingly supported within an elongate slot (532). As trigger (394) is squeezed towards handle (384), the movement of trigger (394) is translated to longitudinal movement of lever (528) away from bioprocessing module (400) within housing (382). In other words, trigger (394) translates relative to handle (384) rather than pivoting relative to handle (384) in this example. Lever (528) is operatively connected to processing unit (392) such that the longitudinal movement of lever (528) causes processing unit (392) to generate one or more signals that result in tissue repair composition being expelled from mixing chamber (408) into the delivery probe. In this fashion, trigger (394) provides a user input instructing the processing unit (394) to cause tissue repair composition to be delivered to a lumen or other repair site through the delivery probe attached to the repair device (380). Of course, trigger (394) is just one example of an input to effect dispensation of the medical fluid from mixing chamber (408) through the delivery probe. Any other suitable type of user input may be used in addition to or in lieu of trigger (394).

FIGS. 28-32 depict an exemplary alternative version of a bioprocessing module (540), which may be removably securable within a chamber (386) provided in housing (382) of tissue repair device (380). Bioprocessing module (540) may be used in place of bioprocessing module (400), and is similar thereto in construction. Bioprocessing module (540) differs from bioprocessing module (400) in that it is configured for use with dual lumen delivery probes; and it includes a fourth media reservoir (542). The same harvesting probes may be used with bioprocessing module (540), while in other examples the proximal end portions of the harvesting probes are modified slightly to better fit the dual lumen inlet/outlet port (544) on bioprocessing module (540).

Figure 29:
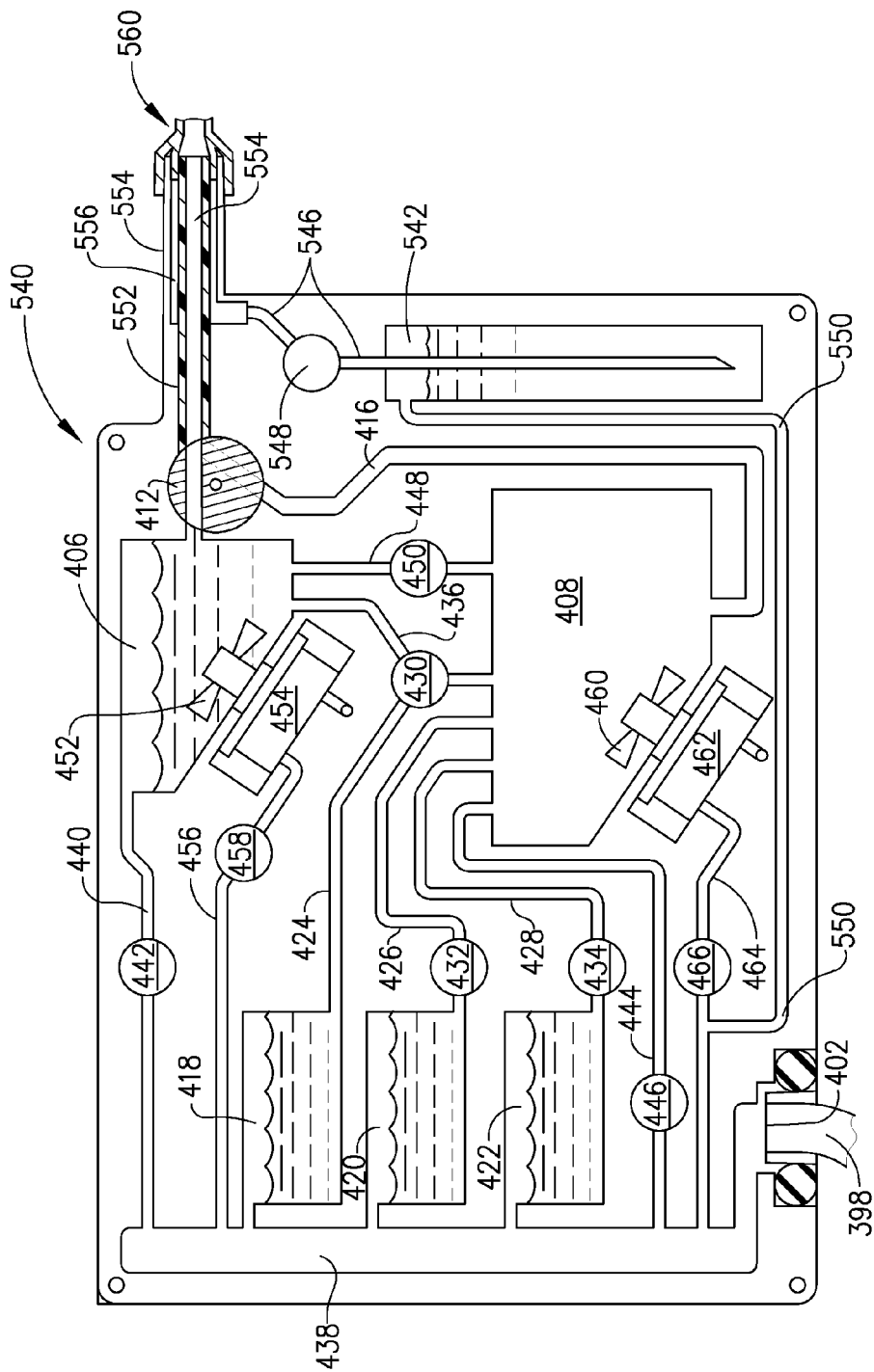
FIG. 29 depicts a schematic cross-sectional view of the bioprocessing module of the lumen repair device of FIG. 28.

As best seen in FIG. 29, in addition to the structures and features described previously with respect to bioprocessing module (400), bioprocessing module (540) also includes a fourth media reservoir (542) in selective fluid communication with dual lumen inlet/outlet port (544) through fourth reservoir conduit (546). A fourth media valve (548) is provided on fourth reservoir conduit (546) in order to selectively control fluid communication between fourth media reservoir (542) and inlet/outlet port (544). As before, fourth media valve (548) is selectively positioned by a signal from processing unit (392) delivered to motors (not shown) or some other means for driving the media valve (548) between open and closed orientations. Fourth media reservoir (542) may contain any of the various medical fluid components referred to herein. By way of example, fourth media reservoir (542) may contain a medical fluid similar to that contained in one or more of the other media reservoirs (418, 420, 422) but at a different concentration (e.g., to increase or decrease fragment/collagen concentrations, etc.). As yet another alternative example, fourth media reservoir (542) may contain one or more healing agents, such as biological components (e.g., growth hormone, etc.) that accelerate healing and/or tissue regeneration healing.

Fourth media reservoir is in fluid communication with gas manifold (438) through an additional gas conduit (550), which communicates with gas manifold (438) through mixing impeller gas conduit (464) as shown in FIG. 29. Since the fourth media reservoir (542) is thus pressurized by $CO_2$ from gas manifold (438), fluid media will be expelled from fourth reservoir (542) through fourth reservoir conduit (546) when its corresponding media valve (548) is opened. Unlike the first, second and third media reservoirs (418, 420, 422), fourth media reservoir (542) is configured to expel media into the outer lumen of dual lumen inlet/out port (544), rather than into mixing chamber (408). Thus, the tissue repair composition from mixing chamber (408) and the media from fourth reservoir (542) may be delivered separately through a dual lumen delivery probe and combined with one another just prior to, or at the same time as, the tissue repair composition and additional media exit the distal end of the delivery probe. Such an arrangement may be desirable, for example, when the media in fourth reservoir (542) will interact with one or more of the components of the tissue repair composition delivered from mixing chamber (408), and therefore it may be appropriate to limit such interaction to within or at the treatment location.

Bioprocessing module (540) may be provided to an end-user with first, second, third and fourth media reservoirs (418, 420, 422, 546) already filled with a variety of media suitable for formulating a tissue repair composition within mixing chamber (408) and delivery of the tissue repair composition with the media from fourth media reservoir (542) to a repair site. In some other versions, reservoirs (418, 420, 422, 546) may each comprise a fluid cartridge that may be similar to those previously described with respect to other embodiments, such that the fluid cartridges may be removably secured to or within bioprocessing module (540). Such an arrangement may allow the end-user to choose the types of media used in formulating a tissue repair composition. One or more of the cartridges may even be provided empty so that an end-user may fill the cartridge with a desired media before the cartridge is removably secured to or within bioprocessing module (540).

As mentioned above, inlet/outlet port (544) on bioprocessing module (540) differs from the inlet/outlet port on bioprocessing module (400) in that inlet/outlet port (544) has a pair of concentric lumens. Inlet/outlet port (544) includes a central tube (552) defining a main fluid conduit (or lumen) (554) therein. Main conduit (554) is similar to main conduit (410) of bioprocessing module (40). Thus, main conduit (554) is configured such that morcellating chamber input conduit (414) and mixing chamber output conduit (416) may each be selectively placed in fluid communication with main fluid conduit (554) via three-way valve (412). Inlet/outlet port (544) also includes an outer tube (556) in which central tube (552) is positioned such that an annular lumen is provided between the inner wall of outer tube (556) and the outer wall of central tube (552). This annular lumen of inlet/outlet port (544) is in fluid communication with the fourth reservoir conduit (546), as shown in FIG. 29.

Figure 28:
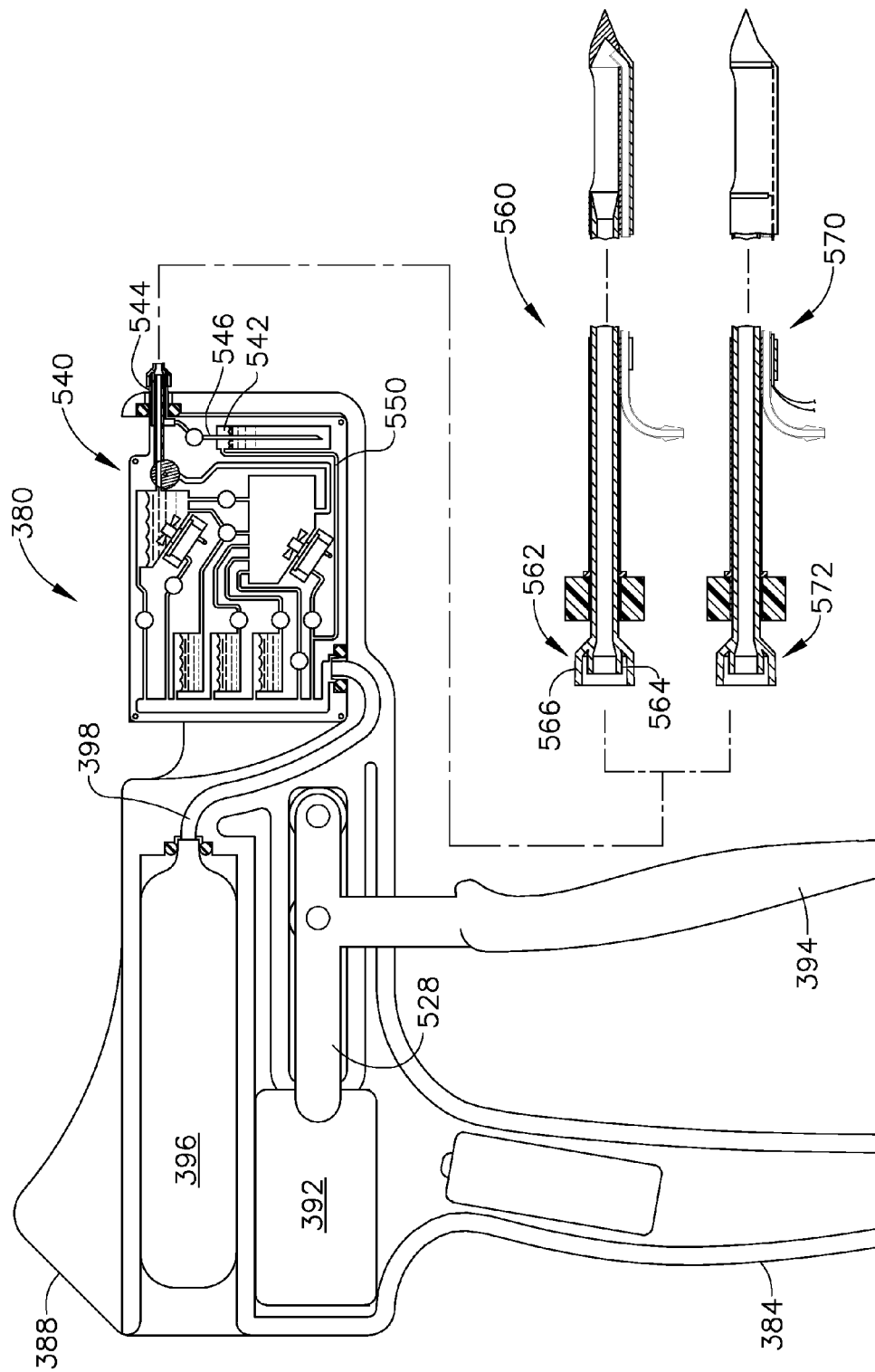
FIG. 28 depicts a partial cross-sectional view of a lumen repair device similar to that shown in FIG. 23, configured for dual lumen delivery of a tissue repair composition, along with two different harvesting probes.

While first and second harvesting probes (470, 490) may be attached to dual lumen inlet/outlet port (544) of bioprocessing module (540) such as by friction fit, FIG. 28 depicts a pair of slightly modified harvesting probes (560, 570). First harvesting probe (560) in FIG. 28 is similar to first harvesting probe (470) in FIG. 23, with the only difference being proximal end portion (562) of first harvesting probe (560). As seen in FIGS. 28-29, proximal end portion (562) includes a central, generally cylindrical inner end segment (564) and a flared outer segment (566), which extends around, proximally beyond, inner end segment (564), in spaced apart relationship. In this manner, an annular space is provided between the inner surface of flared outer segment (566) and the outer surface of inner end segment (564). In order to attach the distal end portion (562) of harvesting probe (560) to dual lumen inlet/outlet port (544), inner end segment (564) is inserted into the distal end of inlet/outlet port (544), into the annular lumen provided between outer tube (556) and the central tube (552) of inlet/outlet port (544). The proximal end portion (572) of second harvesting probe (570) is configured similarly, as best seen in FIG. 28.

Figure 30:
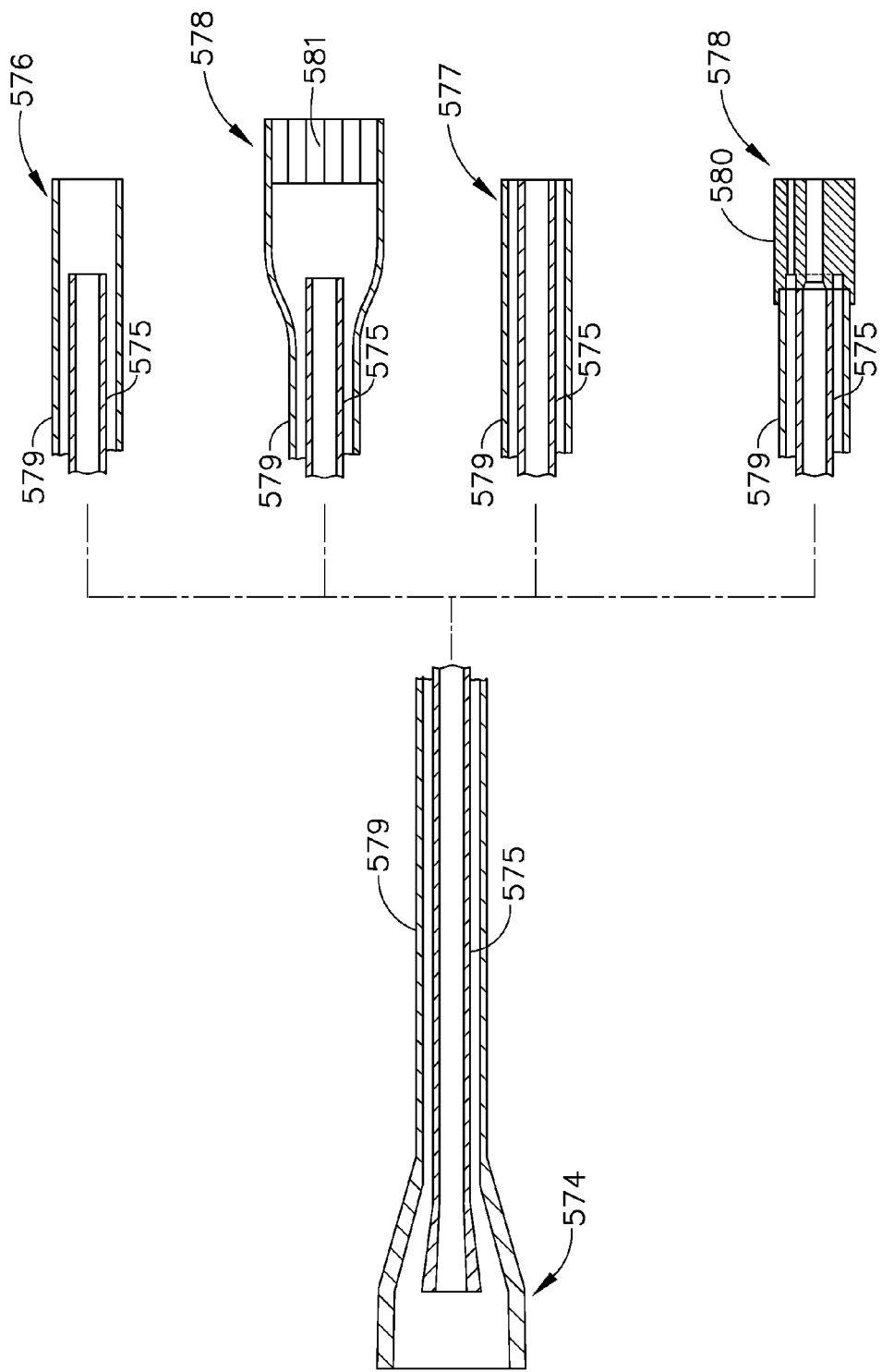
FIG. 30 depicts partial cross-sectional views of four different dual lumen delivery probes, each being configured for coupling with the lumen repair device of FIG. 28.
Figure 31:
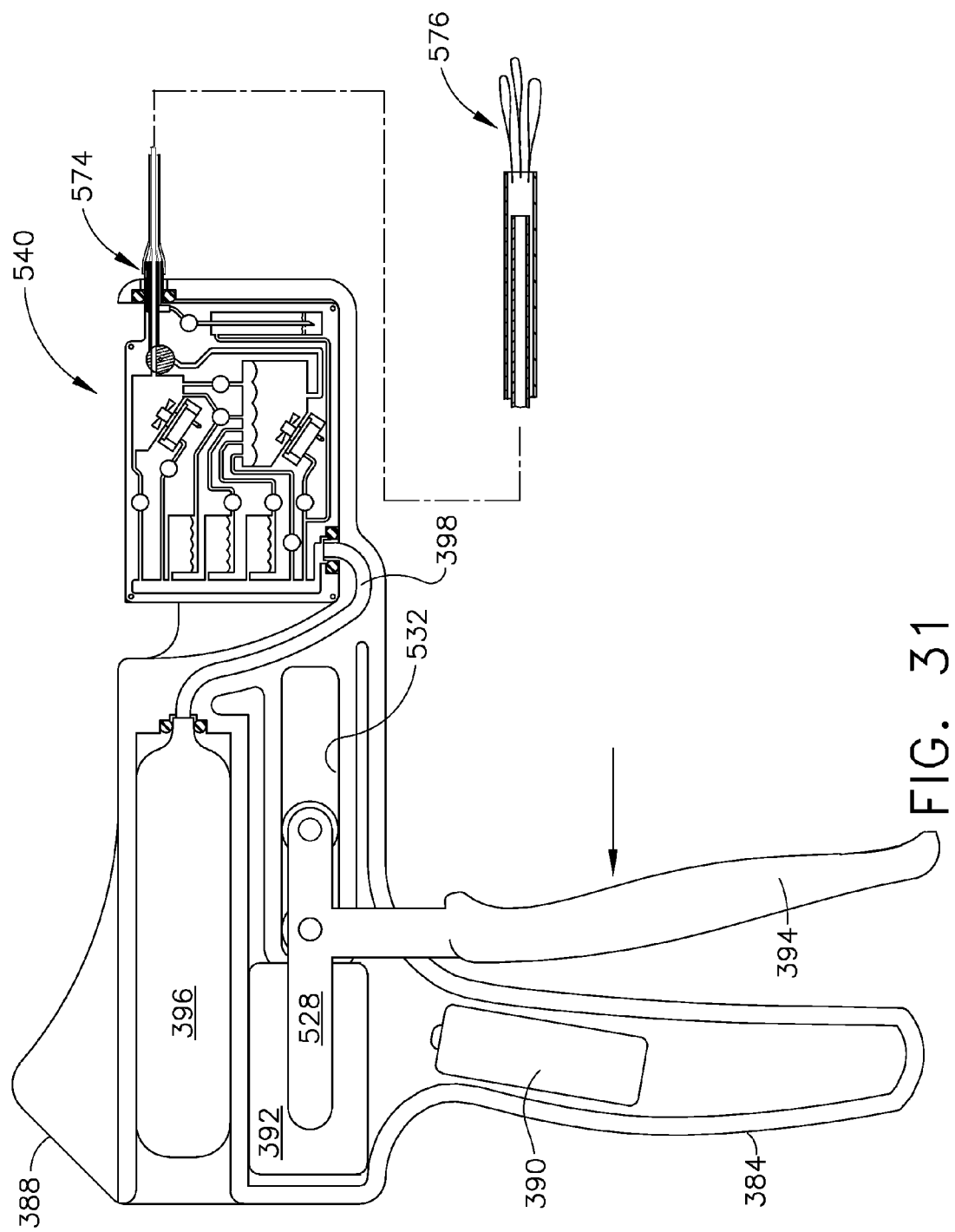
FIG. 31 depicts a partial cross-sectional view of the lumen repair device of FIG. 28, depicting a tissue repair composition being expelled from a dual lumen delivery probe of the device.

FIG. 30 depicts four types of exemplary dual lumen delivery probes that are removably attachable to inlet/outlet port (544) on bioprocessing module (540). The proximal end portion (574) is configured the same as biopsy probes (560, 570) described above. Each of these dual lumen delivery probes is also similar in construction to delivery probe (226) shown in FIGS. 14-16, and thus comprises coaxial inner and outer tubes (575, 579). In first dual lumen delivery probe (576), the distal end of the inner tube (575) is located within the outer tube (579), spaced proximally away from the distal end of the outer tube. In second dual lumen delivery probe (577), the distal ends of the inner and outer tubes (575, 579) are coextensive with one another (the same as delivery probe (226) in FIGS. 14-16). Third dual lumen delivery probe (578) has a distal end configured to spread a tissue repair composition over a wider area, as well as to mince tissue fragments or other materials in the tissue repair composition. Thus, the distal end of the outer tube (579) is flared, and a tissue cutting screen (581) is positioned therein. Finally, fourth dual lumen delivery probe (578) includes an adapter sleeve (580) attached at its distal end. The adapter sleeve (580) redirects media expelled through the outer tube (579) so that the media is expelled adjacent to, but not concentrically around, the fluid expelled from the inner tube (575).

Figure 32:
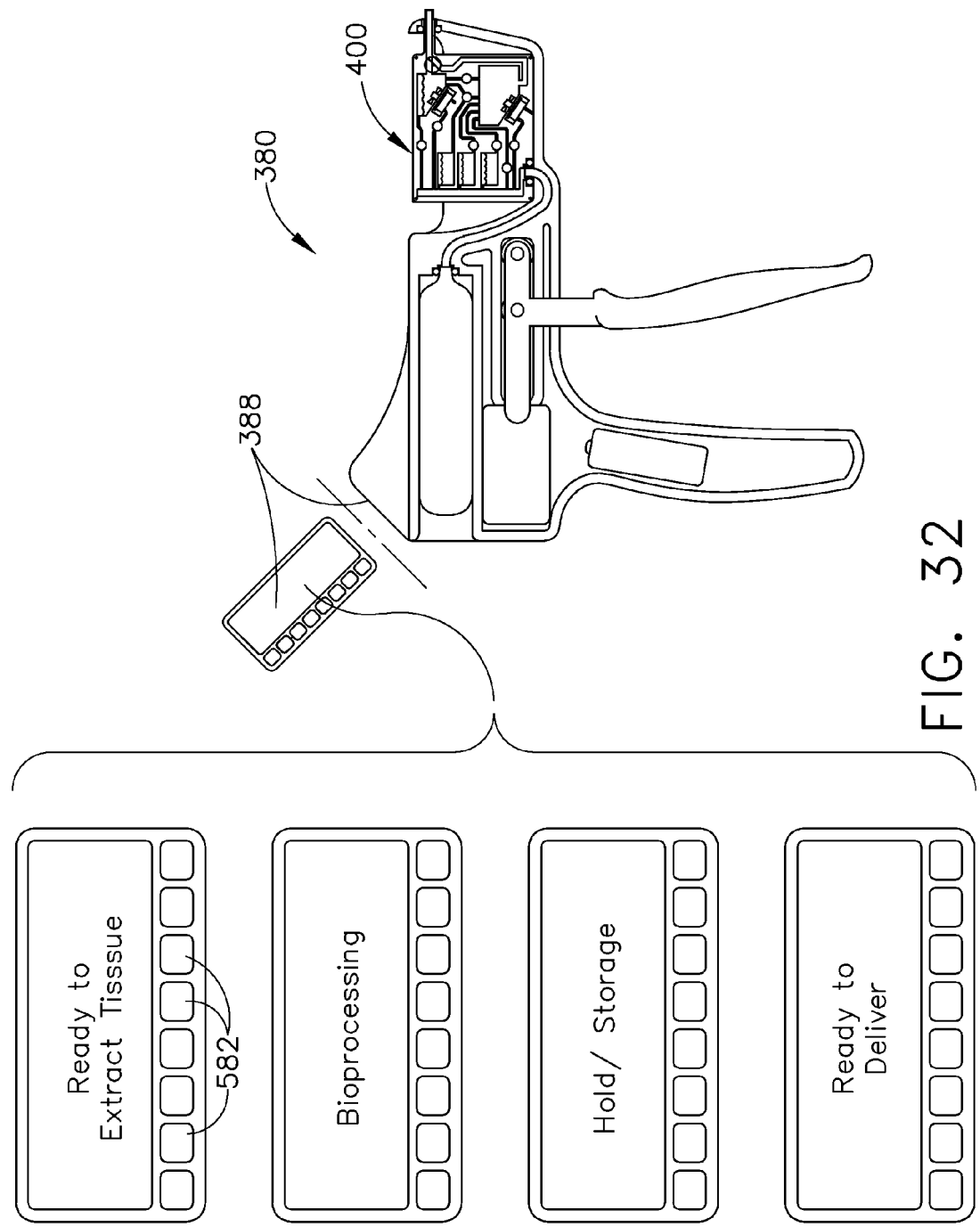
FIG. 32 depicts a partial cross-sectional view of the lumen repair device of FIG. 23, depicting various exemplary messages displayed on the LCD display screen of the device.

In order to use the lumen repair device (380) shown in FIGS. 23-32 to repair or otherwise address a lumen such as a fistula or some other site in a patient, a media loaded bioprocessing module (400, 540) is inserted into housing (382), and a harvesting probe (470, 490, 560, 570) is attached to inlet/outlet port (404). The repair device (380) is turned on, and LCD display screen (388) will display various diagnostic messages to the user (e.g., verifying that a bioprocessing module (400, 540) is properly seated within housing (382), indicating that the reservoirs in the module (400, 540) are filled, identifying that a harvesting probe is attached, etc.). Thereafter, and as shown in FIG. 32, LCD screen (388) will indicate that device (380) is ready to harvest tissue. The user then inserts the distal end of the harvesting probe into the tissue harvesting site (e.g., into a muscle in the patient), and presses one of the identified buttons (582) adjacent LCD screen (388). The LCD screen may indicate which button should be pressed for tissue harvesting, or the buttons may be appropriately labeled. When the appropriate button is pressed, tissue specimens will be harvested by the distal end of the harvesting probe and communicated into morcellating chamber (406) as described above. A transparent window may be provided in housing (382) so that the user may verify that a sufficient quantity of harvested tissue has been deposited into morcellating chamber (406). In addition to or in lieu of manipulating a button to harvest tissue, the user may manipulate block (471, 491) as described above.

Once the tissue specimens have been deposited into morcellating chamber (406), processing unit (392), either automatically or in response to user input (e.g., using one or more of the buttons (582), etc.), will adjust valve (430) to deliver fluid (e.g., saline) from first reservoir (418) into morcellating chamber (406). LCD screen (388) will display a message to the user that tissue specimen processing and formulation of the tissue repair composition has begun (e.g., the "Bioprocessing" message shown in FIG. 32). Under processing unit (392) control, the morcellating impeller (452) will be activated so as to morcellate the tissue specimens into smaller tissue fragments. After a suitable period of time, processing unit (392) will instruct valve (442) and valve (450) to open so that the suspension of tissue fragments in morcellating chamber (406) will be delivered to mixing chamber (408). Thereafter, or at the same time, one or more of valves (430, 432, 434) will be opened (by instruction from processing unit (392)) to deliver media from reservoirs (418, 420, 422) into mixing chamber (408). Processing unit (392) will control the amount of media injected into mixing chamber (408) based on stored instructions and/or user input (e.g., input instructing processing unit (392) how much, or what type of tissue repair composition is needed, input identifying the type or size of fistula being repaired, etc.). Following formulation of a tissue repair composition within mixing chamber (408), it may be desirable or necessary for the composition to be held within mixing chamber (408) for a period of time prior to delivery in order to, for example, allow the various components to mix and/or interact with one another. In such instances, LCD screen (388) may display, for example, a "Hold/Storage" message, as shown in FIG. 32.

Once a tissue repair composition has been formulated in mixing chamber (408) under processing unit (392) control, a signal (e.g., audible and/or visual) will be provided to the user that the tissue repair composition is ready to be delivered. By way of example, LCD screen (388) may display a message to the end-user (e.g., "Ready to Deliver" message shown in FIG. 32). The harvesting probe is removed, and is replaced with a delivery probe (500, 508, 518, 576, 577, 578, 579) selected by the user. The distal end of the delivery probe is inserted into the fistula or at some other target site in a patient. When the distal tip of the delivery probe is at the appropriate location, the user then squeezes trigger (394) towards handle (384), which signals to processing unit (392) to expel the tissue repair composition through the delivery probe. Thus, under processing unit (392) control, valve (412) is rotated to its delivery position (FIG. 26), and, if bioprocessing module (540) is being used, valve (548) is opened. In this manner, as long as the user continues to squeeze trigger (394), tissue repair composition (as well as the auxiliary media from fourth reservoir (542)) will be expelled from the distal end of the delivery probe. Other suitable variations, components, features, configurations, and operabilities of tissue repair device (380) will be apparent to those of ordinary skill in the art in view of the teachings herein.

VII. Exemplary Surgical Kit for Delivering Treatment Media to Various Sites

FIGS. 33-44 depict another exemplary tissue repair device (590) for delivering a medical fluid such as a tissue repair composition to a variety of locations on or in a patent in need of repair. For example, tissue repair device (590) may be used to deliver a tissue repair composition into a fistula (e.g., an anal fistula) or other lumen, where the tissue repair composition comprises a suspension of one or more viable tissue fragments in a suitable biocompatible carrier. Tissue repair device (590) of this example is similar in construction to lumen repair device (110) shown in FIGS. 10-13, and is configured for delivering a tissue repair composition from a media cartridge containing a suspension of one or more viable tissue fragments in a biocompatible carrier solution. Various types of end effectors are provided, such that tissue repair device (590) may be used for a variety of purposes. While some versions of tissue repair device (590) are configured to deliver media from a single media cartridge inserted into the device (590), a media cartridge coupling is also provided in some versions such that a second media cartridge may be attached to the repair device (590) and its contents delivered along with the first media cartridge through a single or dual lumen end effector. Some versions allow a pair of media cartridges to be inserted into the device (590) and their contents ejected simultaneously through a single or dual lumen end effector.

Tissue repair device (590) of the present example includes a housing comprising a handle (592) having a grip portion (594) extending downwardly away from a proximal end of handle (592). A tapered coupling sleeve (596) is provided at a distal end of the handle (592). Sleeve (596) is configured such that any of a plurality of end effectors may be attached thereto, such as by friction fit over the sleeve (596). In some other versions, sleeve (596) may be replaced by any of a variety of other types of hollow connectors, such as a male or female Luer connector, with a mating connector provided on the various end effectors for attachment thereto (e.g., a female or male Luer connector). Sleeve (596) is hollow in order to allow fluid flow therethrough, and therefore has a bore (598) with an orifice (600) in the proximal end wall of bore (598). Each end effector includes at least one fluid conduit extending therethrough, and at least one orifice in communication with the fluid conduit through which a tissue repair composition may be expelled. A pumping device, as further described herein, is also provided for expelling tissue repair composition from an end effector attached to handle (592).

Figure 33:
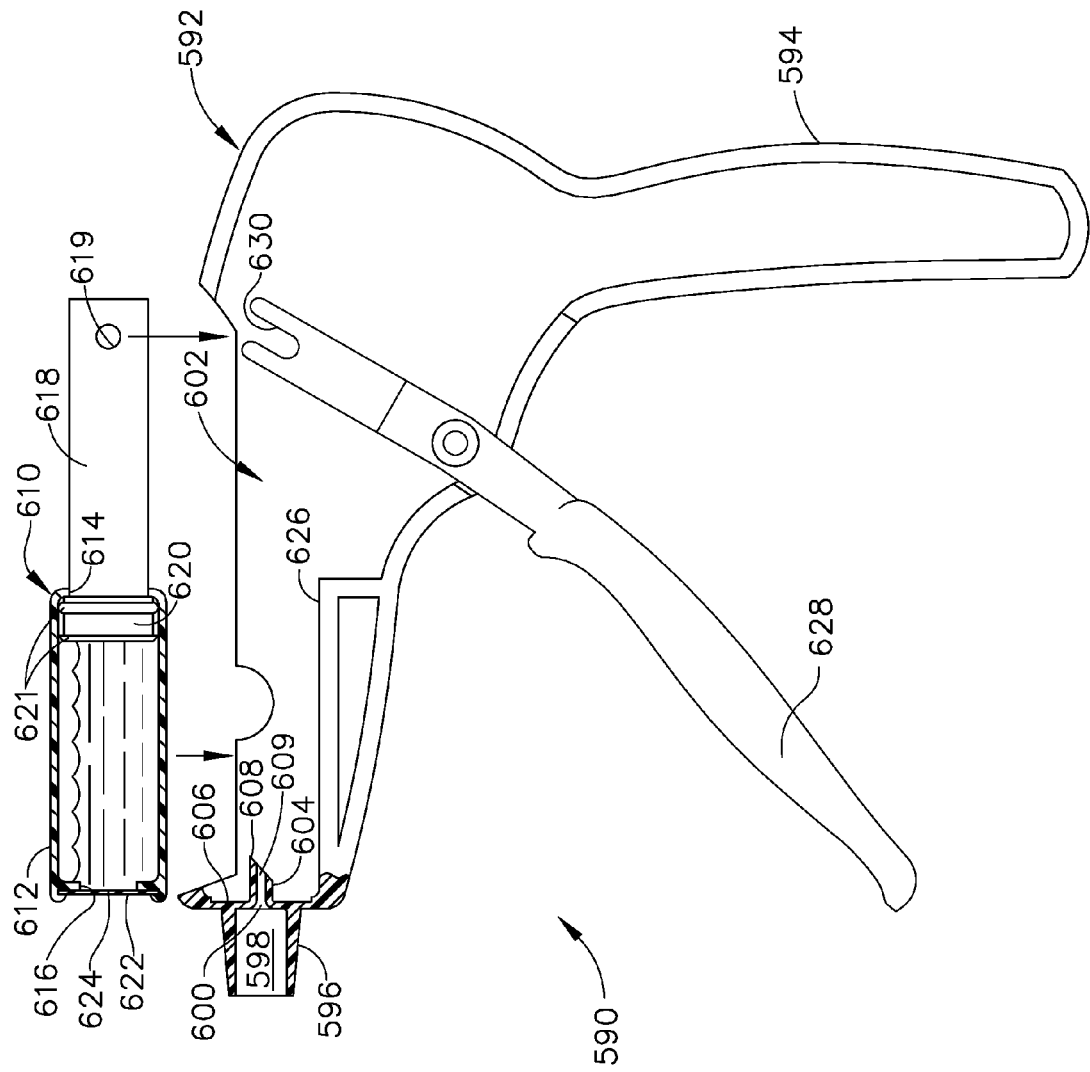
FIG. 33 depicts a partial cross-sectional view of an exemplary tissue repair device, with a media cartridge being installed into the handle of the device.

Handle (592) of lumen repair device (590) further includes a cartridge-receiving chamber (602) for alignably and detachably receiving one or more media cartridges (610) therein. As shown in FIG. 33, chamber (602) is located within handle (592) proximal to coupling sleeve (596). A nipple (604) extends proximally away from distal end wall (606) of cartridge-receiving chamber (602). Nipple (604) has a sharp proximal tip (608), and the passageway (609) extending longitudinally through nipple (604) communicates with orifice (600) at the base of coupling sleeve (596). As further described herein, a media cartridge (610) may be positioned within cartridge-receiving chamber (602), and a medical fluid component within cartridge (610) may be expelled through nipple (604) into an end effector attached to coupling sleeve (596). In other words, in order to supply a tissue repair composition or other treatment media to tissue repair device (590), one or more media reservoirs in the form of media cartridges (610) are provided. Media cartridge (610) is similar in construction to the cartridges (60, 90, 94, 156) shown and described in connection with previous embodiments, and are operatively insertable into handle (592) such that media within the cartridge may be expelled through an end effector attached to coupling sleeve (596).

As best seen in FIG. 33, each media cartridge (610) of the present example comprises a cylindrical barrel (612) having proximal and distal orifices (614, 616) in the proximal and distal end walls of barrel (612). A plunger (618) extends through the proximal orifice (614) of barrel (612) such that the plunger head (620) is located within barrel (612), as shown. Plunger head (620) is larger in diameter than the proximal orifice (614) such that plunger head (620) will be retained within barrel (612). Plunger head (620) includes a pair of sealing flanges (621) extending about the outer circumference of plunger head (620), and the diameter of flanges (621) is slightly larger than the interior diameter of barrel (612). Plunger head (620) is made from a resilient, compressible material, and therefore sealingly and slidably fits within barrel (612) (e.g., in a manner similar to the plunger head of a syringe). Plunger (618) functions similar to the plunger of a syringe in that, when plunger (618) is urged in the distal direction (i.e., towards distal orifice (616) of barrel (612)), media within cartridge (610) will be expelled from the distal orifice (616). A transverse mounting pin (619) is also provided adjacent the proximal end of plunger (618) and extends laterally away from plunger (618).

In the present example, a resilient flexible seal (622) is provided over distal orifice (616) of barrel (612). Flexible seal (622) comprises a slit (624), which is sufficiently small so that media within cartridge (610) will not inadvertently leak from the cartridge (610). Flexible seal (622) is configured to flex away from distal orifice (616) when nipple (604) is pressed into flexible seal (622). In particular, media cartridge (610) is inserted into cartridge-receiving chamber (602), against support surface (626), such that nipple (604) penetrates seal (622) through slit (624). In some other versions, seal (622) comprise a non-apertured septum, and the sharp proximal tip (608) of nipple (604) may simply penetrate the septum by puncturing. In addition or in the alternative, the distal end of cartridge (610) may have a coupling configured for attachment to a corresponding connector on, for example, nipple (604).

Figure 34:
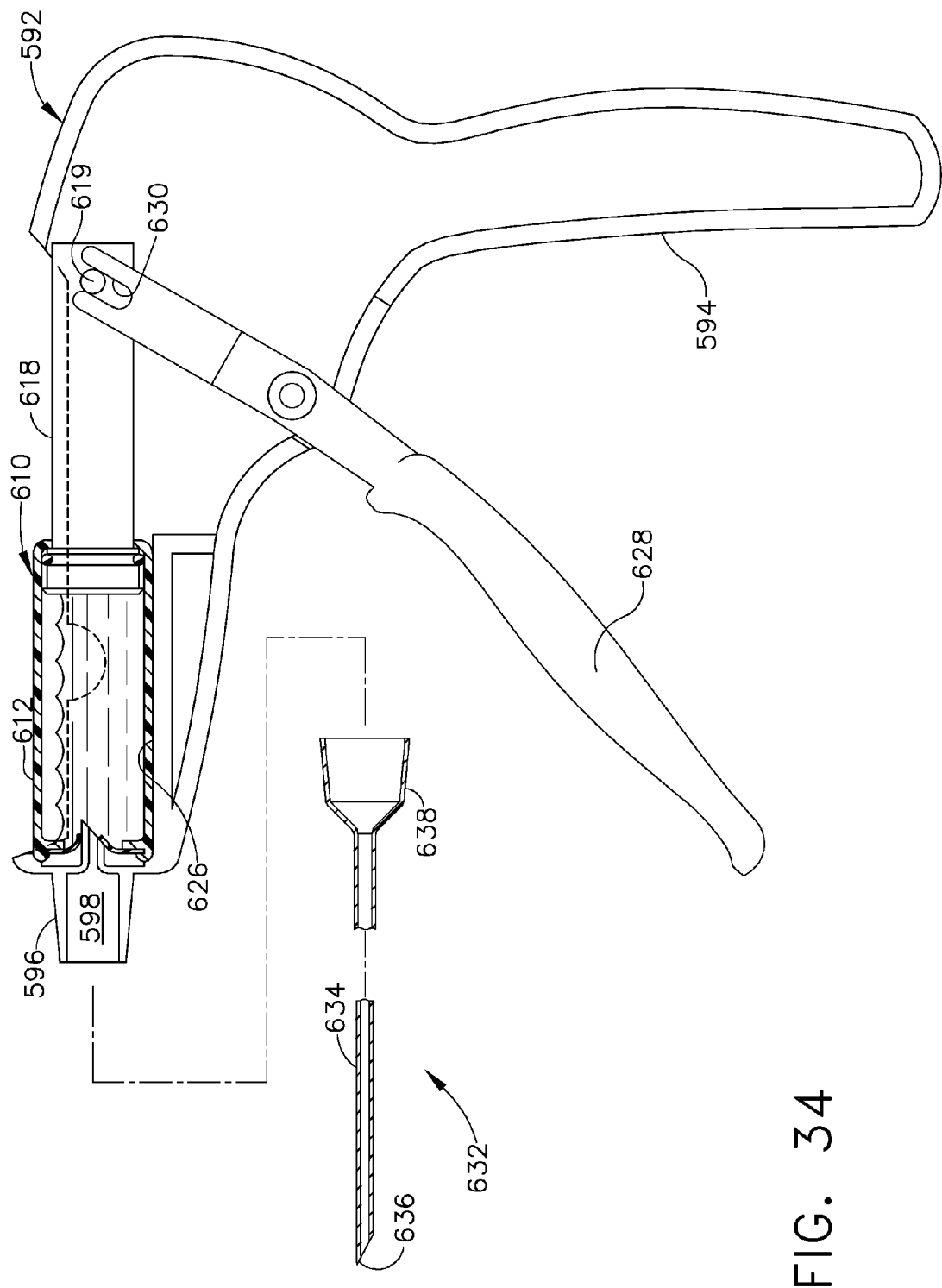
FIG. 34 depicts a partial cross-sectional view of the tissue repair device of FIG. 33, with a filled media cartridge installed in the handle of the device, and a delivery probe.

Support surface (626) at the base of cartridge-receiving chamber (602) is arcuate in nature (not shown) such that media cartridge is alignably received in chamber (602), with aperture (624) in seal (622) aligned with nipple (604). Thus, when plunger (618) is urged distally (i.e., towards coupling sleeve (596)), media contained within cartridge (610) will be expelled through coupling sleeve (596) and an end effector attached thereto. While a user may manually push plunger (618) of a media cartridge (610) inserted in handle (592), a trigger (628) is pivotally mounted within handle (592), in facing relationship with grip portion (594) in the present example. The upper end of trigger (628) includes a slot (630) that extends downwardly from the upper end of trigger (628). As best seen in FIG. 34, when a media cartridge (610) is inserted into cartridge-receiving chamber (602) with nipple (604) penetrating seal (622), mounting pin (619) will be positioned within slot (630) of trigger (628). Thus, when trigger (628) is squeezed towards grip (594), mounting pin (619), and hence plunger (618), will be urged axially and distally by slot (630), thus expelling the contents of the media cartridge (610) into coupling sleeve (596) and an end effector connected thereto.

Figure 35:
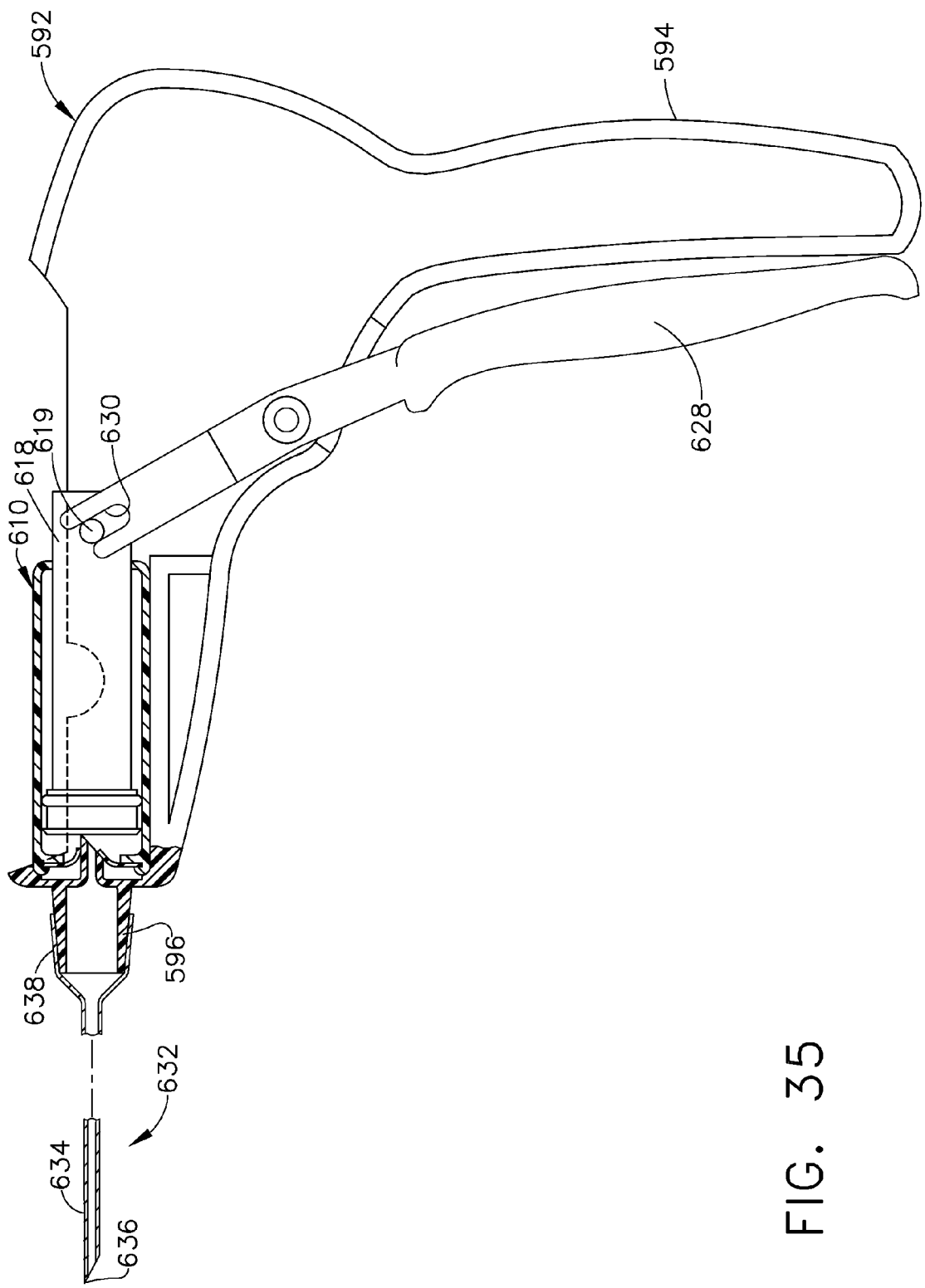
FIG. 35 depicts a partial cross-sectional view of the tissue repair device of FIG. 33, with a delivery probe attached thereto and the contents of the media cartridge expelled therefrom.

Any of a variety of delivery probes may be used in conjunction with tissue repair device (590), such as the delivery probes (130, 500, 508, 518) described previously in conjunction with other examples. For instance, FIGS. 34-35 depict an exemplary single lumen delivery probe (632) that is similar to delivery probes (130, 500) described previously. Delivery probe (632) comprises an elongate tube (634) having a sharp distal tip (636) and a flared proximal end portion (638) configured to be matingly received on tapered coupling sleeve (596) of tissue repair device (590). The proximal end portion (638) of tube (634) includes a tapered cavity and is friction fit over coupling sleeve (596). Other alternative types of couplings may be employed instead, such as Luer lock fittings. When delivery probe (632) is thus attached to coupling sleeve (596), a tissue repair composition may be expelled from media cartridge (610) through coupling sleeve (596), and into the elongate, hollow tube (634) of the delivery probe (632). The tissue repair composition will be expelled out of tube (632) at its distal end for delivery to the desired location. It will be understood that the distal end of delivery probe (632) may be provided in a variety of configurations, such as those shown in FIG. 27 for delivery probes (508, 518).

Other exemplary end effectors for attachment to tissue repair device (590) are shown in FIGS. 36-39, where each end effector is configured for delivering a tissue repair composition to a particular location in a patient. In each case, the end effector includes a flared proximal end portion similar to end portion (638) of delivery probe (632), with the flared proximal end portion configured to be matingly received on tapered coupling sleeve (596) of tissue repair device (590).

Figure 36:
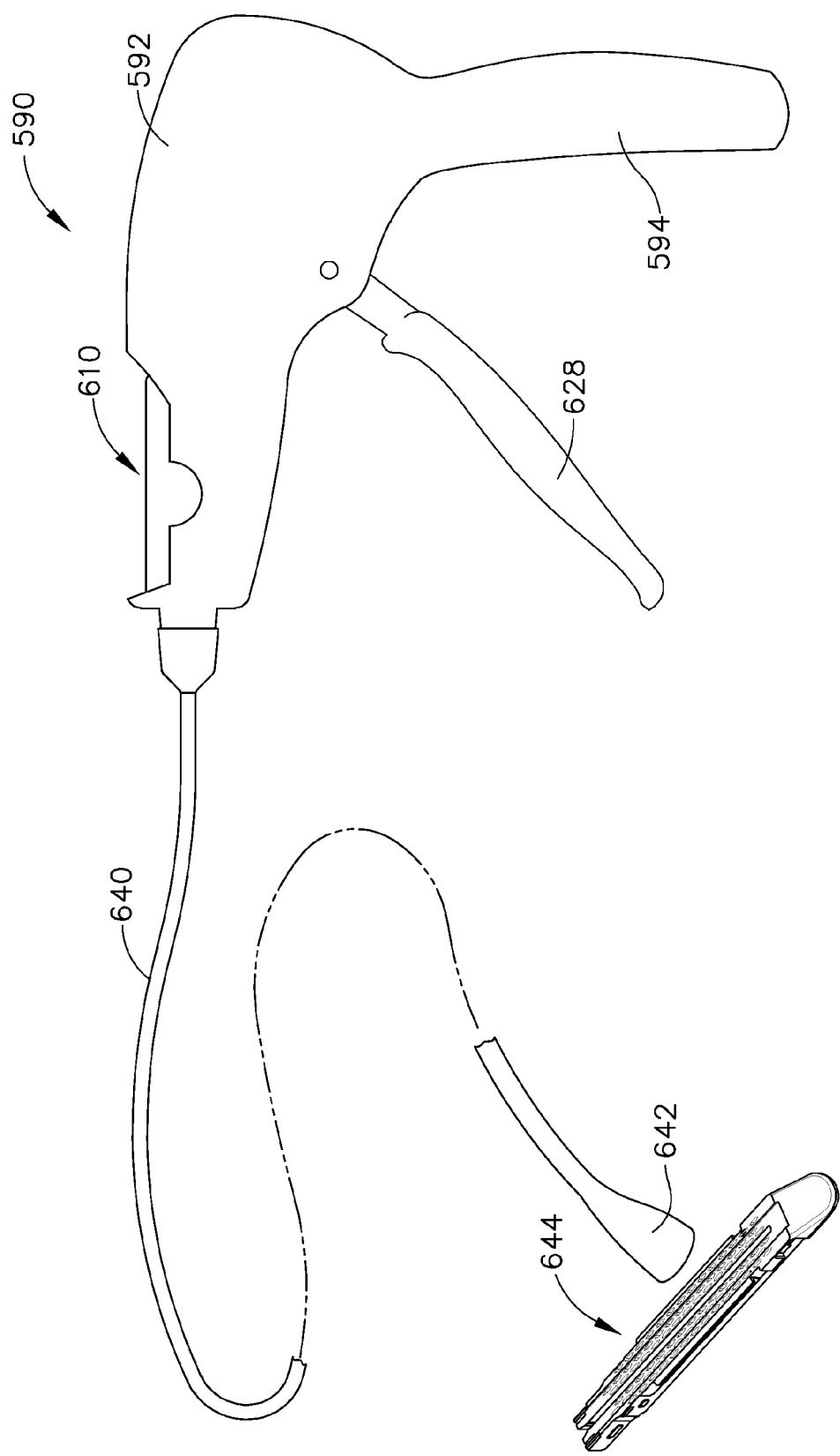
FIG. 36 depicts a schematic view of the tissue repair device of FIG. 33 being used in conjunction with a surgical stapler.

In FIG. 36, the end effector operatively attached to tissue repair device (590) comprises a flexible delivery probe (640) having a flared distal end portion (642). Distal end portion (642) is similar to that of delivery probe (508) shown in FIG. 27, with a plurality of tapered fins (not shown) extending laterally across the interior of distal end portion (642), with each fin having a sharpened proximal end (as shown for delivery probe (508) in FIG. 27). When a tissue repair composition comprising one or more viable tissue fragments is expelled from the distal end of delivery probe (640), the fins will further mince the tissue fragments and the flared distal end portion (642) will allow the user to more easily spread the tissue repair composition over a surface. While flexible delivery probe (640) may be used for any of a variety of purposes, FIG. 36 depicts flexible delivery probe (640) being used to apply a tissue repair composition to the end effector (e.g., the stapling head) of a linear surgical stapler (644) prior to use. By using tissue repair device (590) with attached flexible delivery probe (640) in this manner, the tissue repair composition will be applied to the staple line when the stapler (644) is used to staple tissue following application of the tissue repair composition to the end effector of the stapler.

Figure 37:
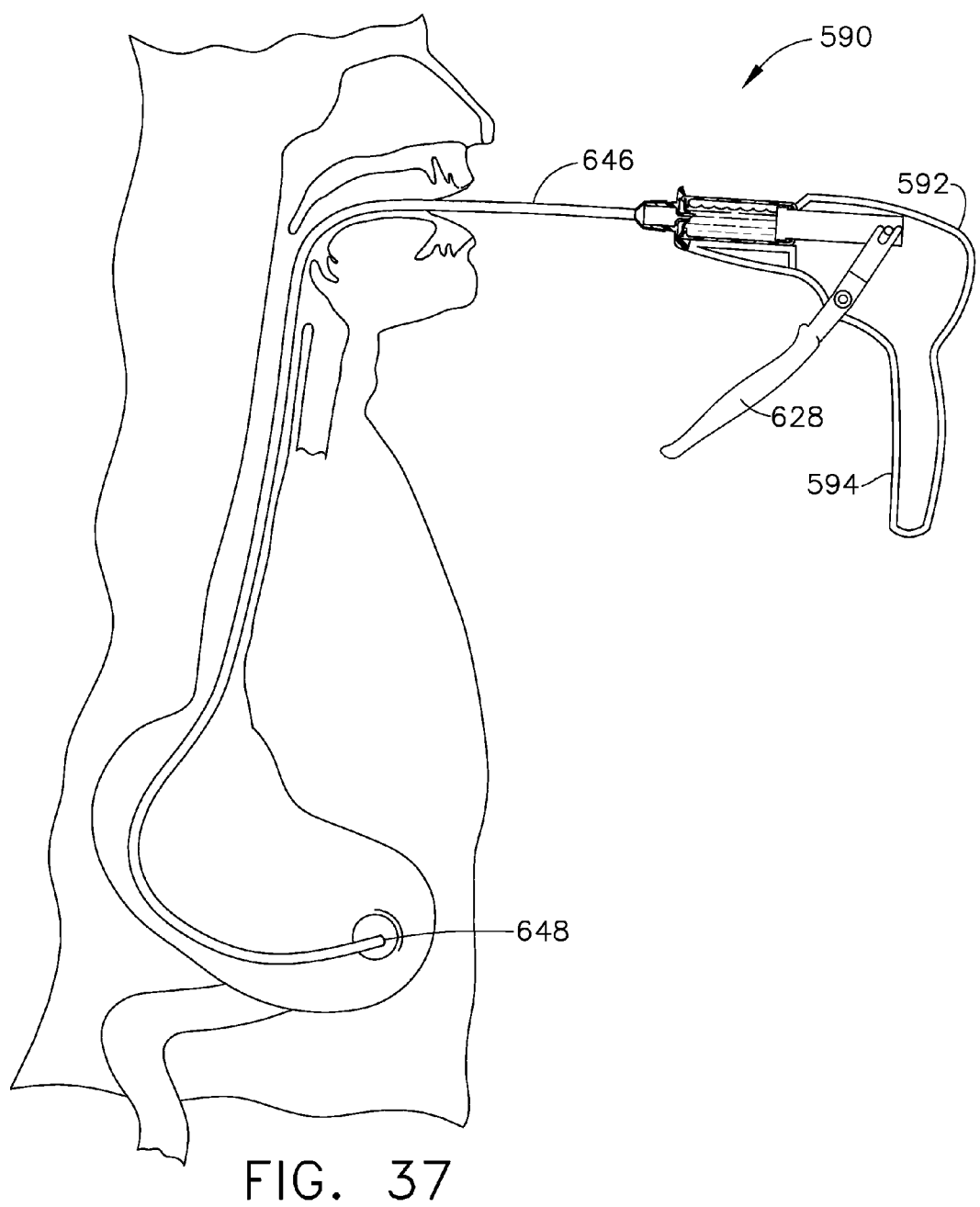
FIG. 37 depicts a schematic view of the tissue repair device of FIG. 33 being used in conjunction with flexible delivery probe for transorally delivering a tissue repair composition to a patient's stomach.

In FIG. 37, the end effector operatively attached to tissue repair device (590) comprises a flexible single lumen delivery probe (646) having an atraumatic distal tip (648). Delivery probe (646) is similar to delivery probe (632) shown in FIGS. 34-35, except that a blunt (atraumatic) distal tip (648) is provided instead of the sharp tissue-penetrating distal tip on delivery probe (632). Flexible single lumen delivery probe (646) may be used for any of a variety of purposes, such as delivering a tissue repair composition to a location within a patient. FIG. 37 depicts flexible delivery probe (646) being inserted through a patient's esophagus to position distal tip (648) in the patient's stomach. By using tissue repair device (590) with attached delivery probe (646) in this manner, the tissue repair composition may be applied, for example, to a transsection line following gastric bypass, stomach reduction or ulcer repair surgery.

Figure 38:
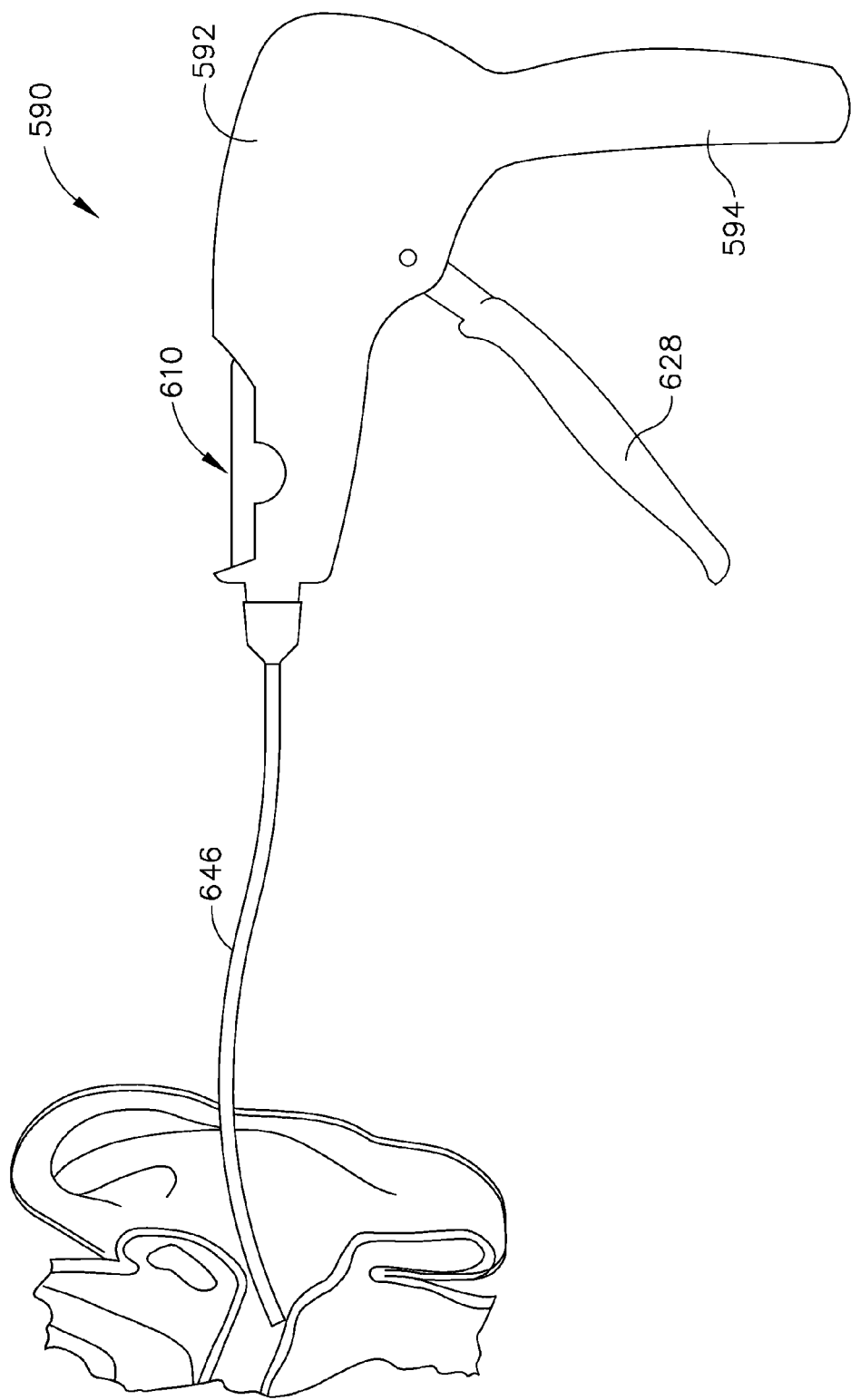
FIG. 38 depicts a schematic view of the tissue repair device of FIG. 33 being used in conjunction with flexible delivery probe for delivering a tissue repair composition to a patient's ear canal.

FIG. 38 shows another exemplary use of flexible single lumen delivery probe (646). In this example, flexible delivery probe (646) is depicted being used to apply a tissue repair composition within the ear canal of a patient. By using tissue repair device (590) with attached delivery probe (646) in this manner, the tissue repair composition may be applied, for example, within a patient's ear following ear drum repair or cleaning of the inner ear for treatment of infection.

Figure 39:
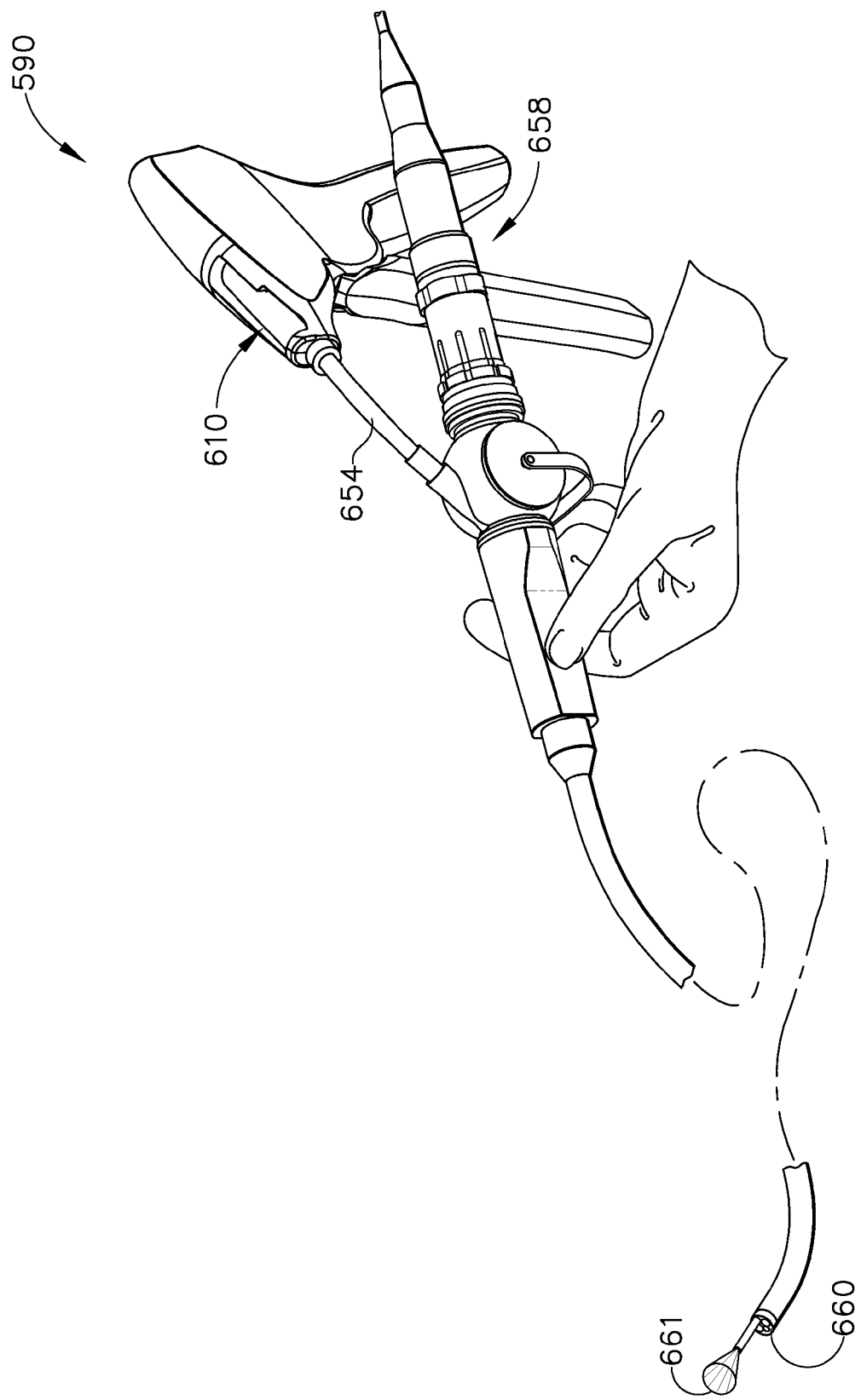
FIG. 39 depicts a schematic view of the tissue repair device of FIG. 33 being used in conjunction with an endoscope.

FIG. 39 depicts yet another exemplary end effector operatively attached to tissue repair device (590). In this example, the end effector comprises a tubular connector (654) inserted through an inlet port (656) of an endoscope (658). Inlet port (656) is in fluid communication with a working channel extending through the length of endoscope (658). The working channel is open at the distal end (660) of the endoscope (658) such that the distal end (661) of the end effector protrudes from the distal end (660) of the endoscope (658). A tissue repair composition expelled from a media cartridge (610) in tissue repair device (590) is thus expelled from the distal end (661) for application at the desired location within a patient.

Figure 40:
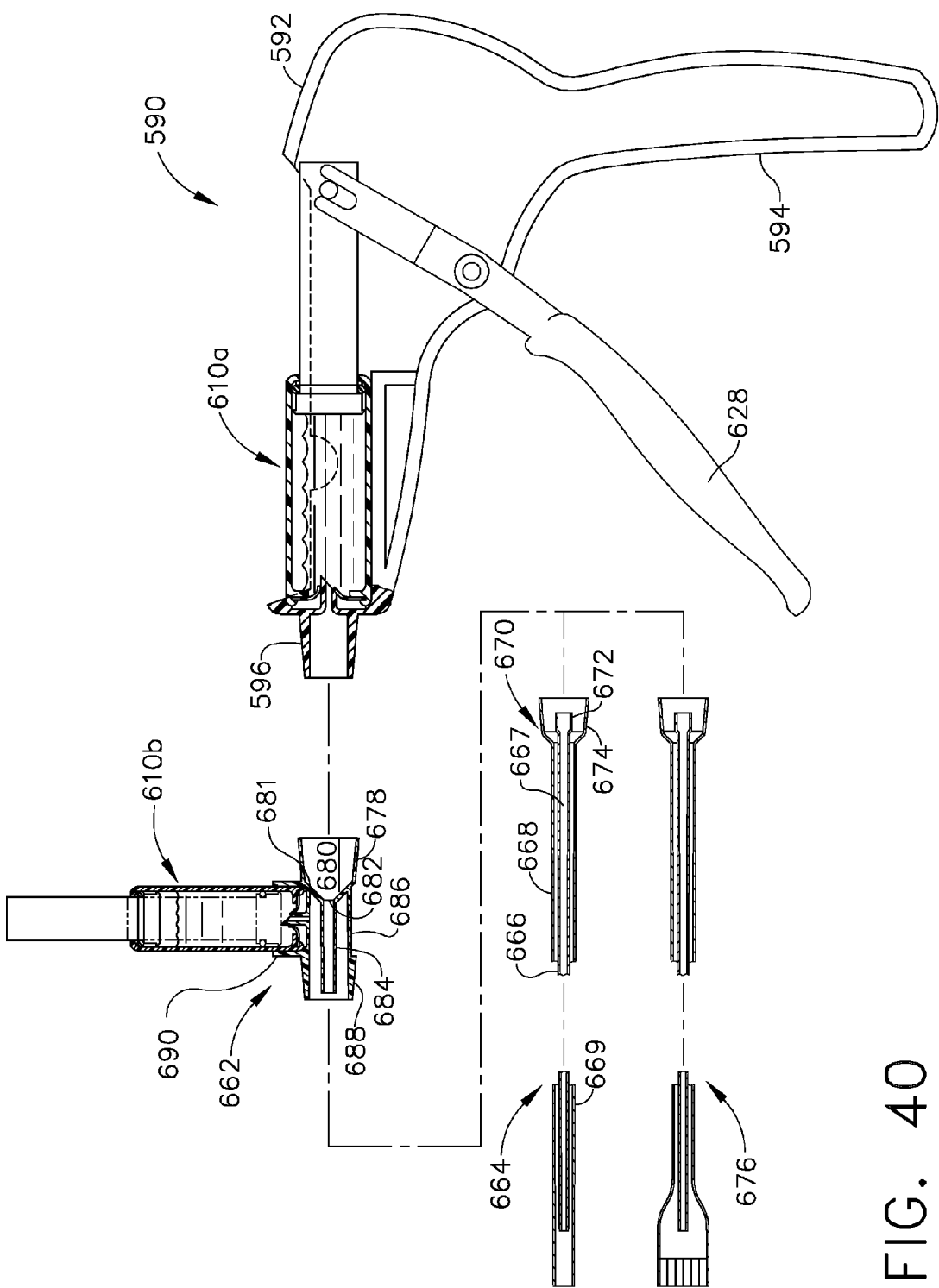
FIG. 40 depicts a partial cross-sectional view of the tissue repair device of FIG. 33 along with an auxiliary cartridge adapter, with a media cartridge installed in the body of the device and an auxiliary media cartridge installed in the auxiliary cartridge adapter.
Figure 41:
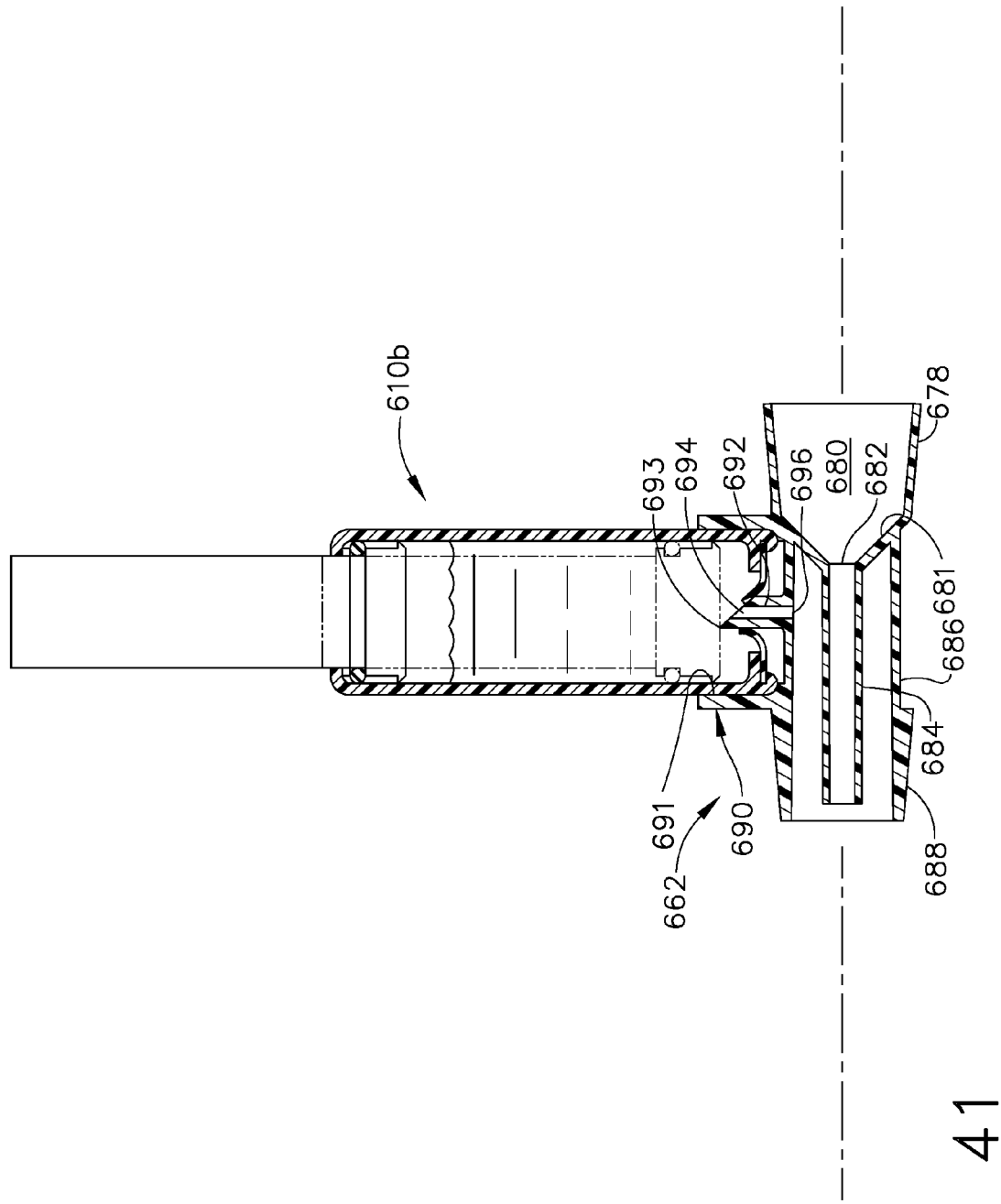
FIG. 41 depicts an enlarged cross-sectional view of the auxiliary cartridge adapter shown in FIG. 40.
Figure 42:
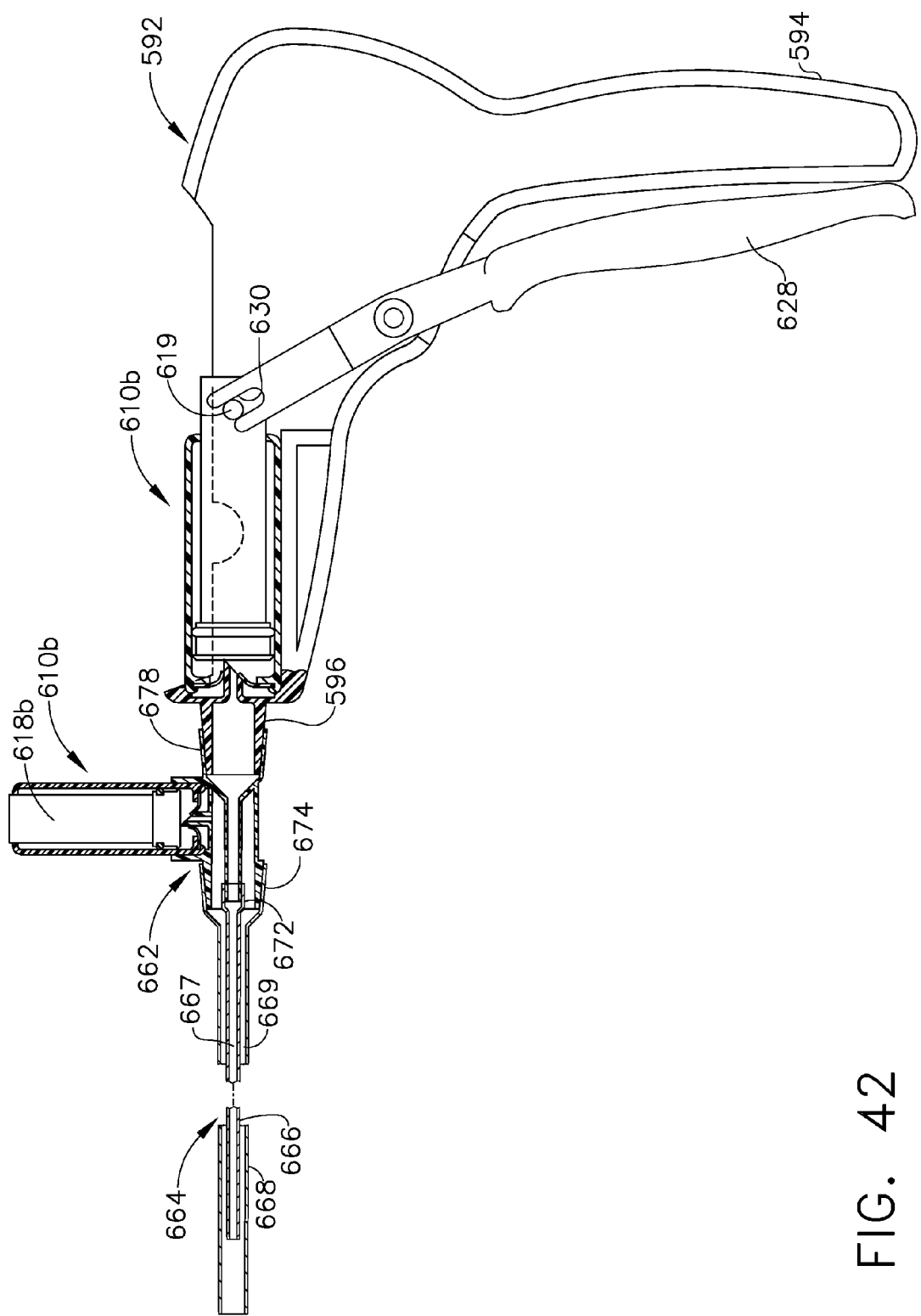
FIG. 42 depicts a partial cross-sectional view of the tissue repair device of FIG. 40, with the contents of the media cartridge installed in the body of the device, as well as the contents of the auxiliary media cartridge installed in the auxiliary media cartridge, having both been expelled through the dual lumen delivery probe attached to the device.

FIGS. 40-42 depict an exemplary auxiliary media cartridge adapter (662) that may be attached to tissue repair device (590) for dual lumen delivery of a tissue repair composition from a media cartridge (610a) mounted in handle (592) and a second treatment media contained in a second media cartridge (610b) mounted in auxiliary media cartridge adapter (662). A pair of dual lumen delivery probes (664, 676) are also shown in FIG. 40, and are similar in construction to the dual lumen delivery probes (576, 578) shown in FIG. 30. Thus, dual lumen delivery probe (664) has a pair of coaxial elongate tubes (666, 668). Inner tube (668) defines a first lumen (667) therein, and a second lumen (669) is provided in the annular space between inner tube (666) and outer tube (668). A plurality of struts (not shown) may extend between inner tube (666) and outer tube (668) along the lengths thereof in order to maintain proper relationship between tubes (666, 668) without preventing fluid flow through both lumens.

The proximal end portion (670) of dual lumen delivery probe (664) is configured for operative attachment to an outlet coupling sleeve (688) on auxiliary media cartridge adapter (662), as further described below. The proximal end of inner tube (666) includes a generally cylindrical end segment (672). The proximal end of outer tube (668) has a flared end segment (674). Flared end segment (674) extends around, and proximally beyond, end segment (672) of inner tube (666), in spaced apart relationship. In this manner, an annular space is provided between the inner surface of flared end segment (674) and the outer surface of inner end segment (672).

The distal end of dual lumen delivery probe (664) is configured similar to that of dual lumen delivery probe (576) shown in FIG. 30. Of course any of a variety of alternative configurations may be provided, such as that provided on the distal end of dual lumen delivery probe (676) also shown in FIG. 40. The proximal end of dual lumen delivery probe (676) is configured the same as that of delivery probe (664) for attachment to auxiliary media cartridge adapter (662). The distal end of delivery probe (676) is configured similar to that of dual lumen delivery probe (578) shown in FIG. 30.

Auxiliary media cartridge adapter (662) is configured to operatively receive a media cartridge (610b), and to be operatively connected between coupling sleeve (596) and a dual lumen delivery probe (664 or 676). Auxiliary media cartridge adapter (662) includes a female coupling (678) having a tapered cylindrical cavity (680) sized and configured to be friction fit over coupling sleeve (596). As noted in with respect to previous examples, other alternative types of couplings may be employed instead, such as Luer lock fittings, etc. A frustoconical shoulder (681) extends distally away from tapered cylindrical cavity (680), and an orifice (682) is provided in the distal end of shoulder (681). An inner adapter delivery tube (684) extends distally away from frustoconical shoulder (681) at orifice (682), such that orifice (682) provides fluid communication between cavity (680) and inner adapter delivery tube (684). An outer sleeve (686) also extends distally away from frustoconical shoulder (681), and is concentric with inner adapter delivery tube (684) such that an annular space is provided between outer sleeve (686) and inner adapter delivery tube (684). The distal end portion (688) of outer sleeve (686) is also tapered, as shown, and provides a coupling to which an end effector may be attached.

A cartridge mount (690) is also provided on auxiliary media cartridge adapter (662), and comprises a cylinder extending upwardly away from outer sleeve (686) so as to define a cylindrical cartridge mounting cavity (691) therein (see FIG. 41). Mounting cavity (691) is sized and configured to snugly receive the distal end portion of a media cartridge (610) therein. A nipple (692) extends upwardly away from outer sleeve (686) within cavity (691). Nipple (692) has a sharp proximal tip (693), and a passageway (694) extending longitudinally through nipple (692) communicates with an orifice (696) provided in outer sleeve (686).

A media cartridge (610*b*) may be inserted into cartridge mounting cavity (691) of auxiliary media cartridge adapter (662), against outer sleeve (686) such that nipple (692) penetrates seal (622) through aperture (624) on media cartridge (610*b*). In some versions, seal (622) comprises a non-apertured septum, and the sharp proximal tip (693) of nipple (692). Thus, when plunger (618) of the media cartridge (610*b*) mounted in auxiliary media cartridge adapter (662) is urged distally (i.e., downwardly towards outer sleeve (686)), media contained within cartridge (610*b*) will be expelled through nipple (692) into the annular space between outer sleeve (686) and inner adapter delivery tube (684), and thereafter through the outer lumen of a dual lumen delivery probe attached to sleeve (596) and an end effector attached to auxiliary media cartridge adapter (662).

In order to attach the proximal end portion (670) of dual lumen delivery probe (664, 676) to auxiliary media cartridge adapter (662), with auxiliary media cartridge adapter (662) being attached to coupling sleeve (596) of handle (592), inner proximal end segment (672) of the delivery probe is inserted into the annular space between outer sleeve (686) and inner adapter delivery tube (684) (i.e., over the distal end of inner tube (684)), with outer proximal end segment (674) of the delivery probe snugly fitting over tapered distal end portion (688) of sleeve (686) (see FIG. 42).

As shown in FIG. 42, a media cartridge (610*a*) is mounted within handle (592) of tissue repair device (590), a second media cartridge (610*b*) is mounted in auxiliary media cartridge adapter (662) attached to coupling sleeve (596) of handle (592), and a dual lumen delivery probe (664) is mounted to the distal end of auxiliary media cartridge adapter (662). Delivery probe (664) is positioned in the patient at the desired location (e.g., within a fistula), and trigger (628) is then squeezed in order to expel a tissue repair composition from the media cartridge (610*a*) mounted within handle (592), while simultaneously depressing plunger (618*b*) of the second media cartridge (610*b*) so as to also expel the media from second media cartridge (610*b*). The tissue repair composition will be urged through the inner tube (666) of the delivery probe (664), while the media from second media cartridge (610*b*) will be urged through the second lumen (669) provided between the inner and outer tubes (666, 668) of the delivery probe (664). The tissue repair composition will exit inner tube (666) just proximal to the distal end of the delivery probe (664), where it will mix with the media of the second media cartridge (610*b*). The combined mixture is then expelled from the distal end of delivery probe (664).

Lumen repair device (590) may be used to deliver any of a variety of tissue repair compositions to a tissue repair location (e.g., a fistula). By way of example, a tissue repair composition comprising a suspension of one or more viable tissue fragments in a biocompatible carrier may be provided in the media cartridge (610) inserted into handle (592) (e.g., tissue fragments in a flowable gel solution comprising fibrin and/or collagen). When the auxiliary cartridge adapter (662) is used, the media cartridge (610) attached thereto may be filled with one or more additional healing agents such as growth factors and/or any of the other various medical fluid components referred to herein.

Figure 43:
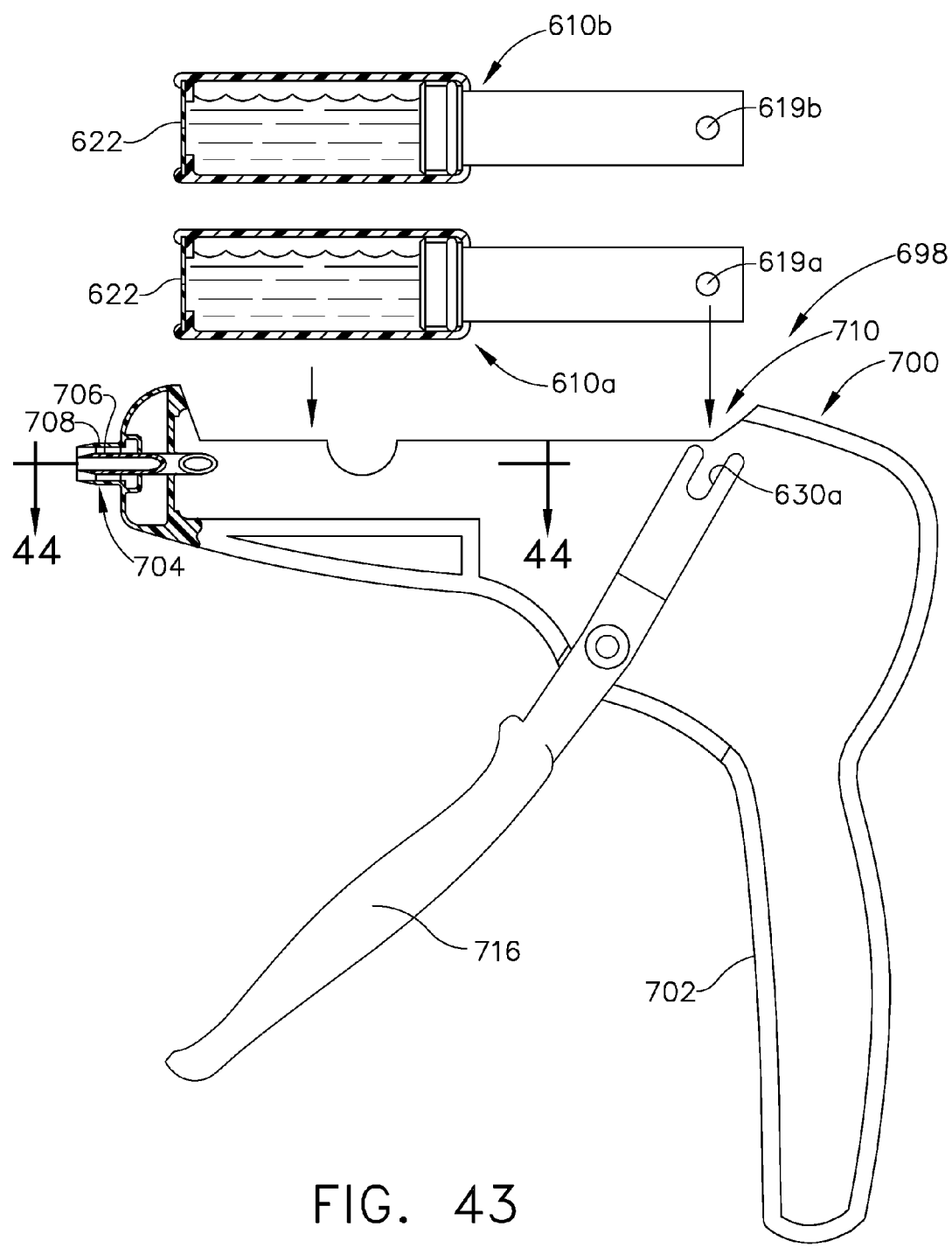
FIG. 43 depicts a partial cross-sectional view of another exemplary tissue repair device similar to that shown in FIG. 33, with a pair of media cartridges being installed in the body of the device.
Figure 44:
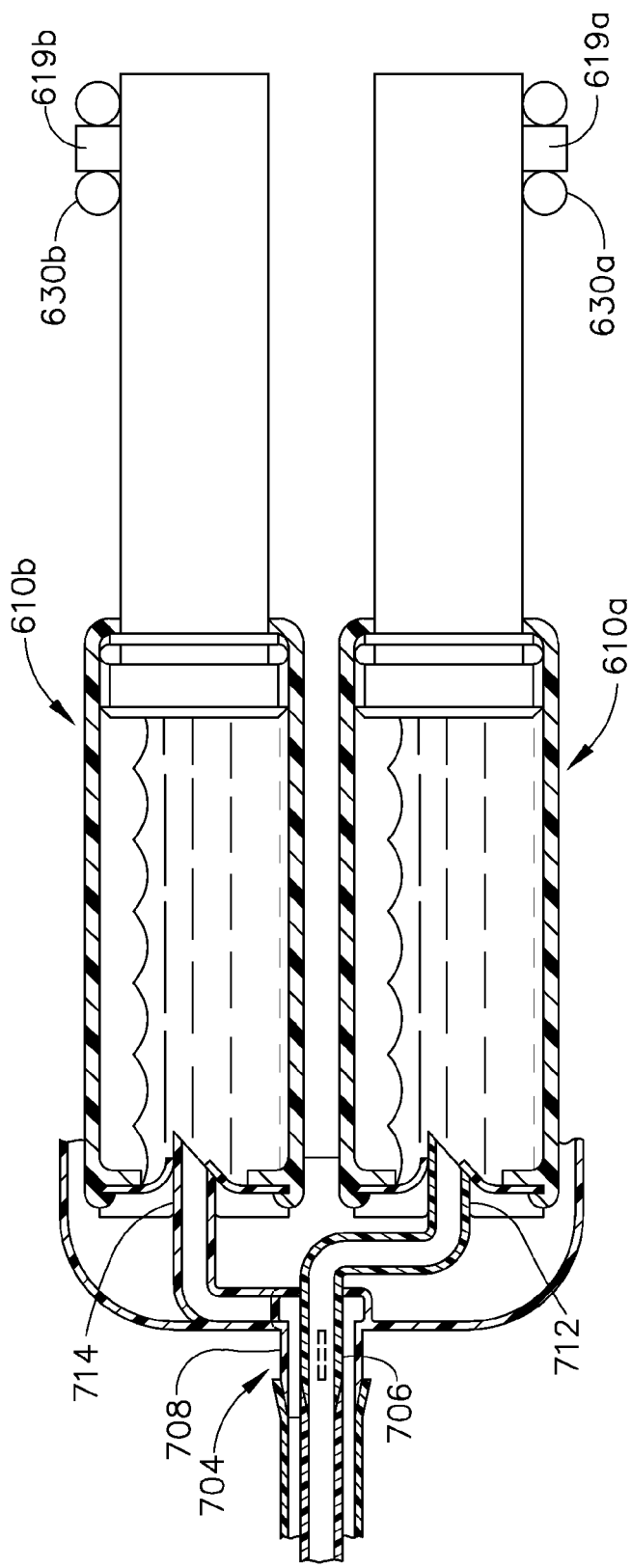
FIG. 44 depicts a partial cross-sectional top view of the tissue repair device shown in FIG. 43.

FIGS. 43-44 depict yet another example of a tissue repair device (698). Tissue repair device (698) is similar to tissue repair device (590), and is configured to deliver media through a dual lumen delivery probe. Instead of using an auxiliary cartridge adapter, however, the handle (700) of the device (698) is configured to receive both media cartridges (610*a*, 610*b*) and simultaneously expel the contents of the media cartridges (610*a*, 610*b*) through a dual lumen end effector. As seen in FIG. 43, tissue repair device (698) of this example comprises a handle (700) having a grip portion (702) extending downwardly away from a proximal end of handle (700). A tapered coupling sleeve (704) is provided at a distal end of the handle (700). Sleeve (704) is configured such that any of a plurality of dual lumen end effectors (e.g., 674, 676 shown in FIG. 40), may be attached thereto, by friction fit onto the sleeve (704). Sleeve (704) includes an inner tube (706) and an outer tube (708) coaxially positioned about inner tube (706). A dual lumen delivery probe (674, 676) may be attached to coupling sleeve (704) in the same manner in which the dual lumen delivery probe is attached to auxiliary cartridge adapter (662), as shown in FIG. 42.

Handle (700) of tissue repair device (698) further includes a cartridge-receiving chamber (710) for alignably and detachably receiving a pair of media cartridges (610*a*, 610*b*), in side-by-side relationship, therein. Alternatively, the cartridge-receiving chamber may be configured to receive media cartridges one on top of the other, or any of a variety of other orientations. As shown in FIG. 43, chamber (710) is located within handle (700) proximal to coupling sleeve (704). First and second nipples (712, 714) are provided in the distal end of chamber (710), with first nipple (712) in fluid communication with inner tube (706) of sleeve (704), and second nipple (714) in fluid communication with the annular lumen extending through sleeve (704) between inner tube (706) and outer tube (708). Nipples (712, 714) have sharp proximal tips, such that when media cartridges (610*a*, 610*b*) are inserted into cartridge-receiving chamber (710), nipples (712, 714) will penetrate seals (622) on cartridges (610*a*, 610*b*). When plungers (618*a*, 618*b*) are urged distally (i.e., towards coupling sleeve (704)), media contained within cartridges (610*a*, 610*b*) will be expelled through coupling sleeve (704) and dual lumen delivery probe (664) attached thereto. In particular, media from first media cartridge (610*a*) will be urged through first lumen (667) of delivery probe (664); and media from second media cartridge (610*b*) will be urged through second lumen (669) of delivery probe (664).

While a user may manually push plungers (618a, 618b) of a media cartridges (610a, 610b) inserted in handle (700), the present example of tissue repair device (698) once again includes a trigger (716) pivotally mounted within handle (700), in facing relationship with grip portion (702). The upper end of trigger (716) includes a pair of space apart slots (630a, 630b) located on a pair of spaced-apart arms (not shown) at the upper end of trigger (716). As best seen in FIG. 44, when media cartridges (610a, 610b) are inserted into cartridge-receiving chamber (710) with nipples (712, 714) penetrating seals (622a, 622b), transverse mounting pins (619a, 619b) will be positioned within slots (630a, 630b) of trigger (716). Thus, when trigger (716) is squeezed towards grip (702), mounting pins (619a, 619b), and hence plungers (618a, 618b), will be urged axially and distally by slots (630a, 630b), thus expelling the contents of media cartridges (610a, 610b) into coupling sleeve (704) and a dual lumen end effector connected thereto.

Tissue repair device (698) may be used in the same manner as tissue repair device (590). For example, first cartridge (610a) may be filled with a tissue fragment suspension (e.g., tissue fragments harvested from the patient), and second cartridge (610b) may be filled with a solution of one or more additional medical fluid components (e.g., healing agents, etc.). Other suitable variations, components, features, configurations, and operabilities of repair devices (590, 698) will be apparent to those of ordinary skill in the art in view of the teachings herein.

VIII. Exemplary Self-Contained Lumen Repair Device

FIGS. 45-50 depict another example of a lumen repair device (720). Lumen repair device (720) may be used, for example, to repair a fistula, such as an anal fistula. Alternatively, lumen repair device (720) may be used to address various other target sites in a patient. Lumen repair device (720) of the present example is configured to not only harvest tissue fragments from a patient, but also to clean and debride the interior of the lumen to be repaired and deliver a biocompatible scaffold plug loaded with the harvested tissue fragments and other medical fluid components. Lumen repair device (720) may be provided to users preloaded with a cleaning solution as well as a tissue healing composition having any of a variety of components for promoting healing, tissue regeneration, and/or other results.

Figure 45:
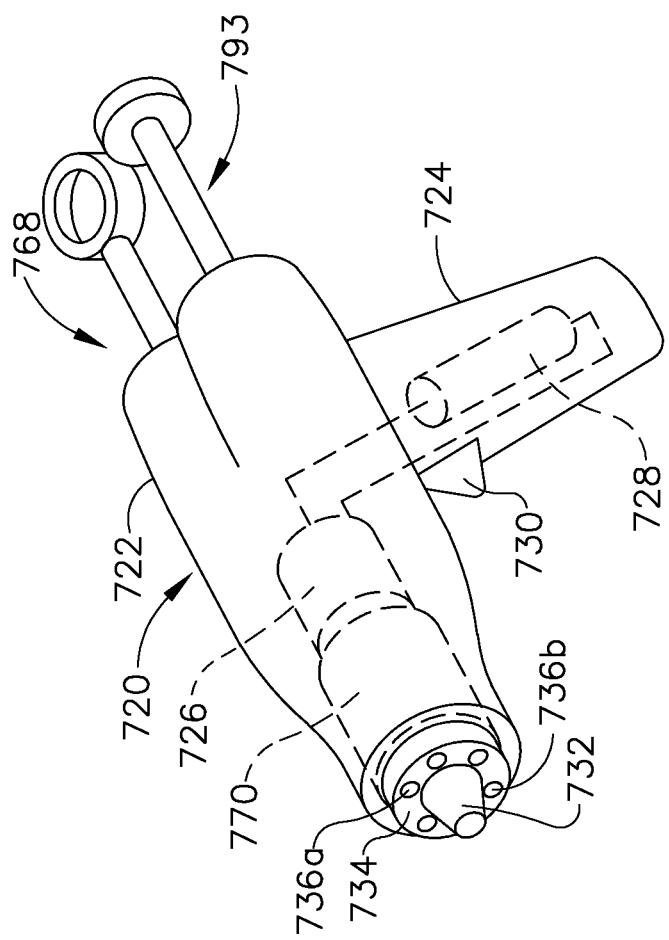
FIG. 45 depicts a schematic perspective view of another exemplary lumen repair device.

As shown in FIG. 45, lumen repair device (720) comprises a housing (722) and a handle (724) extending downwardly away from housing (722). A motor (726) is provided in housing (722). A battery (728) for providing power to drive motor (726) is located in handle (724), and is operatively connected to motor (726). A motor switch (730) is also provided on handle (724), and is configured for energizing motor (726) whenever depressed. It will be understood that lumen repair device (720) may alternatively be connectible to an external power supply for supplying power to drive motor (726). It should also be understood that a variety of alternative components or devices may be used to drive components of lumen repair device (720) in addition to or in lieu motor (726).

Lumen repair device (720) is further configured such that a variety of interchangeable end effectors may be attached thereto and be rotated by motor (726). In the present example, a coupler (732) is provided at a distal end of housing (722) and is operably connected to motor (726) such that coupler (732) is rotated when motor (726) is energized. In present example, coupler (732) comprises a taper-lock coupler. Of course any of a variety of other coupler may be used in place of a taper-lock coupler. A mounting flange (734) extends around the base of coupler (732), and includes a pair of fluid passageways (736a, 736b) and extending longitudinally through flange (734). Fluid passageways (736a, 736b) provide fluid communication between fluid passageways provided in an end effector attached to coupler (732) and fluid passageways in a rotating fluid manifold shaft located in housing (722) as described further herein.

Figure 46:
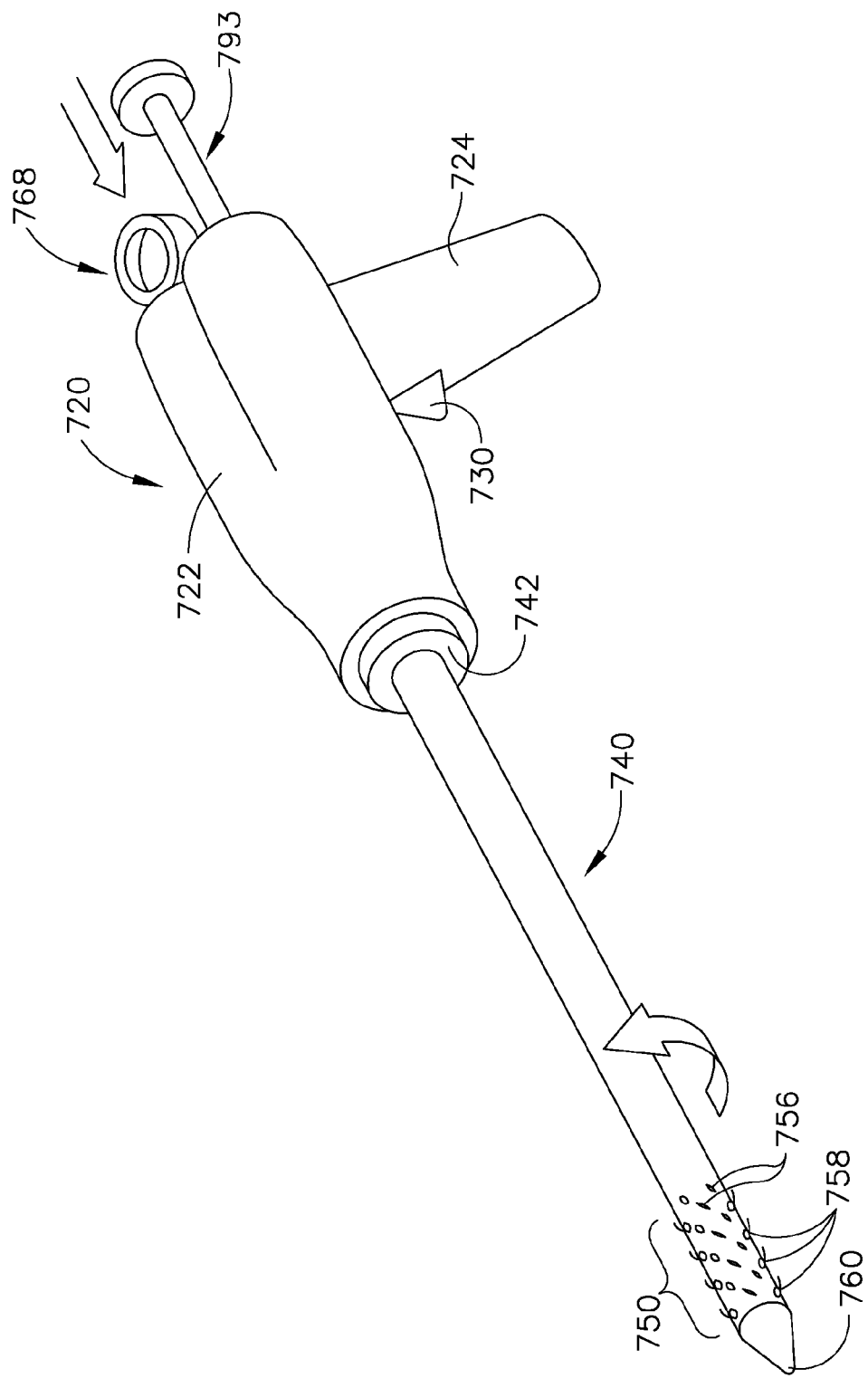
FIG. 46 depicts a schematic perspective view of the lumen repair device of FIG. 45, with a harvesting end effector attached thereto.
Figure 47:
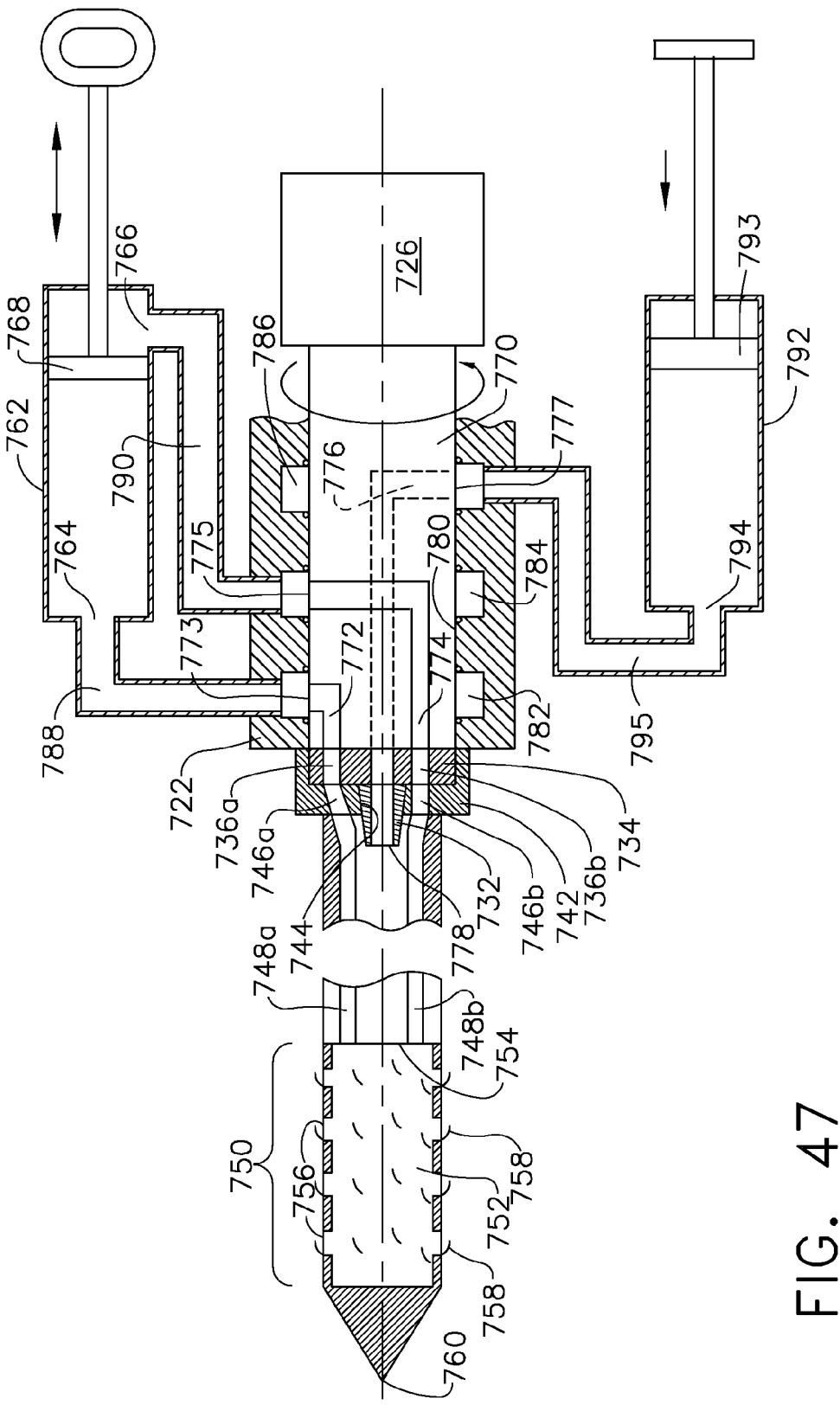
FIG. 47 depicts a schematic partial cross-sectional view of the lumen repair device of FIG. 46.

As shown in FIG. 46, where a harvesting end effector (740) has been operatively attached to coupler (732), the end effectors for use with lumen repair device (720) have a proximal end configured to matingly receive taper-lock coupler (732) therein (see schematic illustration of FIG. 47). Each end effector includes a mounting jacket (742) having an axially aligned tapered bore (744) extending through mounting jacket (742) and sized to snugly receive taper-lock coupler (732) therein (see FIG. 47). A pair of fluid conduits (746a, 746b) extend through mounting jacket (742), and are located so as to be in fluid communication with fluid passageways (736a, 736b) in coupler (732).

Harvesting end effector (740) comprises an elongate tube having mounting jacket (742) at its proximal end, and a tissue cutting section (750) adjacent its distal end. A pair of fluid conduits (748a, 748b) extend through the interior of harvesting end effector (740), and are in fluid communication (e.g., aligned) with fluid conduits (746a, 746b) in mounting jacket (742). Fluid conduits (748a, 748b) in harvesting end effector (740) extend from mounting jacket (742) into tissue cutting section (750). Tissue cutting section (750) comprises an enclosed cavity (752) adjacent the distal end of harvesting end effector (740). Fluid conduits (748a, 748b) extend away from the proximal end wall of (754) of cavity (752), and are in fluid communication with the interior of cavity (752). Harvesting end effector (740) has a tissue grating surface about tissue cutting section (750), which resembles a cheese grater. Thus, a plurality of openings (756) are provided in the outer wall of tissue cutting section (750) of harvesting end effector (740); and cutting teeth (758) extend away from the outer wall of tissue cutting section (750) so as to partially surround each of the openings (756). The distal end (760) of harvesting end effector (740) may comprise a sharp point for penetrating tissue. Tissue cutting section (750) of harvesting end effector (740) may be inserted into soft tissue in a patient (e.g., muscle) and then rotated such that cutting teeth (758) will cut off small pieces of tissue which will pass through openings (756) into cavity (752) within tissue cutting section (750). Cutting teeth (758) and openings (756) may be provided in any of a variety of shapes and configurations, including but not limited to slits, slots, triangular openings with sharp raised edges, diamond-shaped openings with sharp raised edges, cheese-grater configurations, etc.

In order to facilitate removal of the tissue fragments harvested into cavity (752) of tissue cutting section (750), as well as to combine the tissue fragments with a suitable carrier for later application within a lumen (e.g. a fistula) or other target site, a fluid composition is circulated through the harvesting end effector (740). A first reservoir (762) (depicted schematically in FIG. 47) is provided in housing (722). By way of example, lumen repair device (720) may be provided to an end-user with first reservoir (762) filled with a mixture of platelet-rich plasma (PRP) and saline. Of course, any other medical fluid component referred to herein (or combination of medical fluid components) may be used. A fluid outlet (764) is provided at the distal end of first reservoir (762), and a fluid inlet (766) is provided adjacent the proximal end of first reservoir (762). As further described herein, fluid media within first reservoir (762) may be expelled through outlet (764), circulated through the harvesting end effector (740) via fluid conduits (748a, 748b) and returned to first reservoir (762) through inlet (766).

Fluid media may be expelled from the first reservoir (762) by a variety of means.

In the present example, a plunger (768) is positioned within first reservoir (762), and may be urged distally so as to expel fluid media through outlet (764) while also simultaneously allowing returning fluid media (with suspended tissue fragments) to refill first reservoir (762) through inlet (766). As further described herein, this process may be reversed in order to expel fluid media comprising a suspension of viable tissue fragments in the opposite direction (i.e., out of first reservoir (762) through inlet (766)).

In order to expel fluid media into the interior of harvesting end effector (740) while harvesting end effector (740) is rotating, a rotatable fluid manifold (770) is also provided in housing (722), as shown schematically in FIG. 47. Fluid manifold (770) comprises a shaft operatively attached at its proximal end to motor (726), and attached at its distal end to coupler (732) and flange (734). Thus, when motor (726) is energized, fluid manifold shaft (770), coupler (732) and flange (734) will rotate, as well as any end effector attached to coupler (732). The shaft of fluid manifold (770) includes three fluid passageways (772, 774, 776) therein. Each fluid passageway (772, 774, 776) communicates at one end thereof with an orifice (773, 775, 777) on the outer surface of fluid manifold shaft (770). At the opposite end, first fluid passageway (772) is aligned with, and thus in fluid communication with, fluid passageway (736a) in flange (724). Second fluid passageway (774) at its opposite end is aligned with, and thus in fluid communication with, fluid passageway (736b) in flange (724). Third fluid passageway (776) extends through at least a portion of manifold shaft (770) along the longitudinal axis thereof. Third fluid passageway (776), at its distal end, is in fluid communication with a bore (778) extending through both flange (734) and coupler (732). Thus, fluid urged through third fluid passageway (776) may be expelled through the central bore (778) extending through coupler (732), and into the interior of an end effector attached thereto.

Fluid manifold shaft (770) is rotatably and sealingly mounted within a cylindrical cavity (780) provided in housing (722), as shown in FIG. 47. One or more O-rings or other seals may be provided between manifold shaft (770) and cavity (780). First, second and third annular channels (782, 784, 786) extend radially and circumferentially into the interior wall of cavity (780). Each channel (782, 784, 786) is located at a longitudinal position in common with a corresponding one of the orifices (773, 775, 777) provided on the outer surface of manifold shaft (770). In this manner, as fluid manifold shaft (770) is sealingly rotated within cylindrical cavity (780), each orifice (773, 775, 777) will remain in fluid communication with a corresponding one of the channels (782, 784, 786).

A first reservoir outlet line (788) is also provided, as shown schematically in FIG. 47, as well as a first reservoir inlet line (790). Outlet line (788) provides fluid communication between outlet (764) on first reservoir (762), and first channel (782) in cavity (780). Inlet line (790) provides fluid communication between inlet (766) on first reservoir (762), and second channel (784) in cavity (780). Accordingly, even while fluid manifold shaft (780) and harvesting end effector (740) attached to housing (722) are rotating, when plunger (768) is urged distally, fluid media within first reservoir (762) may be expelled through outlet (764), outlet line (788), first channel (782), first passageway (772), fluid passageway (736a) in flange (734), conduit (746a) in mounting jacket (742), and conduit (748a) extending through the harvesting end effector (740) into the interior of tissue cutting section (750) of harvesting end effector (740). At the same time, plunger (768) will pull a vacuum within first reservoir (762) in the space proximal to the plunger head such that fluid media and tissue fragments within tissue cutting section (750) will be pulled through conduit (748b) extending through the harvesting end effector (740), conduit (746b) in mounting jacket (742), fluid passageway (736b) in flange (734), second passageway (774), second channel (784), inlet line (790), and through inlet (766) into the first reservoir (762).

For purposes of harvesting tissue fragments, harvesting end effector (740) is attached to lumen repair device (720). Tissue cutting section (750) of harvesting end effector (740) is then inserted into soft tissue in a patient (e.g., muscle). Motor switch (730) is depressed in order to energize motor (726), which causes harvesting end effector (740) to rotate within the harvesting site. As rotating tissue cutting section (750) cuts tissue fragments, which are deposited within cavity (752) of tissue cutting section (750), plunger (768) is urged distally towards harvesting end effector (740). Distal movement of plunger (768) causes fluid media within first reservoir (762) to be circulated through cavity (752) of tissue cutting section (750). The fluid media is returned to first reservoir (762) with viable tissue fragments entrained therein. As further discussed herein, the thus created suspension of viable tissue fragments suspended in the fluid media contained within first reservoir (762) may be delivered into a fistula for repair.

Figure 48:
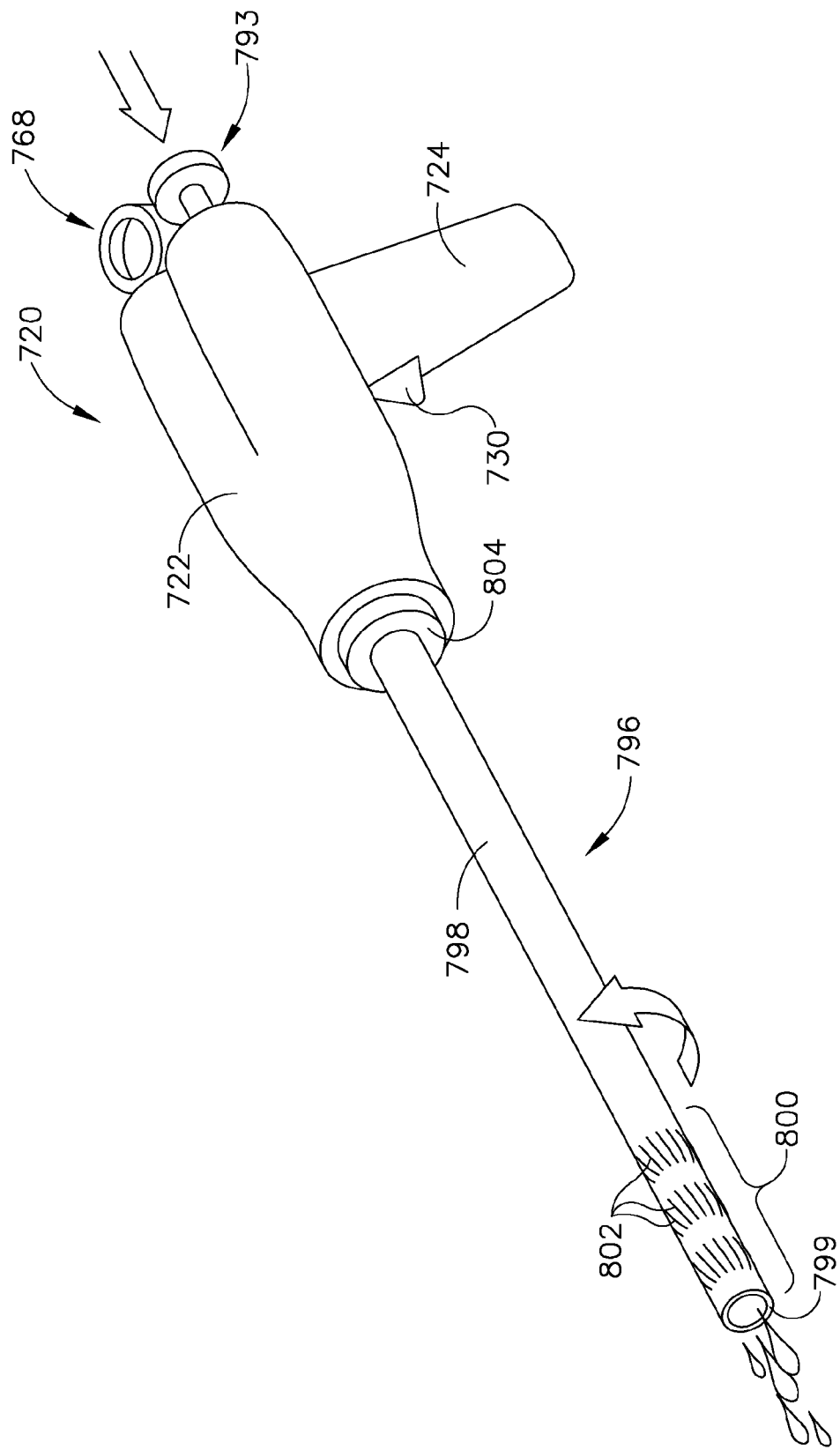
FIG. 48 depicts a schematic perspective view of the lumen repair device of FIG. 45, with a debridement end effector attached thereto.

In addition to harvesting tissue fragments and formulating a tissue repair composition comprising a suspension of those tissue fragments for subsequent delivery into a lumen such as an anal fistula, lumen repair device (720) may also be used to prepare a lumen for repair. Thus, a debridement end effector (796) may be operatively attached to housing (722), as shown in FIG. 48. Debridement end effector (796) comprises an elongate hollow tube (798) having an open distal end (799) and a tissue debridement section (800) adjacent distal end (799). Tissue debridement section (800) includes a plurality of vents (802) arrayed about the outer circumference of tissue debridement section (800). Vents (802) include at least one raised edge for tissue debridement. A mounting jacket (804) is located at the proximal end of hollow tube (798), and is configured similar to mounting jacket (742) on harvesting end effector (740). While mounting jacket (804) includes a central bore similar to bore (744) in mounting jacket (742), the fluid conduits (746a, 746b) of mounting jacket (742) are omitted in mounting jacket (804).

As shown in the schematic illustration of FIG. 47, a second media reservoir (792) is provided in housing (722), and includes a plunger (793) for expelling the contents of the second reservoir (792). A fluid outlet (794) is provided at the distal end of second reservoir (792), as well as a second reservoir outlet line (795), as shown schematically in FIG. 47. Second reservoir outlet line (795) provides fluid communication between outlet (794) on second reservoir (792), and third channel (786) in cavity (780). Accordingly, even while fluid manifold shaft (780) and debridement end effector (796) attached to housing (722) are rotating, when plunger (793) is urged distally, fluid media within second reservoir (792) may be expelled through outlet (794), outlet line (795), third channel (786), third passageway (776), bore (778) in coupler (732), and into the interior of debridement end effector (796). The fluid media from second reservoir (792) will be urged through the length of debridement end effector (796) and be expelled from the open distal end (799) thereof, as well as through vents (802) in order to flush the lining of the fistula or other lumen.

The second media reservoir (792) may be filled with a variety of compositions, such as a sterile saline solution.

Various other treatment or cleaning components may be included, such as antibiotics or any other medical fluid component(s) referred to herein. By way of example, after tissue fragments have been harvested from a patient using harvesting end effector (740) so as to formulate a tissue repair composition contained in first reservoir (762) (with plunger (768) fully depressed distally as shown in FIG. 46), harvesting end effector (740) is replaced with debridement end effector (796). The distal end (799) of debridement end effector (796) is inserted into a fistula until the distal end (799) is located adjacent the interior (or distal) opening of the fistula. Motor switch (730) is depressed in order to energize motor (726), which causes debridement end effector (796) to rotate within the fistula. Tissue debridement section (800) will scrape away the endothelial lining of the fistula as well as granulation tissue which may be present. While the user continues to depress motor switch (730), the debridement end effector (796) is slowly withdrawn from the fistula such that the entire interior length of the fistula is debrided. In some other versions, debridement end effector (796) is rotated manually and/or reciprocated within the fistula tract. While the debridement end effector (796) is being withdrawn from the fistula, or just prior to the distal end (799) thereof being removed from the external (or proximal) opening of the fistula, plunger (793) is urged distally as shown in FIG. 48 in order to expel the fluid media from second reservoir (792) through open distal end (799) of the debridement end effector (796) into the fistula. The fluid media will flush tissue debris from the fistula (through the interior or distal opening of the fistula), thus preparing the fistula for repair.

In order to repair a fistula or other lumen, a delivery probe such as any of the various ones described previously herein may be attached to coupler (732), with the interior lumen of the delivery probe in fluid communication with the inlet (766) of first media reservoir (762) via fluid passageway (736*b*) in coupler (732). With the delivery probe positioned in the fistula, plunger (768) of first reservoir (762) is urged proximally (away from the delivery probe), thus expelling the tissue repair composition in first reservoir (762) through the delivery probe and out the distal end thereof for delivery into the fistula.

Figure 49:
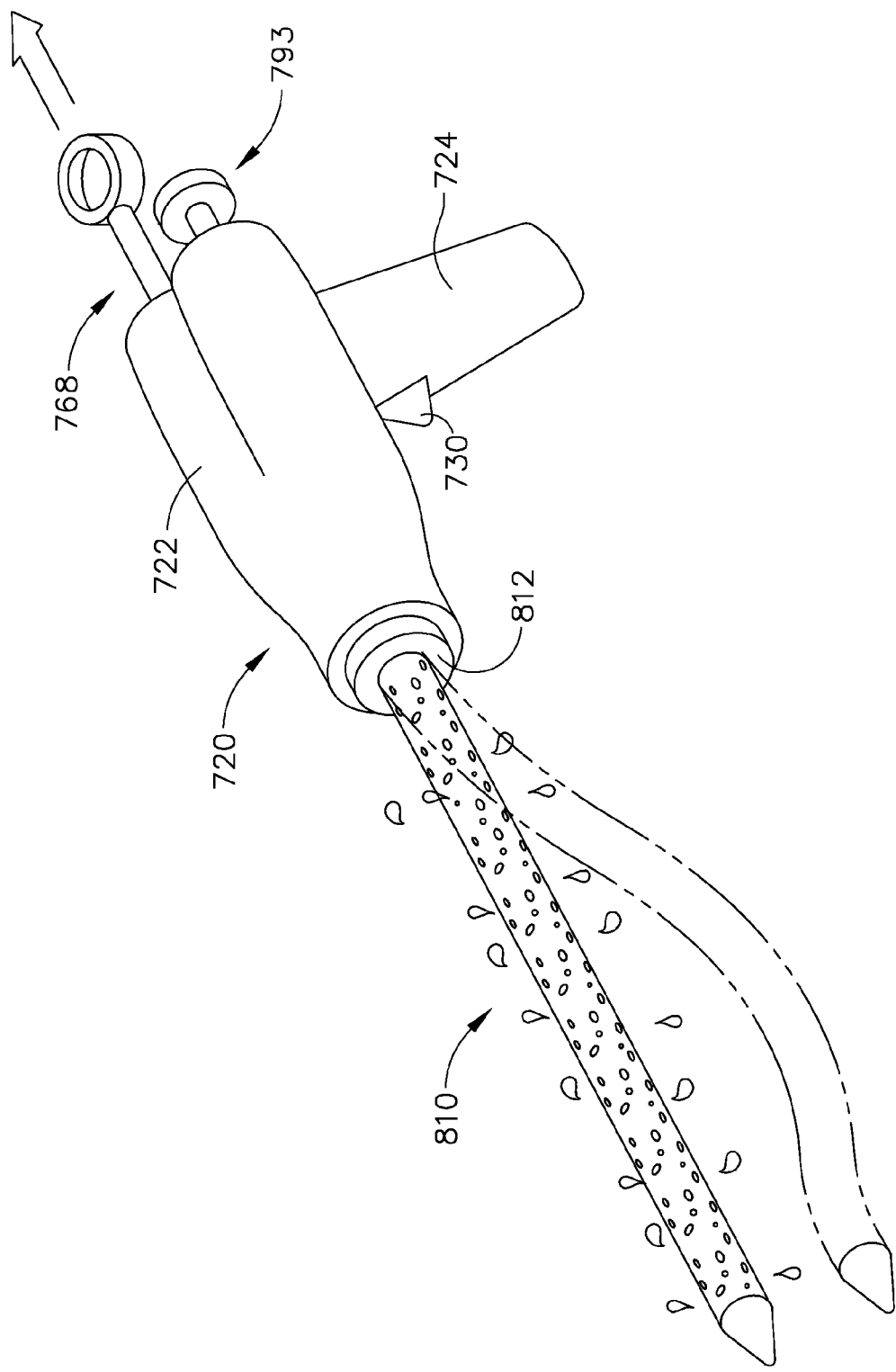
FIG. 49 depicts a schematic perspective view of the lumen repair device of FIG. 45, with a scaffold plug attached thereto.
Figure 50:
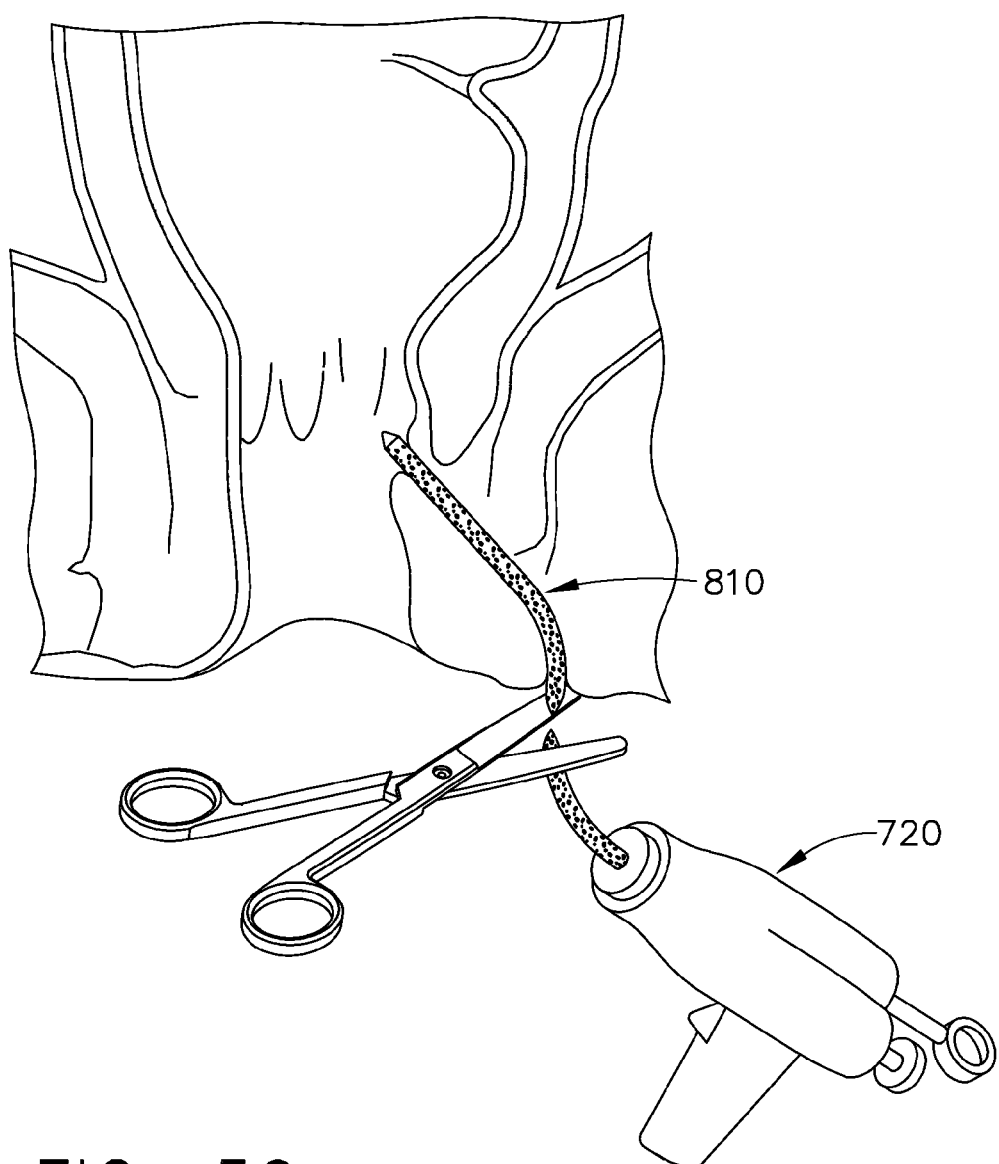
FIG. 50 depicts a schematic view of the lumen repair device of FIG. 49 being used to repair an anal fistula.

Alternatively, and as shown in FIGS. 49-50, a biocompatible scaffold plug (810) may be attached to coupler (732) of lumen repair device (720). Elongate scaffold plug (810) comprises a biocompatible, bioresorbable, flexible, porous material, such as the various materials and compositions described in U.S. Pub. No. 2004/0078090, the disclosure of which is incorporated by reference herein. By way of example, scaffold plug (810) may comprise oxidized regenerated cellulose (e.g., SURGICEL by Ethicon, Inc., Somerville, N.J.), lyophilized collagen (e.g., INSTAT by Ethicon, Inc., Somerville, N.J.), fibrin, elastin, and/or one or more bioabsorbable synthetic materials such as polylactide (PLA), polyglycolide (PGA), polycaprolactone (PCL), polydioxanone (PDO) and their copolymers. Such material may provide sufficient flexibility to allow scaffold plug (810) to follow a non-linear path of a fistula; yet have enough strength to allow scaffold plug (810) to be inserted in the fistula without buckling to an unsuitable degree. Scaffold plug (810) has a hollow lumen extending through nearly its entire length (not shown), and also includes a mounting jacket (812) at its proximal end. Mounting jacket (812) is configured similar to mounting jacket (742) on harvesting end effector (740), and includes a central bore similar to bore (744) in mounting jacket (742), as well as a fluid conduit similar to fluid conduit (746*b*) of mounting jacket (742). This fluid conduit within mounting jacket (812) is configured to provide fluid communication between the interior lumen of the through scaffold plug (810) and the inlet (766) of first media reservoir (762) via fluid passageway (736*b*) in coupler (732). Thus, when plunger (768) of first reservoir (762) is urged proximally (away from the scaffold plug (810) attached to coupler (732)), the tissue repair composition in first reservoir (762) will be expelled into the interior lumen of the scaffold plug (810).

In order to repair a previously debrided fistula, a scaffold plug (810) is attached to coupler (732) of lumen repair device (730). Scaffold plug (810) is then inserted into the fistula, as shown in FIG. 50. Plunger (768) of first reservoir (762) is urged proximally (as shown in FIG. 49), causing the tissue repair composition in first reservoir (762) comprising previously-harvested tissue fragments suspended in a carrier such as PRP and saline, to fill the lumen within scaffold plug (810). The tissue repair composition will migrate radially outward through the thickness of plug (810). The scaffold plug (810) may then be cut to the appropriate length, as shown in FIG. 50. Thereafter, as the scaffold plug is resorbed, viable cells in the tissue fragments will proliferate and integrate with surrounding tissue in the fistula, thereby repairing the fistula. The PRP will also aid in healing and repair by activating platelets which create a fibrin clot in the fistula. Other suitable variations, components, features, configurations, and operabilities of repair device (720) will be apparent to those of ordinary skill in the art in view of the teachings herein.

IX. Exemplary Integrated Harvesting, Formulating, and Delivering Lumen Repair Device FIGS. 51-56 depict still another example of a lumen repair device (820) that may be used, for example, to repair a fistula or to perform some other procedure at some other site. Like previous examples, lumen repair device (820) may be used to harvest viable tissue specimens, morcellate those tissue specimens into smaller tissue fragments, mix the tissue fragments with a suitable carrier to form a tissue repair composition, and then deliver that tissue repair composition through an end effector into a fistula or other lumen for repair (healing and tissue regeneration). In the present example, lumen repair device (820) includes a housing (822) having a handle (824) extending downwardly away from the housing (822). An end effector comprising a transport tube (826) extends distally away from housing (822), and is fixedly mounted thereto. Transport tube (826) is hollow (and thus provides a fluid conduit therein), a mincing transport member (828) extends through the interior of transport tube (826) and is rotatable within transport tube (826), as will be described in greater detail below. Transport tube (826) is open at both ends. The distal end (834) of transport tube (826) is configured such that a variety of end effector tips may be operatively and removably attached thereto. Lumen repair device (820) may be provided as a kit having a plurality of different end effector tips, as further described herein. The proximal end (836) of transport tube (826) is positioned within a mixing chamber (838) provided in housing (822). Transport tube (826) is configured so as to have a transport section (900) located adjacent distal end (834), and a mincing section (902) located between transport section (900) and mixing chamber (838).

Mincing transport member (828) of the present example comprises an elongate shaft (830) running along the length of mincing transport member (828). Mincing transport member (828) is rotatable within transport tube (826) via shaft (830) as will be described in greater detail below. In particular, the proximal end of shaft (830) is operatively coupled to an auger drive shaft (840) located within mixing chamber (838), such as by swage fit into the end of auger drive shaft (840). Thus, as auger drive shaft (840) is rotated, mincing transport member (828) will also rotate within transport tube (826). A motor (842) is provided in housing (822) for, among other things, driving auger drive shaft (840) via a plurality of gears, as further described below.

A distal portion of mincing transport member (828) includes a conveying auger flight (832) that is helically wrapped about shaft (830). Conveying auger flight (832) of this example has substantially constant pitch and diameter, though some alternative versions may have variable pitch and/or other properties. As described further herein, mincing transport member (828) may be rotated in either direction in order to transport tissue pieces and/or medical fluid components proximally or distally through transport tube (826). Conveying auger flight (832) may also further cut harvested tissue pieces into smaller pieces. The harvesting of tissue pieces will be described in greater detail below.

Figure 54:
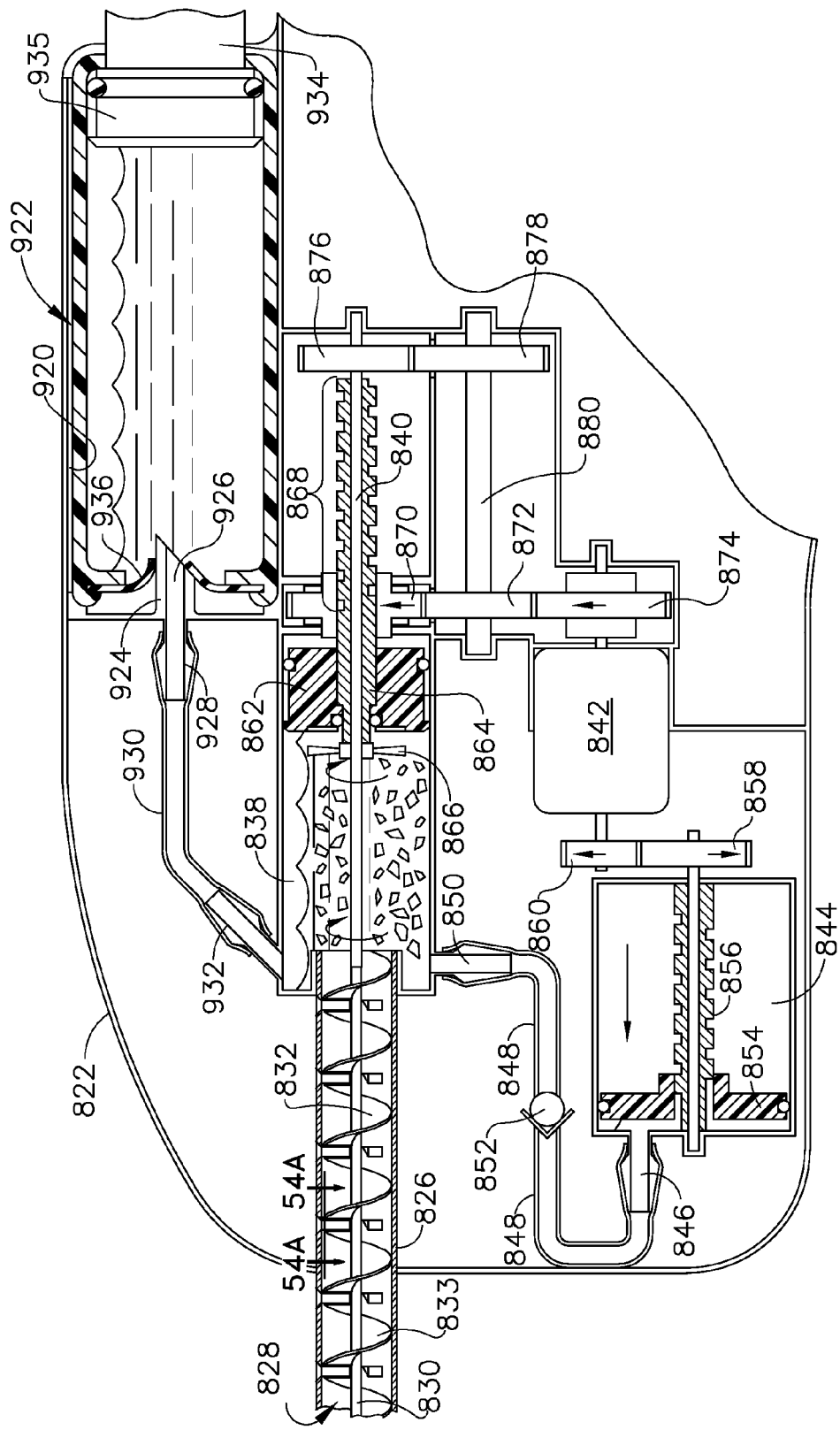
FIG. 54 depicts an enlarged partial cross-sectional view of a portion of the lumen repair device shown in FIG. 51, with media from the reservoir expelled into the mixing chamber and combined with tissue fragments delivered into the mixing chamber through the transport tube.
Figure 54A:
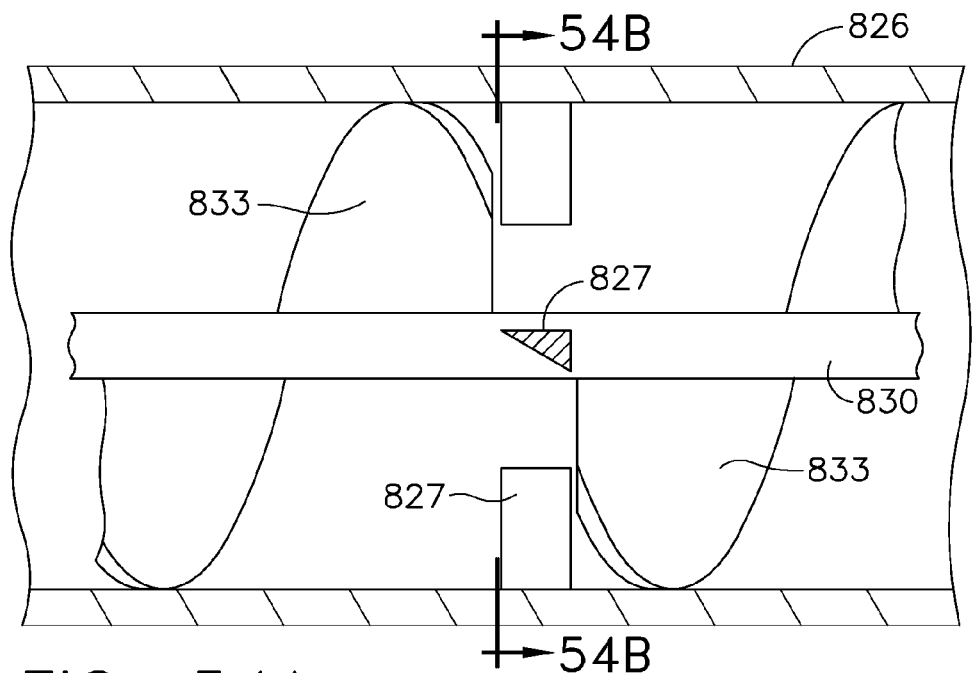
FIG. 54A depicts a cross-sectional view taken along line 54A-54A of FIG. 54.
Figure 54B:
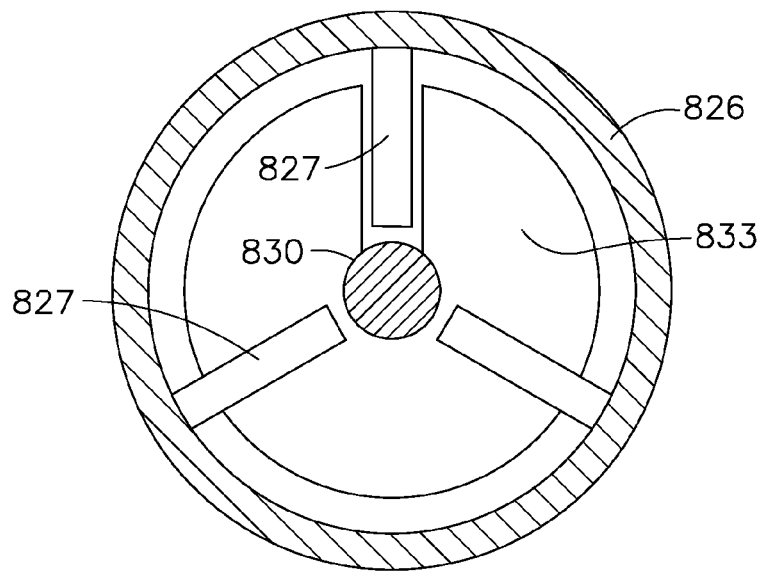
FIG. 54B depicts a cross-sectional view taken along line 54B-54B of FIG. 54A.

A proximal portion of mincing transport member (828) comprises a plurality of broken auger blade sections (833) that are disposed about shaft (830). Broken auger blade sections (833) are positioned along a mincing section (902) of transport tube (826) in which a plurality of projections (827) extend radially inwardly. In particular, and as best seen in FIGS. 54A-54B, projections (827) comprise inwardly projecting cutting pins that are fixed to transport tube (826), such that projections (827) remain stationary while mincing transport member (828) rotates within transport tube (826). As can be seen in FIG. 54A in particular, projections (827) are positioned at gaps between adjacent broken auger blade sections (833), such that projections (827) do not prevent mincing transport member (828) from rotating.

In the present example, projections (827) are provided in sets of three at each gap between adjacent broken auger blade sections (833), with projections (827) in each set being equidistantly spaced from each other about the circumference of transport tube (826). Of course, any other suitable number of projections (827) may be provided at each gap between adjacent broken auger blade sections (833). As tissue is conveyed proximally through transport tube (826) while mincing transport member (828) rotates, projections (827) and broken auger blade sections (833) cooperate to mince the tissue, such that the tissue becomes further minced as it progresses proximally through the proximal portion of transport tube (826). In addition, broken auger blade sections (833) continue to convey the minced tissue proximally until the minced tissue ultimately reaches mixing chamber (838) of housing (822). Of course, a variety of other components or features may be provided within transport tube (826) to mince and/or convey tissue.

As shown in FIGS. 51, 54, and 55-56, a fluid reservoir (844) is also provided in housing (822), and includes an outlet pipe (846) at the distal end of the reservoir (844). Lumen repair device (820) may be supplied to end-users with reservoir (844) filled with a suitable carrier for use in formulating a tissue repair composition. For example, reservoir (844) may contain any of the various types of fluids referred to herein, including combinations of such fluids. A first fluid transfer conduit (848) provides fluid communication between outlet pipe (846) of reservoir (844) and a first inlet pipe (850) on mixing chamber (838). Fluid may be expelled from reservoir (844) through first transfer conduit (848) into mixing chamber (838) as will be described in greater detail below. A check valve (852) is also provided on first transfer conduit (848) to prevent the flow of fluid from mixing chamber (838) into reservoir (844), though it should be understood that check valve (852) is merely optional like every other component described herein. A plunger (854) is positioned in reservoir (844) and includes a threaded bore extending through the center of the plunger (854). Plunger (854) is mounted on a threaded shaft (856) extending axially through the reservoir (844). When shaft (856) is rotated counterclockwise (viewed from proximal end to distal end), plunger (854) is advanced distally from a proximal position (see FIG. 51) towards outlet pipe (846) to reach a distal position (see FIG. 54), such that fluid is expelled from reservoir (844) into mixing chamber (838). One or more rails, tracks, or other features may be engaged with plunger (854) to prevent plunger (854) from rotating within reservoir (844) while still allowing plunger (854) to translate within reservoir (844), thus providing a rotational ground while threaded shaft (856) rotates. In addition, threaded shaft (856) and plunger (854) of the present example are configured such that threaded shaft (856) "freewheels" relative to plunger (854) once plunger (854) reaches the distal position shown in FIG. 54. In other words, threaded shaft (856) may rotate freely relative to plunger (854) as plunger (854) remains at the distal position.

A first gear (858) is provided on the proximal end of threaded shaft (856), external to reservoir (844). First gear (858) is in meshing relationship with a second gear (860) which is operatively attached to a drive shaft of motor (842). Thus, as the motor rotates second gear (860) clockwise, first gear (858) and threaded shaft (856) will rotate counterclockwise in order to drive plunger (854) distally to expel fluid into mixing chamber (838).

The contents of mixing chamber (838) may be expelled into the interior of transport tube (826) through the open proximal end (836) of the transport tube (826) in a similar fashion. A plunger (862) is also provided in mixing chamber (838). As plunger is urged distally from a proximal position (see FIG. 54) towards transport tube (826) (see FIG. 55), fluid (including minced tissue fragments) will be expelled from mixing chamber (838) into transport tube (826). In order to move plunger (862), the plunger (862) is fixedly mounted on an axle (864) adjacent the distal end of the axle (864). The axle (864) also includes a threaded portion (868) located proximally from plunger (862). Threaded portion (868) of axle (864) extends through the threaded axial bore of a third gear (870), such that, as third gear (870) is rotated, axle (864) is axially advanced into or out of mixing chamber (838) in order to drive plunger (862). In other words, the rotation of third gear (870) is translated into longitudinal motion of axle (864) (which does not rotate, and may be rotationally grounded by one or more rails, tracks, or other features). In the present example, third gear (870) is meshed with a fourth gear (872) which is also meshed with fifth gear (874). Fifth gear (874) is operatively attached to a drive shaft of motor (842), such that motor (842) may be used to rotate axle (864), and hence advance plunger (862). In the example shown, motor (842) may be driven in either direction, thus allowing plunger (862) to be axially displaced towards either the distal or proximal ends of mixing chamber (838).

Auger drive shaft (840) extends through the interior of axle (864), and is rotatable within and relative to axle (864). An impeller (866) is fixedly mounted to the auger drive shaft (840), adjacent the distal end of axle (864). As drive shaft (840) is rotated, impeller (866) will rotate to mix the contents of mixing chamber (838). Auger drive shaft (840) extends beyond the proximal end of axle (864), and a sixth gear (876) is fixedly mounted to the proximal end of auger drive shaft (840). Sixth gear (876) is in meshing relationship with a seventh gear (878), and the seventh gear (878) is fixedly mounted on one end of a rotatable connector rod (880). Fourth gear (872) is fixedly mounted on the opposite end of connector rod (880). Thus, when fifth gear (874) is rotated by motor (842), fourth gear (872), connector rod (880), seventh gear (878) and sixth gear (876) will also rotate, with sixth gear (876) rotating auger drive shaft (840), which is fixedly attached thereto. Of course, a variety of other components, features and arrangements may be used to provide translation of plungers (854, 862), rotation of auger drive shaft (840), and/or rotation of impeller (866).

Figure 52:
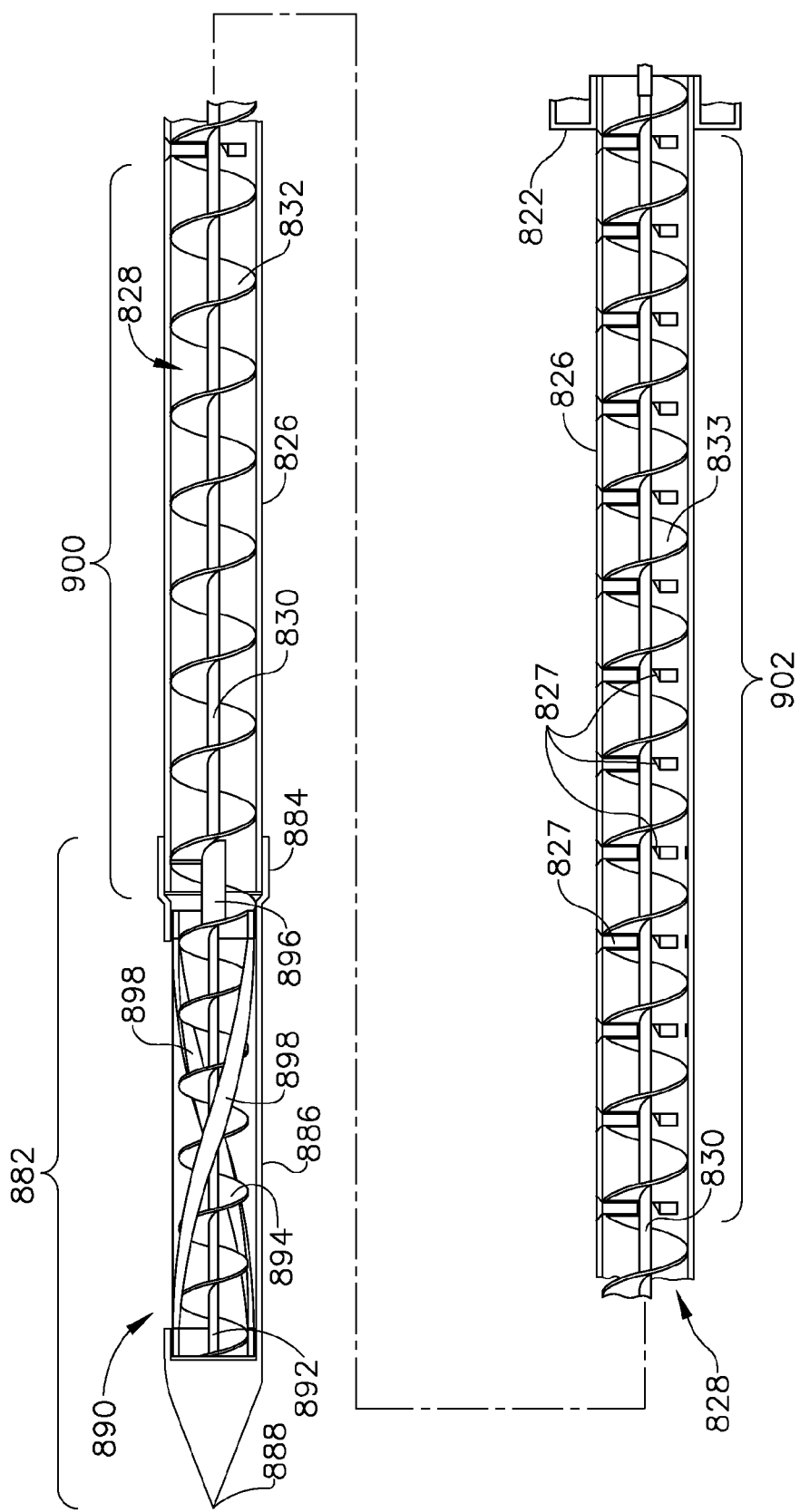
FIG. 52 is partial cross-sectional view of the transport tube of the lumen repair device shown in FIG. 51, along with a harvesting end effector tip attached thereto.
Figure 53:
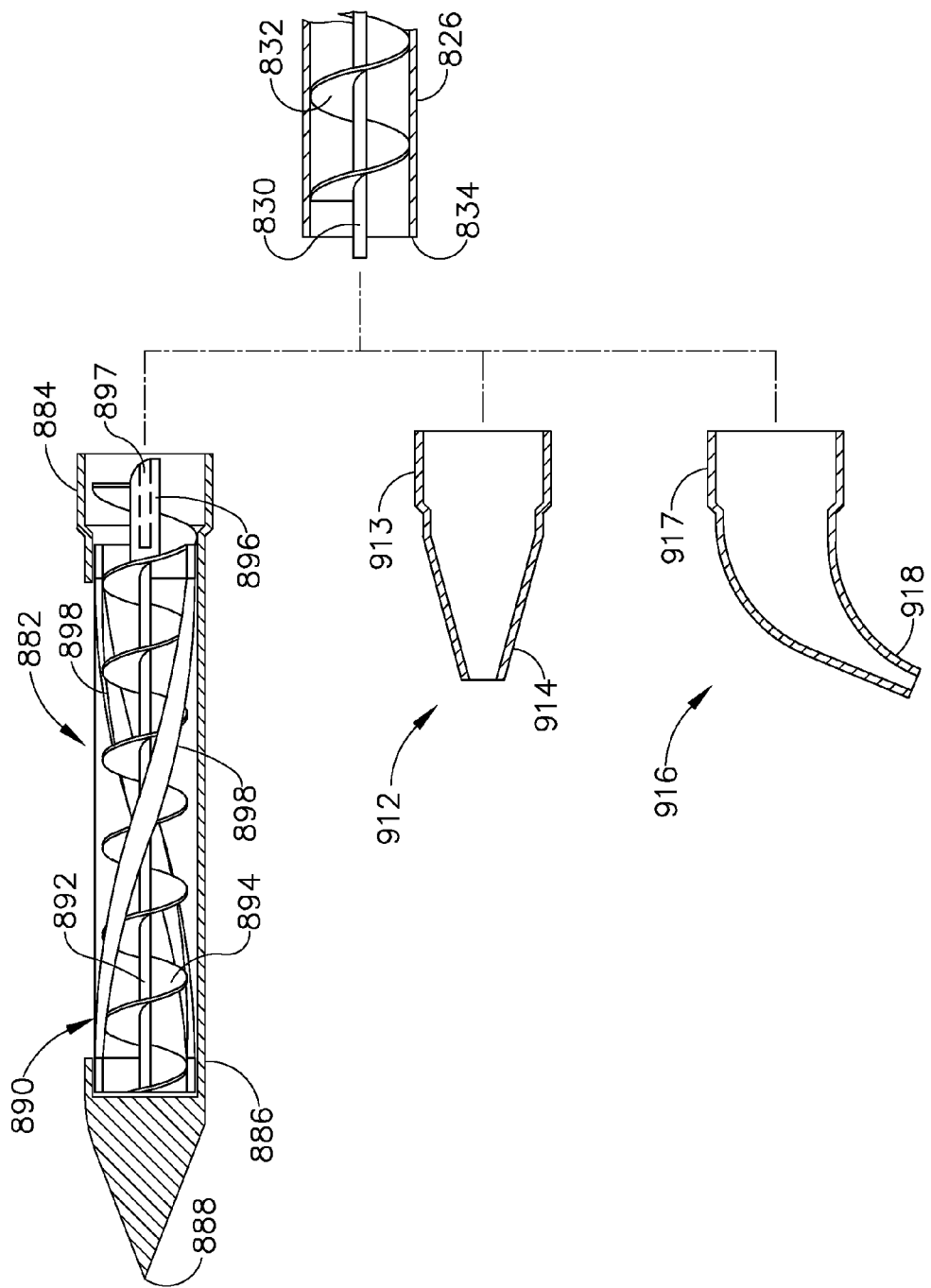
FIG. 53 depicts a partial cross-sectional view of three different end effector tips for attachment to the distal end of the transport tube of the lumen repair device shown in FIG. 51.

A variety of end effector tips may be attached to the distal end (834) of transport tube (826). By way of example, FIGS. 52-53 depict a harvesting end effector tip (882) that is attachable to the distal end (834) of transport tube (826), such that harvesting end effector tip (882) provides a tissue cutting section on the distal end of the transport tube (826). Like other end effector tips, harvesting end effector tip (882) includes an enlarged proximal end portion (884) sized and configured to friction fit over the distal end (834) of transport tube (826). Of course other types of connectors and couplings may be used to attach end effector tips to transport tube (826). Harvesting end effector (882) comprises an outer tube (886) having a sharp distal tip (888) configured for penetrating tissue and a transverse tissue receiving port (890) proximal to distal tip (888). An auger comprising an auger shaft (892) and an auger flight (894) extending radially away from auger shaft (892) extends though the length of outer tube (886). As best seen in FIG. 53, a coupling sleeve (896) is provided at the proximal end of auger shaft (892), and coupling sleeve (896) includes a tapered bore (897) sized to fittingly receive the distal end of elongate shaft (830) therein. Thus, harvesting end effector tip (882) may be attached to the distal end of transport tube (826), with the distal end of elongate shaft (830) snugly received in tapered bore (897) of coupling sleeve (896). In this manner, when mincing transport member (828) is rotated within transport tube (826), the auger in harvesting end effector tip (882) will also rotate.

A pair of helically-extending cutting blades (898) are supported by auger flight (894) and extend about the external circumference of the auger, as shown. Helical blades (898) have an effective longitudinal length and position corresponding with the length and position of transverse tissue receiving port (890). In addition, helical blades (898) are configured such that helical blades (898) will sever tissue that is prolapsed through transverse tissue receiving port (890) while shafts (830, 892) are rotating. In particular, helical blades (898) cooperate with longitudinally extending lateral edges (not shown) of outer tube (886) that partially define transverse tissue receiving port (890), such as by shearing the tissue in a manner similar to a manual "reel mower" type of lawnmower blade shearing a blade of grass. Tissue pieces that are severed by helical blades (898) are conveyed proximally through outer tube (886) by auger flight (894) while shafts (830, 892) are rotating; then proximally through transport tube (826) by auger flight (832) and auger blade sections (833) while shaft (830) continues to rotate. The harvested tissue specimens are thus eventually communicated into mixing chamber (838) being minced in mincing section (902) of transport tube (826) along the way as described above.

Figure 51:
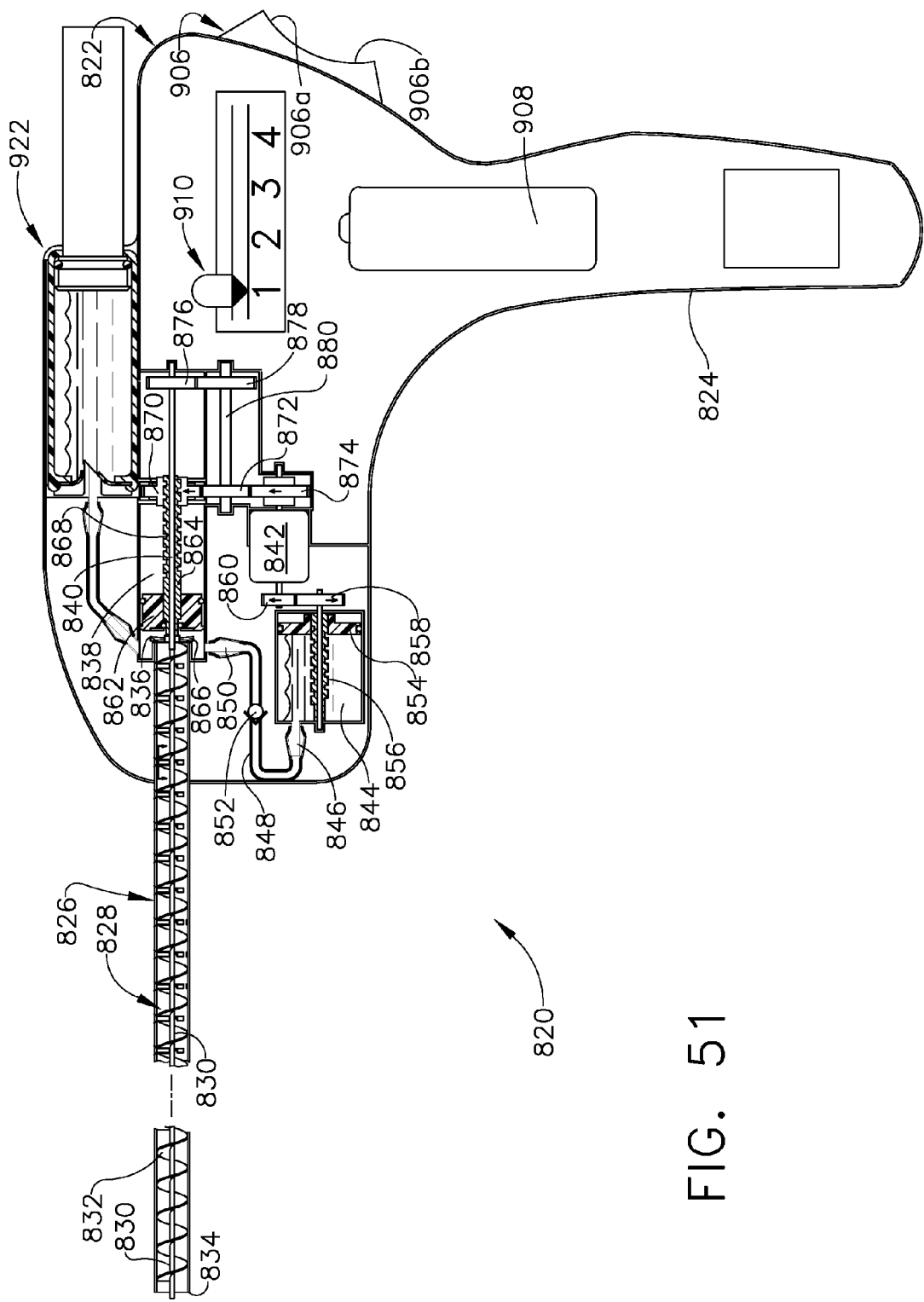
FIG. 51 depicts a partial cross-sectional view of another exemplary lumen repair device.

As motor (842) rotates in order to drive mincing transport member (828) and deliver harvested tissue fragments into mixing chamber (838), motor (842) also causes plunger (854) to move distally within reservoir (844) and expel the fluid media therein into mixing chamber (838), where the fluid media is mixed with the tissue fragments by rotating impeller (866). As shown in FIG. 51, an actuator (906) is provided on housing (822), and, when depressed, causes motor (842) to rotate. Actuator (906) comprises a two-way switch, such that depressing an upper portion (906a) causes motor (842) to rotate in one direction (e.g., for harvesting of tissue), and depressing lower portion (906b) of the actuator causes the motor (842) to rotate in the opposite direction (e.g., for dispensation of a medical fluid). A speed control (910) is also provided on housing (822) and may be used to control the speed of motor (842). For instance, the user may wish to vary the speed of motor (842) based on the task being performed (e.g., tissue harvesting or medical fluid administration), based on the tissue being harvested and minced (e.g., different tissue densities), and/or based on various other factors. In the example shown, speed control (910) provides four selectable speeds, though any suitable number of speeds may be provided, including just one single speed. A battery (908) in handle (824) provides power to motor (842), though motor (842) may alternatively receive power from any type of source.

Once tissue fragments have been harvested using harvesting end effector tip (882), and are deposited into mixing chamber (838) along with fluid media to formulate a tissue repair composition or medical fluid contained in mixing chamber (838), the harvesting end effector tip (882) is replaced with a delivery end effector tip. Two exemplary delivery tips (912, 916) are shown in FIG. 53. Both delivery tips (912, 916) are hollow such that a tissue repair composition may be expelled therethrough, and ejected from the distal end of the delivery tip (912, 916) at the desired location. First delivery tip (912) has an enlarged proximal end portion (913) sized and configured to friction fit over the distal end (834) of transport tube (826). Similarly, second delivery tip (916) has an enlarged proximal end portion (917) sized and configured to friction fit over the distal end (834) of transport tube (826). Both delivery tips (912, 916) further include a tapered distal end portion (914, 918), having an orifice through which a tissue repair composition is expelled. First delivery tip (912) further has a straight orientation, while second delivery tip (916) is curved in order to facilitate delivery of a tissue repair composition to difficult to reach locations. Of course a variety of other types of delivery tips may be provided, such as spray tips (e.g., with a nozzle) or tips configured to spread the composition onto a wider area (e.g., similar to the distal end of delivery probe (508) in FIG. 27).

Figure 55:
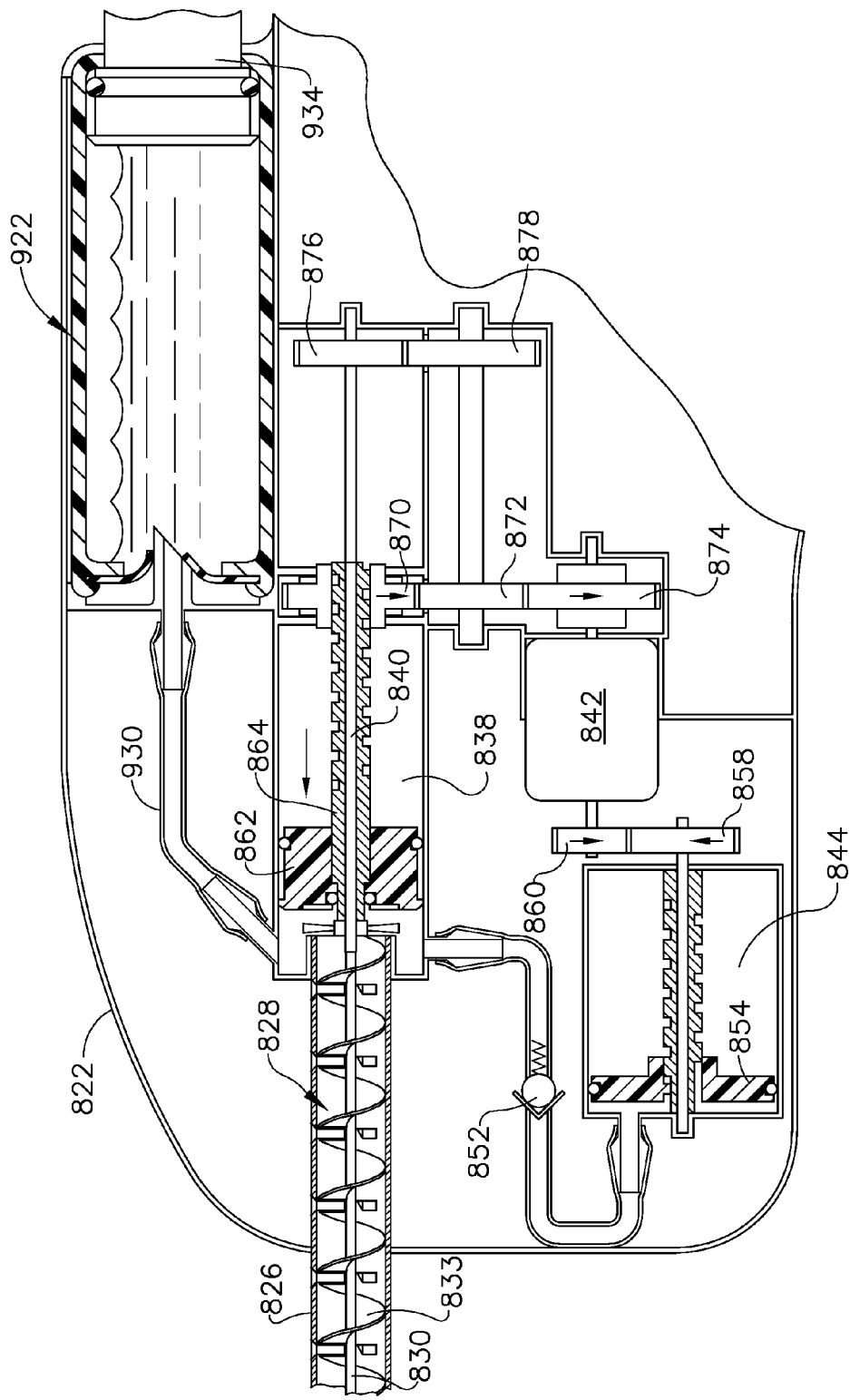
FIG. 55 is similar to FIG. 54, with a tissue repair composition expelled from the mixing chamber into the transport tube.

With a suitable delivery tip attached to the distal end of transport tube (826), and the distal end of the delivery tip positioned to delivery fluid at the desire location, motor (842) is actuated so as to rotate in the direction opposite to that used to harvest tissue specimens and transport those specimens into the mixing chamber (838). As shown in FIG. 55, motor (842) will rotate the various gears within housing (822) causing plunger (862) to move distally towards transport tube (826) and expel the tissue repair composition in mixing chamber (838) into transport tube (826). Plunger (854) will also move proximally within reservoir (844). However, check valve (852) will prevent the tissue repair composition from flowing into reservoir (844). In addition, impeller (866) will rotate so as to further mix the tissue repair composition. The pressure supplied by the distal movement of plunger (862) as well as the clockwise rotation of mincing transport member (828) will cause the tissue repair composition to be transported distally through transport tube (826). In mincing section (902) of the transport tube (826), the tissue fragments will be minced even smaller, and the tissue repair composition comprising a suspension of the tissue fragments will be expelled through the orifice at the distal end of the delivery tip (912, 916) and applied to the repair location (e.g., within a fistula).

Following delivery of the tissue repair composition, the lumen repair device may be cleaned using a saline solution or other suitable fluid from a media cartridge. In the present example, a cartridge-receiving chamber (920) is provided in housing (822), and is configured for alignably and detachably receiving a media cartridge (922) therein. As shown in FIG. 54, chamber (920) is located within housing (822) above, and proximal to mixing chamber (838). A nipple (924) extends proximally away from the distal end wall of cartridge-receiving chamber (920). Nipple (924) has a sharp proximal tip, and the passageway (926) extending longitudinally through nipple (924) communicates with an outlet pipe (928) extending away from chamber (920). A cleaning tube (930) provides fluid communication between outlet pipe (928) and a cleaning inlet pipe (932) extending away from a distal region of mixing chamber (838), in fluid communication therewith. Thus, fluid expelled from a cartridge (922) mounted within chamber (920) will be delivered into mixing chamber (838), from which it may be expelled through transfer tube (826).

Media cartridge (922) is similar in construction to cartridge (610) shown in FIG. 33, and comprises a cylindrical barrel having proximal and distal orifices in the proximal and distal end walls of the barrel. A plunger (934) extends through the proximal orifice of the barrel such that the plunger head (935) is located within the barrel, as shown. While the distal end of cartridge (922) may have a coupling configured for attachment to a corresponding connector on, for example, nipple (924), in the present example a resilient, flexible seal (936) is provided over the distal orifice of the barrel (like media cartridge (610) described previously).

Figure 56:
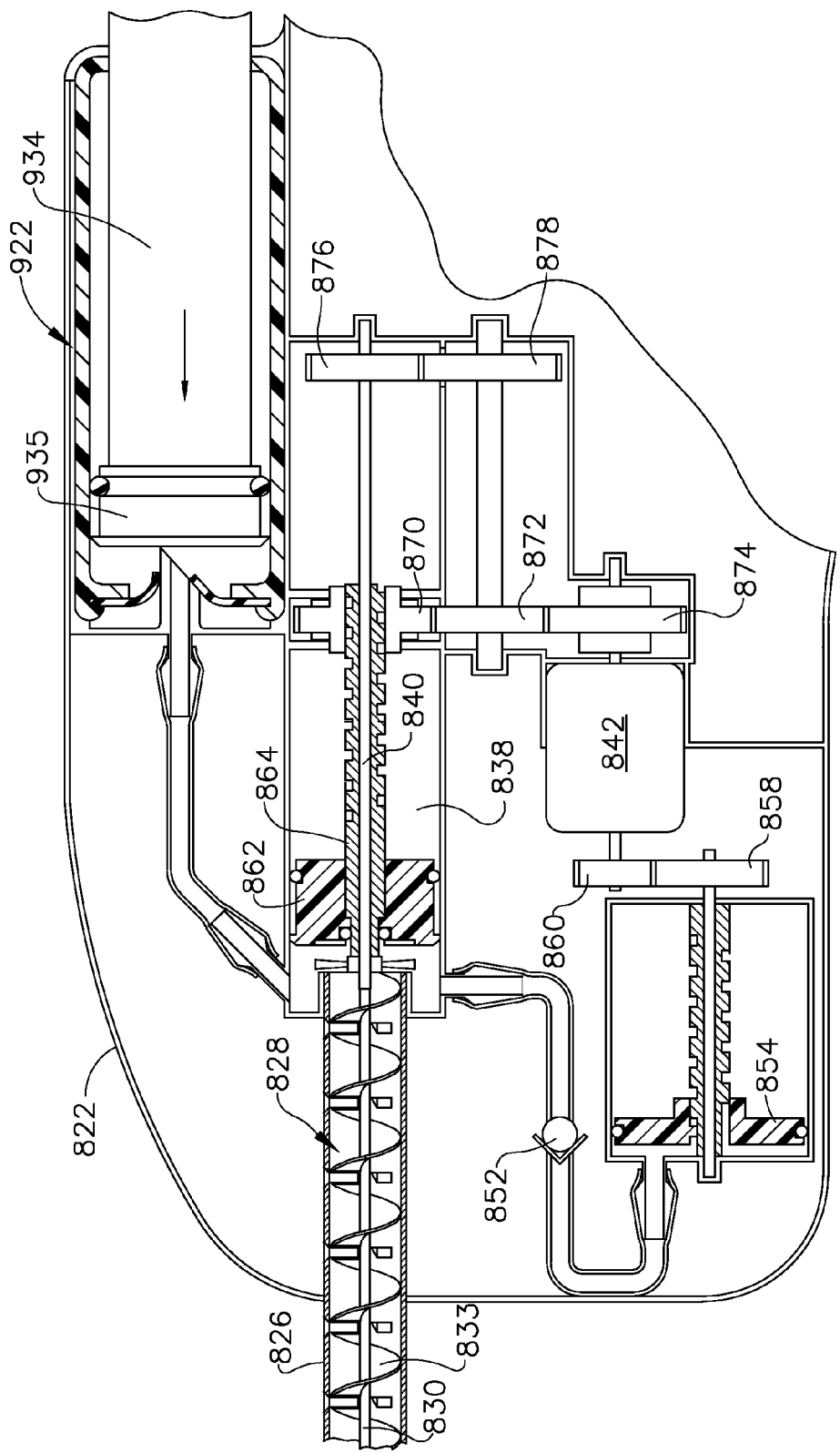
FIG. 56 is similar to FIG. 55, with the contents of the media cartridge expelled therefrom into the transport tube.

Media cartridge (922) is inserted into cartridge-receiving chamber (920) such that nipple (924) penetrates seal (936) (e.g., through a slit or other feature formed through seal (936), etc.). Thus, when plunger (934) is urged distally (i.e., towards transport tube (826)) as shown in FIG. 56, media contained within cartridge (922) will be expelled through tube (930) into mixing chamber (838). A user may manually push plunger (934) while actuating motor (842) in order to retract plunger (862) in mixing chamber (838). Once mixing chamber (838) has been filled with media such as a saline solution or other type of cleaning solution expelled from cartridge (922), the motor direction may be reversed in order to expel the saline or cleaning solution into the interior of transport tube (826). A check valve may also be provided on tube (930) in order to prevent flow from mixing chamber (838) back into cartridge (922). The solution will be urged through transport tube (826) in order to clean tissue fragments and other materials from inside transport tube (826). If desired, a delivery end effector tip may be positioned on the distal end of transport tube (826) so that the saline or other cleaning solution may even be applied to a location within the patient for cleaning and/or other purposes (e.g., at or within the biopsy site). It should also be understood that media cartridge (922) may include a medical fluid component, and that its use is not necessarily limited to cleaning lumen repair device (820) and/or a target site in a patient. Other suitable variations, components, features, configurations, and operabilities of repair device (820) will be apparent to those of ordinary skill in the art in view of the teachings herein.

X. Exemplary Device for Coextruding a Fistula Repair Plug

Figure 57:
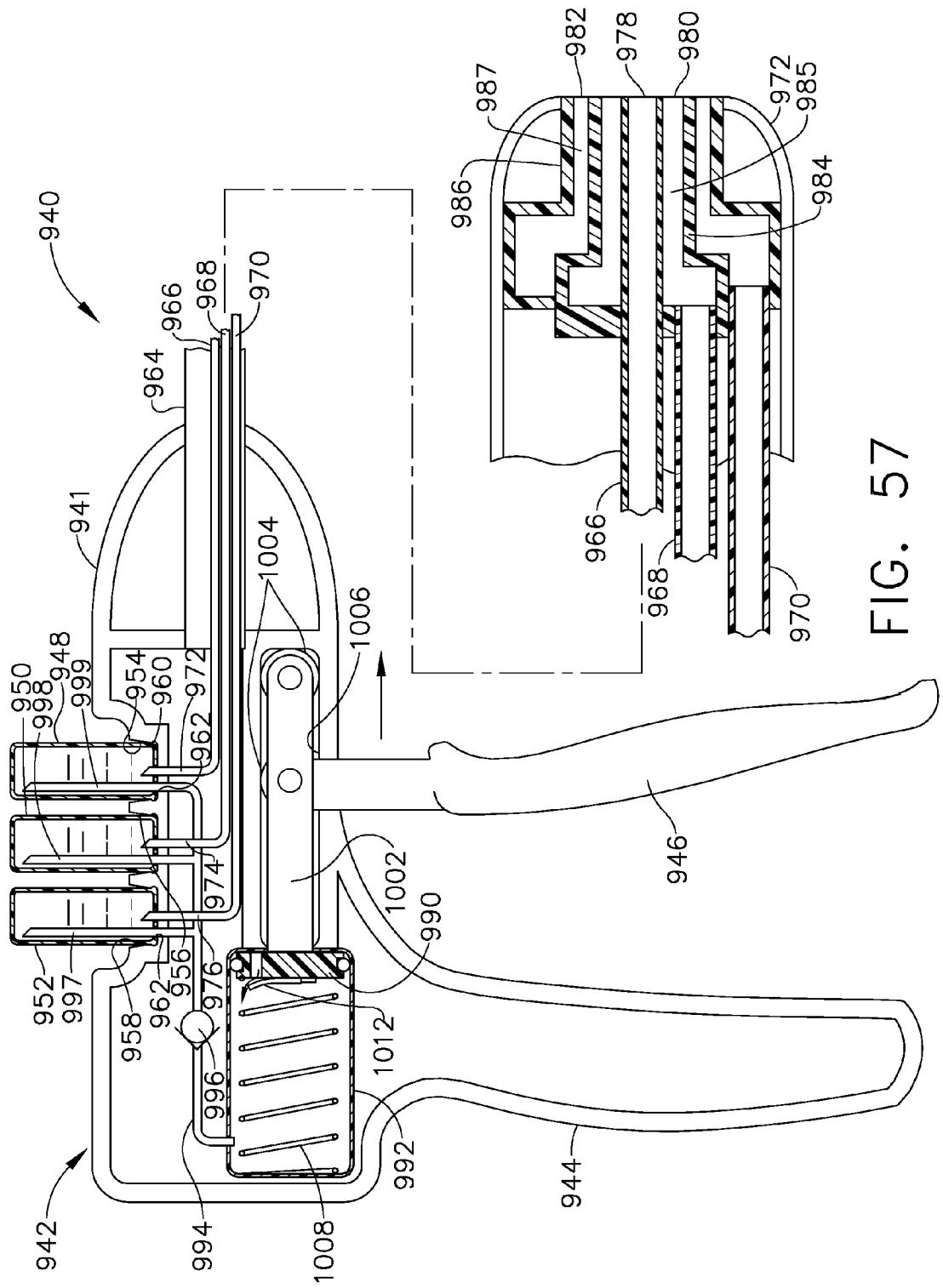
FIG. 57 depicts a partial cross-sectional view of an exemplary lumen repair device for coextruding a tissue repair plug.
Figure 58:
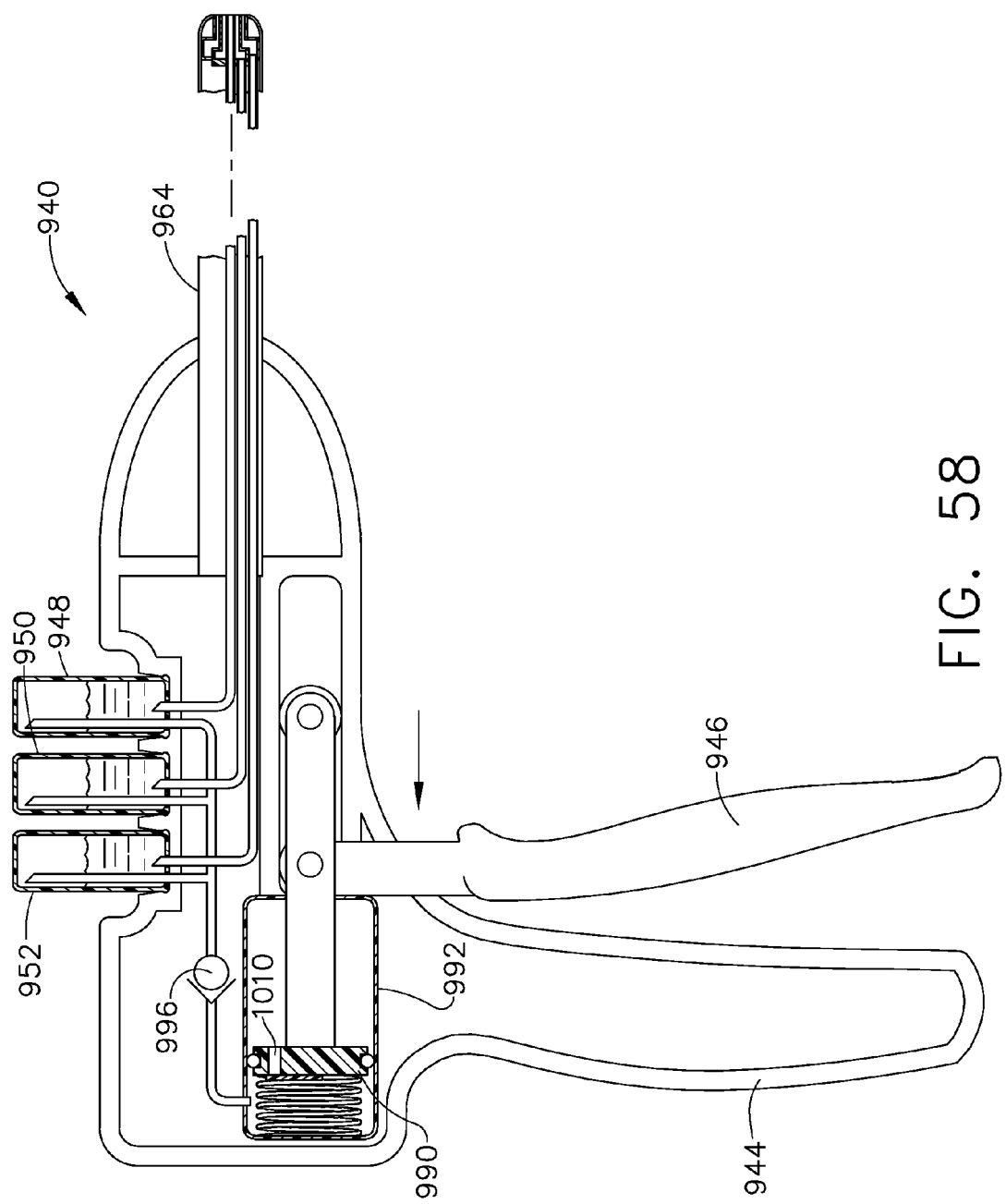
FIG. 58 depicts a partial cross-sectional view of the lumen repair device shown in FIG. 56, with the contents of the media chamber expelled therefrom.
Figure 59:
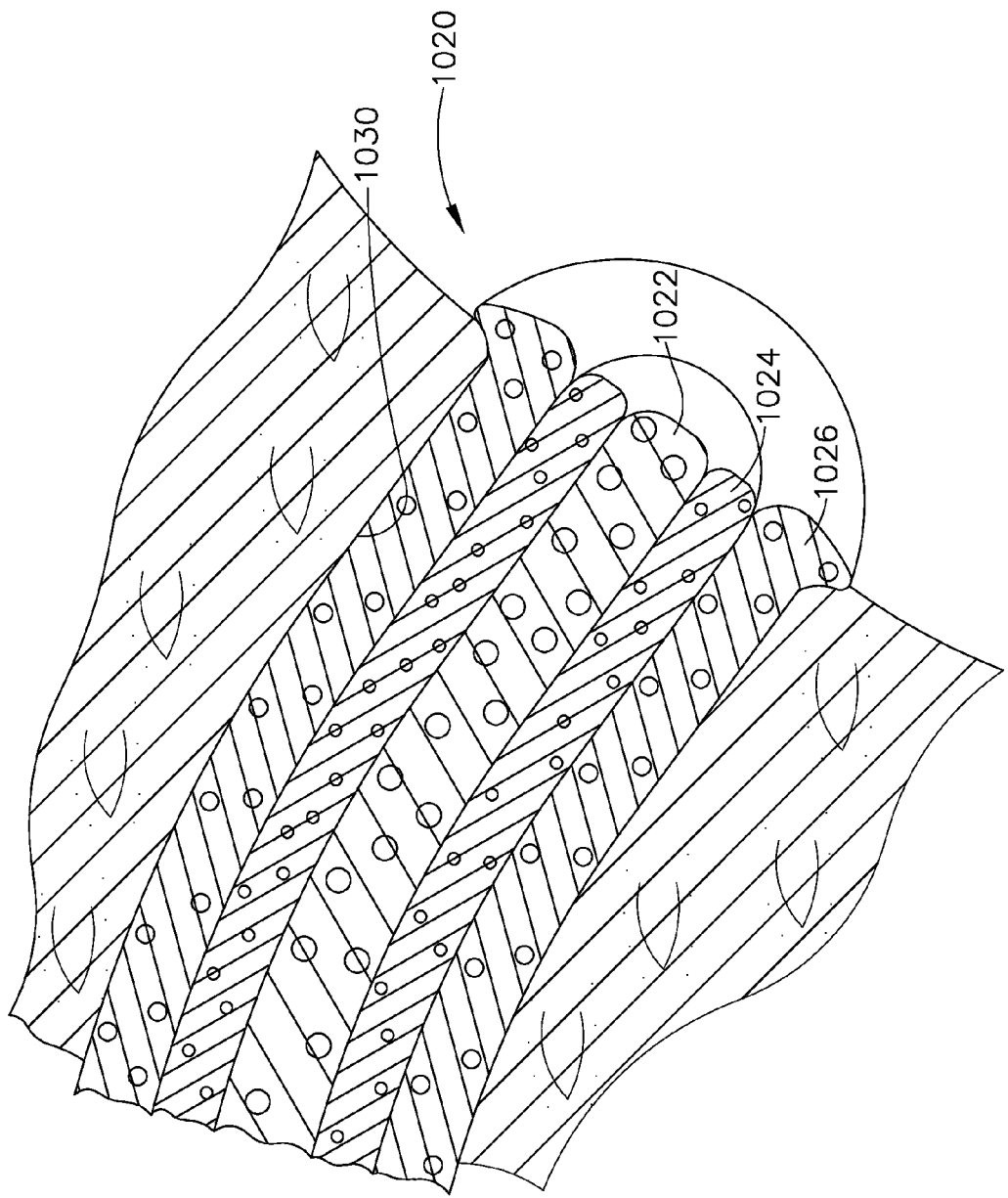
FIG. 59 depicts a partial cross-sectional view of a tissue repair plug created by the device shown in FIG. 56, positioned within an anal fistula.

FIGS. 57-59 depict yet another exemplary lumen repair device (940) that may be used to repair a lumen such as a fistula or perform other tasks at other target sites. By way of example, lumen repair device (940) may be used to coextrude a multilayered, semi-solid tissue repair plug that may be used to fill and repair a fistula. In particular, the lumen repair device (940) may coextrude the repair plug in situ, within an anal fistula (or other lumen). The semi-solid plug may be formed from any of a variety of components, as further described herein.

Lumen repair device (940) of the present example has a housing (941) that comprises a handle (942) having a grip portion (944) and a trigger (946) extending downwardly away from handle (942) in facing relationship to grip portion (944). A plurality of media reservoirs in the form of media chambers (948, 950, 952) are attached to handle (942), and each is depicted as a sealed housing containing a fluid, or otherwise flowable, media (e.g., a liquid or a semisolid material). Media chambers (948, 950, 952) may be provided in a variety of configurations for attachment to handle (942), and may be provided to an end-user prefilled, partially-filled, or empty. In the present example shown in FIG. 57, the bottom wall of each media chamber (948, 950, 952) comprises a self-sealing septum. Thus, media may be added to an empty or partially-filled chamber (948, 950, 952) using a syringe and needle to inject media through the self-sealing septum.

A plurality of mounting receptacles (954, 956, 958) are provided on an upper surface of handle (942), and are configured to receive the bottom end portion of media chambers (948, 950, 952) therein. Mounting receptacles (954, 956, 958) may have any of a variety of configurations for matingly and securely receiving a chamber (948, 950, 952) therein. As shown in FIG. 57, for example, an annular rib (960) extends around the bottom periphery of media chamber (948, 950, 952). Mounting receptacle (954, 956, 958) includes a corresponding groove (962) extending about the periphery of the inner base wall of the receptacle (954, 956, 958), where the groove (962) matingly receives annular rib (960). In this fashion, each chamber (948, 950, 952) may be inserted into a corresponding mounting receptacle (954, 956, 958) and urged downwardly until annular rib (960) is snapped into groove (962) to securely but removably mount each media chamber (948, 950, 952) in mounting receptacle (954, 956, 958).

A hollow, elongate shaft (964) is secured within, and extends distally away from, handle (942). As further described below, a plurality of conduits (966, 968, 970) extend through the interior of shaft (964), and each is open at its distal end located at the distal end (972) of shaft (964). Each conduit (966, 968, 970) includes a respective upwardly extending portion (972, 974, 976) that extends upwardly into a corresponding mounting receptacle (954, 956, 958). The proximal end of each upwardly extending portion (972, 974, 976) of conduits (966, 968, 970) has a pointed tip for penetrating the self-sealing septum in the bottom wall of media chambers (948, 950, 952). Thus, when a media chamber (948, 950, 952) is inserted into a mounting receptacle (954, 956, 958), the pointed proximal end of each upwardly extending portion (972, 974, 976) of conduits (966, 968, 970) will penetrate the septum and enter the lower portion of media chambers (948, 950, 952), thus providing communication between the interior of media chambers (948, 950, 952) and conduits (966, 968, 970). This arrangement allows media to be expelled from media chambers (948, 950, 952) into conduits (966, 968, 970) and through the length of shaft (964).

An orifice (978, 980, 982) is provided at the distal end of each conduit (966, 968, 970). As best seen in FIG. 57, the orifices (978, 980, 982) are located adjacent to one another on the distal end (972) of shaft (964). Orifices (978, 980, 982) may be positioned side-by-side on the distal end (972) of shaft (964) to deliver media as layers, one on top of another, to produce, for example, a multilayered tissue repair plug having a top, bottom and middle layer. In the example shown, however, orifices (978, 980, 982) are coaxial with one other on the distal end (972) of shaft (964) and deliver media therethrough in concentric layers to produce, for example, a multilayered tissue repair plug having a core, a middle layer surrounding the core, and an outer layer surrounding the middle layer as shown in FIG. 59.

In order to deliver media to concentric orifices (978, 980, 982), a distal portion of the three conduits (966, 968, 970) are concentric with one another. As shown in FIG. 57, first conduit (966) comprises a straight tube extending to first orifice (978). Second conduit (968) includes a concentric sleeve portion (984) that extends concentrically around first conduit (966) adjacent the distal end (972) of shaft (964) such that an annular lumen (985) is defined between concentric sleeve portion (984) and first conduit (968). Similarly, third conduit (970) includes a concentric sleeve portion (986) that extends concentrically around concentric sleeve portion (984) of second conduit (968) adjacent the distal end (972) of shaft (964) such that an annular lumen (987) is defined between concentric sleeve portion (986) of third conduit (970) and concentric sleeve portion (984) of second conduit (968). In this manner, when flowable media is urged from chambers (948, 950, 952) through conduits (966, 968, 970), the media will be expelled from the distal end (972) of shaft (964) in three coaxial layers.

Media may be expelled from chambers (948, 950, 952) through conduits (966, 968, 970) in any of a variety of ways. In the example shown, a gas (e.g., air) is selectively forced into each chamber (948, 950, 952) so as to expel the media from each chamber (948, 950, 952) into the conduits (966, 968, 970). In particular, trigger (946) is the actuator for driving a piston (990) that forces air into each chamber (948, 950, 952).

Piston (990) is sealingly positioned within a cylinder (992). An air conduit (994) is in fluid communication with cylinder (992) adjacent the proximal end of cylinder (992). A check valve (996) is provided on air conduit (994) and prevents air or other media from flowing back into cylinder (992) through air conduit (994). A plurality of upwardly extending air tubes (997, 998, 999) extend upwardly into a respective mounting receptacle (954, 956, 958), and each air tube (997, 998, 999) is in fluid communication with air conduit (994) at its lower end. The upper end of each air tube (997, 998, 999) has a pointed tip for penetrating the self-sealing septum in the bottom wall of corresponding media chambers (948, 950, 952). Thus, when a media chamber (948, 950, 952) is inserted into a mounting receptacle (954, 956, 958), the pointed upper end of each air tube (997, 998, 999) will penetrate the septum and enter the upper portion of media chambers (948, 950, 952), above the media contained within chambers (948, 950, 952). Thus, when piston (990) is urged proximally (i.e., away from shaft (964)), air within cylinder (992) will be expelled therefrom through gas conduit (994), through upwardly extending air tubes (997, 998, 999), and into chambers (948, 950, 952). The air will increase the head space pressure in chambers (948, 950, 952), causing the media contained therein to be expelled into the conduits (966, 968, 970) and subsequently out the orifices (978, 980, 982) on the distal end (972) of shaft (964).

In order for trigger (946) to drive piston (990), an arm (1002) is pivotally attached to the upper end of trigger (946). Arm (1002) is supported by a pair of wheels (1004) rotatably attached to arm (1002) and rollingly supported within an elongate slot (1006). The proximal end of arm (1002) is attached to piston (990), as shown. As trigger (946) is squeezed towards grip portion (944), the movement of trigger (946) is translated to longitudinal movement of arm (1002) away from shaft (964). The longitudinal movement of arm (1002) urges piston (990) proximally to expel air from cylinder (992). In this fashion, trigger (946) is used to pump air into chambers (948, 950, 952) for expelling media therefrom.

In order to allow the user to repeatedly pump air into chambers (948, 950, 952), piston (992) is also spring-biased in the distal direction by a spring (1008) in cylinder (992). In addition, an aperture (1010) extends through piston (990) and is covered by a flexible flap valve (1012) attached to the inner wall of piston (990), adjacent aperture (1010). When trigger (946) is squeezed towards grip portion (944) to pump air into chambers (948, 950, 952), flap valve (1012) is forced against the inner wall of piston (990) by the air pressure within cylinder (992) and sealingly covers aperture (1010). When trigger (946) is released, spring (1008) urges piston (990) in the distal direction and flap valve (1012) opens (see FIG. 57) to allow air to refill cylinder (992). In addition, distal movement of piston (990) caused by spring (1008) will also urge trigger (946) away from grip portion (944) to its initial position shown in FIG. 57. The end-user may then resqueeze the trigger (946) towards grip portion (944) in order to pump additional fluid into chambers (948, 950, 952). This process may be repeated as many times as necessary to expel media from chambers (948, 950, 952) and coextrude a semisolid tissue repair plug delivered from the distal end (972) of shaft (964). Of course, lumen repair device (940) may instead be actuated in any other suitable fashion.

A variety of different media may be used with the lumen repair device (940) of FIGS. 57-59. For example, a first media comprising platelet-rich plasma may be provided in first reservoir (948). A second media comprising, for example, a plurality of viable tissue fragments suspended in a suitable carrier, may be provided in second reservoir (950). The tissue fragments may be harvested in any of a variety of ways, such as those described previously herein. A third media comprising, for example, a growth factor medical fluid having one or more growth factors therein, may be provided in third reservoir (952). Suitable growth factors include, for example, fibroblast growth factors (FGFs), platelet-derived growth factor (PDGF), and transforming growth factor (TGF). Of course, any other suitable fluids or materials may be provided in reservoirs (948, 950, 952), including but not limited to any suitable number and/or combination of the various medical fluid components referred to herein.

In an exemplary use, a fistula is first prepared for repair, such as by debriding the fistula, cleaning out the fistula, and/or taking any other suitable preparatory measures. With the lumen repair device (940) loaded with suitable media, the distal end (972) of shaft (964) is inserted through the first (e.g., external) opening of the fistula until the distal end (972) is located at the second (e.g., internal) opening of the fistula. Trigger (946) is then repeatedly squeezed towards grip portion (944) such that the media from chambers (948, 950, 952) is coextruded into a semisolid plug expelled from the distal end (972) of shaft (964) into the fistula. Alternatively, distal end (972) of shaft (964) may be inserted through the second (e.g., internal) opening of the fistula until the distal end (972) is located at the first (e.g., external) opening of the fistula. As the plug is coextruded, the shaft (964) is withdrawn from the fistula, thus filling the entire fistula with the semisolid, multilayered plug, as shown in FIG. 59. The various layers of the plug will blend together somewhat, and portions of the plug will dissolve or be reabsorbed into the patient's body. Viable cells in the tissue fragments will proliferate and integrate with surrounding tissue in the fistula, thereby repairing the fistula. FIG. 59 depicts an example of such a fistula repair plug (1020) positioned within an anal fistula (1030). Repair plug (1020) includes a cylindrical core layer (1022), surrounded by a second layer (1024), which is surrounded by a third layer (1026). Other suitable variations, components, features, configurations, and operabilities of repair device (940) will be apparent to those of ordinary skill in the art in view of the teachings herein.

XI. Miscellaneous

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of the devices described above may be actuated mechanically or electromechanically (e.g., using one or more electrical motors, solenoids, etc.). However, other actuation modes may be suitable as well including but not limited to pneumatic and/or hydraulic actuation, etc. Various suitable ways in which such alternative forms of actuation may be provided in a device as described above will be apparent to those of ordinary skill in the art in view of the teachings herein.

Versions of the devices described above may have various types of construction. By way of example only, any of the devices described herein, or components thereof, may be constructed from suitable metals, ceramics, plastics, or combinations thereof. Furthermore, although not required, the construction of devices described herein may be configured to be compatible with or optimize their use with various imaging technologies. For instance, a device configured for use with MRI may be constructed from all non-ferromagnetic materials. Also for instance, when using optional imaging technologies with devices described herein, certain configurations may include modifications to materials of construction such that portions or the device may readily appear in a resultant image. Various suitable ways in which these and other modifications to the construction of devices described herein may be carried out will be apparent to those of ordinary skill in the art in view of the teachings herein.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical device for formulating and delivering a tissue repair composition into a lumen in a patient, comprising:
   (a) a housing;
   (b) a bioprocessing module operatively mounted to the housing, the bioprocessing module comprising a plurality of media reservoirs, a plurality of fluid conduits in communication with the plurality of reservoirs, and a port through which media is expelled;
   (c) a first end effector attached to the housing and extending distally away from the housing, the end effector being configured for insertion into a lumen and delivering a tissue repair composition into that lumen, the end effector having at least one fluid conduit extending therethrough and at least one orifice in communication with the fluid conduit, wherein the fluid conduit in the first end effector is in fluid communication with the port on the bioprocessing module; and
   (d) a pumping device for urging a tissue repair composition comprising at least a portion of the contents of the plurality of media reservoirs through the fluid conduit of the first end effector such that the tissue repair composition is expelled from the at least one orifice;
   wherein the bioprocessing module further comprises a mixing chamber in fluid communication with the plurality of reservoirs via reservoir fluid conduits extending between each of the reservoirs and the mixing chamber, wherein the mixing chamber is also in fluid communication with the port via a fluid conduit, and
   wherein the bioprocessing module further comprises a morcellating chamber in fluid communication with the mixing chamber, the morcellating chamber being configured to morcellate tissue specimens therein into smaller tissue fragments for subsequent delivery into the mixing chamber.

2. The surgical device of claim 1, further comprising at least one valve on each of the reservoir fluid conduits for selectively controlling the delivery of media from the reservoirs into the mixing chamber, and a valve on the fluid conduit between the mixing chamber and the port in order to selectively control the delivery of a tissue repair composition from the mixing chamber into the fluid conduit of the first end effector.

3. The surgical device of claim 2, further comprising a processor operatively coupled with the valves, wherein the processor is configured to regulate delivery of media from the reservoirs into the mixing chamber.

4. The surgical device of claim 3, wherein the control system is configured to cause, in accordance with predetermined instructions:
   (i) tissue specimens to be morcellated within the morcellating chamber,
   (ii) the resulting tissue fragments to be delivered to the mixing chamber,
   (iii) media from the media reservoirs to be expelled into the mixing chamber,
   (iv) the contents of the mixing chamber to be mixed in order to formulate a tissue repair composition, and
   (v) a signal to be provided to an end-user that the tissue repair composition within the mixing chamber is ready for delivery into a lumen in a patient.

5. The surgical device of claim 1, wherein the mixing chamber is pressurizable, wherein the pumping device comprises a source of pressurized gas in fluid communication with the mixing chamber, such that tissue repair composition may be expelled from the mixing chamber into the first end effector by the pressurized gas.

6. The surgical device of claim 5, further comprising:
   (a) at least one valve on each of the reservoir fluid conduits for selectively controlling the delivery of media from the reservoirs into the mixing chamber;
   (b) a valve on the fluid conduit between the mixing chamber and the port in order to control the delivery of tissue repair composition from the mixing chamber into the fluid conduit of the first end effector; and
   (c) a control system operatively connected to the valves, wherein the control system is configured to regulate the delivery of media from the reservoirs into the mixing chamber and the delivery of tissue repair composition from the mixing chamber into the first end effector;
   wherein the reservoirs are pressurizable and the source of pressurized gas is in fluid communication with each of the reservoirs; and
   wherein the control system is operable to cause fluid media to be delivered from the media reservoirs into the mixing chamber by selectively causing the valves on the reservoir fluid conduits to open, and wherein the control system is operable to cause a tissue repair composition to be urged through the fluid conduit of the end effector by selectively causing the valve on the fluid conduit between the mixing chamber and the port to open.

7. The surgical device of claim 1, wherein at least one of the media reservoirs is in fluid communication with the morcellating chamber in order to selectively deliver media from the reservoir into the morcellating chamber.

8. The surgical device of claim 1, further comprising a second end effector, wherein the first and second end effectors are removably attachable to the housing, wherein the second end effector is operable to harvest at least one tissue specimen, and further wherein the surgical device is configured to deposit a tissue specimen harvested by the second end effector into the morcellating chamber.

9. The surgical device of claim 1, wherein the first end effector has first and second fluid conduits extending therethrough and first and second orifices in respective communication with the first and second fluid conduits, wherein the first conduit of the first end effector is in fluid communication with the mixing chamber via the port, and the second conduit of the first end effector is in fluid communication with at least one of the media reservoirs.

10. The surgical device of claim 1, further comprising a display screen for displaying information to an end-user during use of the surgical device.

* * * * *